(12) United States Patent
Hyland et al.

(10) Patent No.: US 9,354,998 B2
(45) Date of Patent: May 31, 2016

(54) AUTOMATED CONFORMANCE AND INTEROPERABILITY TEST LAB

(71) Applicant: AEGIS.net, Inc., Rockville, MD (US)

(72) Inventors: Mario G. Hyland, Clarksburg, MD (US); Richard J. Ettema, Manassas, VA (US); Sunil K. Bhaskarla, Olney, MD (US); Tareq I. Nabeel, Germantown, MD (US)

(73) Assignee: AEGIS.net, Inc., Rockville, MD (US)

( * ) Notice: Subject to any disclaimer, the term of this patent is extended or adjusted under 35 U.S.C. 154(b) by 197 days.

(21) Appl. No.: 13/886,793

(22) Filed: May 3, 2013

(65) Prior Publication Data
US 2013/0297973 A1 Nov. 7, 2013

Related U.S. Application Data

(60) Provisional application No. 61/642,861, filed on May 4, 2012.

(51) Int. Cl.
*G06F 11/00* (2006.01)
*G06F 11/28* (2006.01)
*G06F 11/36* (2006.01)
*G06F 19/00* (2011.01)

(52) U.S. Cl.
CPC ............ *G06F 11/28* (2013.01); *G06F 11/3664* (2013.01); *G06F 11/3688* (2013.01); *G06F 19/322* (2013.01); *G06F 19/3412* (2013.01)

(58) Field of Classification Search
USPC ................................................ 714/27; 705/2
See application file for complete search history.

(56) References Cited

U.S. PATENT DOCUMENTS

| | | | |
|---|---|---|---|
| 6,985,445 B1 | 1/2006 | Hao et al. | |
| 7,216,338 B2 | 5/2007 | Barnett et al. | |
| 7,237,014 B2 | 6/2007 | Drummond, II | |
| 7,313,564 B2 | 12/2007 | Melamed et al. | |
| 7,403,901 B1 * | 7/2008 | Carley et al. | 705/2 |
| 7,617,159 B1 | 11/2009 | Donner | |
| 7,675,948 B2 | 3/2010 | Malomsoky et al. | |
| 8,000,977 B2 * | 8/2011 | Achan | 705/2 |
| 8,303,309 B2 * | 11/2012 | Hoffmann et al. | 434/117 |
| 2002/0188698 A1 * | 12/2002 | Jensen et al. | 709/219 |
| 2003/0159132 A1 * | 8/2003 | Barnett et al. | 717/124 |
| 2003/0233395 A1 | 12/2003 | Cherian et al. | |
| 2005/0149630 A1 * | 7/2005 | Smolinski et al. | 709/227 |
| 2007/0165625 A1 * | 7/2007 | Eisner et al. | 370/389 |
| 2008/0130514 A1 | 6/2008 | Soon et al. | |
| 2009/0327812 A1 | 12/2009 | Zhang et al. | |
| 2010/0077079 A1 * | 3/2010 | Xu | G06F 11/2294 709/226 |
| 2010/0333168 A1 * | 12/2010 | Herrod | 726/1 |
| 2012/0124075 A1 * | 5/2012 | Galluscio | 707/769 |
| 2013/0212129 A1 * | 8/2013 | Lawson et al. | 707/779 |
| 2013/0212214 A1 * | 8/2013 | Lawson et al. | 709/217 |
| 2014/0336791 A1 * | 11/2014 | Asenjo et al. | 700/44 |
| 2014/0336795 A1 * | 11/2014 | Asenjo et al. | 700/86 |
| 2014/0337086 A1 * | 11/2014 | Asenjo et al. | 705/7.28 |
| 2014/0337277 A1 * | 11/2014 | Asenjo et al. | 707/603 |
| 2014/0337429 A1 * | 11/2014 | Asenjo et al. | 709/204 |

* cited by examiner

*Primary Examiner* — Kamini Patel
(74) *Attorney, Agent, or Firm* — AuerbachSchrot LLC; William C. Schrot

(57) ABSTRACT

A set of self-service testing tools and processes used to conduct gateway to gateway testing. The system includes a test harness comprising a collection of software and test data configured to test a program unit by running it under varying conditions and monitoring its behavior and outputs. The test harness allows for the automation of tests, and can call functions with supplied parameters and analyze results to a desired value.

28 Claims, 51 Drawing Sheets

FIGURE 20

Test Case: PDI-1.1a

Patient Discovery Specification version 0.9
3.1.4 Demographic requirements in request and response
Gateways should specify an appropriate collection of demographics that balance the needs of:
a) Reliable demographic matching to ensure a minimum of false negative and false positive matches
b) Avoidance of privacy issues in case of a security break especially to avoid potential for identity fraud as a result of a security break
Required values for the Patient Discovery request:

- LivingSubjectName Parameter: Both "family" and "given" elements are required. If patients are known by multiple names or have had a name change, the alternative names shall be specified as multiple instances of LivingSubjectName. Inclusion of all current and former names increases the likelihood of a correct match but may incur privacy concerns. The sequence of given names in the given name list reflects the sequence in which they are known – first, second, third etc. The first name is specified in the first "given" element in the list. Any middle name is specified in the second "given" element in the list when there are no more than two "given" elements.
- LivingSubjectAdministrativeGender Parameter: Is required. Coded using the HL7 coding for AdministrativeGender; namely code equal to one of "M" (Male) or "F" (Female) or "UN" (Undifferentiated).
- LivingSubjectBirthTime Parameter: Is required. The contents must contain the greatest degree of detail as is available.

Required values for the Patient Discovery response (unless the Shared/national Patient Identifier Query and Feed mode is used):

- Person.name element: Both "family" and "given" elements are required. If patients are known by multiple names or have had a name change, the alternative names shall be specified as multiple Patient.name elements. Inclusion of all current and former names increases the likelihood of a correct match. The sequence of given names in the given name list reflects the sequence in which they are known – first, second, third etc. The first name is specified in the first "given" element in the list. Any middle name is specified in the second "given" element in the list when there are no more than two "given" elements.
- Person.administrativeGenderCode element: Is required. Coded using the HL7 coding for AdministrativeGender; namely code equal to one of "M" (Male) or "F" (Female) or "UN" (Undifferentiated).
- Person.birthTime Parameter: Is required. The contents must contain the greatest degree of detail as is available.

FIGURE 40

AUTOMATED CONFORMANCE AND INTEROPERABILITY TEST LAB

CROSS REFERENCE TO RELATED APPLICATION AND CLAIM TO PRIORITY

The present invention is based on U.S. Provisional Patent Application Ser. No. 61/642,861, filed May 4, 2012, the disclosure of which is incorporated herein by reference in its entirety and to which priority is claimed.

FIELD OF THE INVENTION

The present invention relates to an automated test lab for bidirectional conformance and interoperability testing of a system against multiple gateways.

BACKGROUND OF THE INVENTION

The Health Information Technology for Economic and Clinical Health Act ("HITECH Act") is part of the American Recovery and Reinvestment Act of 2009 (ARRA). The ARRA HITECH Act facilitates the expansion of the electronic exchange of health information on a national basis to make medical care more organized and transparent. It also contains incentives designed to accelerate the adoption of electronic health record (EHR) systems among providers.

The Nationwide Health Information Network (NHIN or NwHIN) is an interoperable health information infrastructure, developed for the purpose of securely connecting consumers, providers and others who have, or use, health-related data and services, while protecting the confidentiality of health information. NHIN provides a set of standards, services and policies that enable secure and meaningful health information exchange over the Internet.

The health information exchange (HIE or "the Exchange") is the transmission of healthcare-related data among facilities, health information organizations (HIO) and government agencies according to national standards. The Exchange seeks to connect diverse entities needing to exchange health information, such as state and regional entities, integrated delivery networks (IDNs), personally controlled health records (PCHRs), federal and state government agencies, and their component networks. The Exchange permits the transmission of healthcare-related data among facilities, health information organizations (HIOs) and government agencies according to national standards.

Accordingly, interoperability has become a centerpiece for healthcare systems, providing a means to prevent fraud, waste, and abuse, improve quality of care, and improve the usability of medical information. Facilitating the secure exchange of health information is a system's interoperability architecture consisting of an Electronic Health Record (EHR), Electronic Medical Record (EMR), or other medical device, along with a gateway technology for sending and receiving well formatted web service calls. However, a system's interoperability architecture is delicate, and demonstrating interoperability is a difficult undertaking.

To meet requirements, the Exchange must enable reliable and secure transfer of data among diverse systems and also facilitate access and retrieval data. The Nationwide Health Information Network Validation Plan describes the approach, processes, and requirements for validating that an Applicant has met the requirements for participation in the Exchange. The intent of the Validation Plan is to describe the general principles and processes guiding validation for an Applicant to participate in the Exchange. To meet requirements for trust and interoperability in the Exchange, the validation process verifies Applicants can securely exchange information with other Exchange participants, while maintaining the privacy of the information exchanged. The validation approach seeks to confirm that an Applicant's technical implementation of NHIN specifications complies with the network performance and service specifications.

Participation in the Exchange is predicated on an Applicant meeting defined requirements for participation, including organizational, technical, and operational criteria. The Exchange validation process manually tests adherence to the specifications and technical criteria for participating in the Exchange. In order to successfully exchange information over the Exchange, an entity or Applicant must undergo an onboarding process. The onboarding process takes the Applicant's HIT gateway application through several phases, namely conformance testing (testing to ensure that the organization adheres to the NHIN specifications) and interoperability testing (testing to ensure that the organization can communicate with other NHIN participants using various services).

Generally, the onboarding process may be initiated when an Applicant requests and then submits an application to the Onboarding Team. The Team then reviews the application, and forwards it along to a Coordinating Committee for further review and eligibility determination. If eligible, the Onboarding Team sends test certificate and validation framework information to the Applicant. The Applicant configures its test environment and conducts conformance testing and interoperability testing. The Team collects testing logs from the Applicant and conducts its own analysis for conformance and interoperability testing. The Team then prepares a validation summary report, which is submitted to the Coordinating Committee. If required, the Applicant submits a remediation plan to the Onboarding Team for further review. The Coordinating Committee then provides a summary report and remediation plan (if applicable), and determines whether to grant conditional approval for the Applicant to attain participant status on the Exchange. The Applicant is then notified of participant status, and provided an activation packet. After receiving the activation packet from the Applicant, the Onboarding Team configures the Exchange registry with the Applicant's information. The Applicant is then an active participant and able to exchange data over the Exchange.

The onboarding process is very time consuming and relatively complicated. Within the Network, two concerns must be realized: that each participating system conforms to the applicable NHIN specifications, and that each participating system can interact with the others. Conformance does not necessarily guarantee interoperability. Similarly, interoperability does not necessarily guarantee conformance.

Manual testing tool systems have been utilized to test that an Applicant conforms to NHIN specifications, and to ensure that the Applicant system can interoperate with other NHIN participants for common business functions.

Conformance testing focuses on validating a single system to a specific set of standards and specifications. This testing primarily confirms that a system correctly encodes the syntax and structure of a given data standard in the physical files or transactions that a system produces and receives. Conformance testing is performed based on a set of resources, including test cases and data, testing guidance documents, supporting processes, and manual or automated test tools and capabilities.

Interoperability Testing seeks to validate that multiple systems implementing a particular standard or set of standards can all communicate with one another. Interoperability testing is performed based upon a set of resources, including interoperability test cases and scenarios, related criteria, test scripts, supporting processes, and automated testing tools. Although in theory passing interoperability tests implies interoperability between participating systems, such interoperability is not guaranteed. As such, it may be beneficial for an Applicant and/or participant system to conduct additional testing.

Thus, healthcare organizations must properly interoperate with one another for compliance. Although many organizations and vendors assume or assert that their electronic information (e.g., electronic health and medical records) are indeed interoperable with one another, many organizations and vendors are encountering difficulties in exchanging health information using standards outlined by various agencies, and are unable to properly exchange information. The architecture of many systems' interoperability components are fragile and prone to inoperability. Moreover, the numerous vendors and organizations utilize different means of interpreting standards and thus may not always implement a working system.

SUMMARY OF THE INVENTION

The present invention is directed to a self-service, automated test lab or system, referred to herein as "the Developers Integration Lab" (DIL) or "the Test Lab" or "the Lab", including bi-directional conformance and interoperability testing against multiple gateways, and as the system is being built. The DIL provides a method to test 'Direct' Secure Multipurpose Internet Mail Extensions utilizing a Simple Mail Transfer Protocol (SMTP) server and all items described within a Direct Health Information Service Provider (HISP), including Domain Name System (DNS) and Lightweight Directory Access Protocol (LDAP), and web service protocols as described belonging to an HISP. The DIL is not limited to testing Healthcare IT systems; it can be used to test any standards based web service Extensible Markup Language (XML) messages.

A primary purpose of the NHIN is to utilize a shared architecture (services, standards, and requirements) to interconnect health information exchanges and the participants/users supported. As the specifications for the NHIN have evolved, the need for a test lab to easily support multiple gateways utilizing a Service-Oriented Architecture (SOA) has arisen. The automated test lab of the present invention ensures that candidates can quickly determine the results of the testing.

Test-driven Development (TDD) is prudent practice in effective development teams. These teams know that rigorous testing of the code during the development process produces software with fewer defects than the legacy approach of waiting until later in the development cycle to test. The result is sane developers and happier customers. Interoperability Test-driven Development ("ITDD") applies the same principles by incorporating the automated testing of interoperability into the development lifecycle. Savvy CONNECT users will want to take advantage of this new paradigm to help avoid the perils of procrastination.

The conformance and interoperability Test Lab uses event based gateways with initiator and responder scenarios, ensuring candidates possess the ability to communicate with other gateways. Using an SOA based framework, the DIL is able to provide candidates the ability to test any number of gateway implementations (e.g., test scenarios using CONNECT 2.4.8, CONNECT 3.2, CONNECT 3.3, Integrating the Healthcare Enterprise (IHE) XCPD, XCA, XDS.b among other non-Health IT implementations). The DIL provides methods for testing Patient Discovery (XCPD) as well as Query for Documents and Retrieve Documents (XCA) services. Candidates can test these services using various gateway implementations.

Thus, the DIL provides a relatively simple and easily navigable user interface. Within minutes, a candidate can register on the DIL, install certificates, and begin using the DIL. A Gateway Farm and a backend Fuse enterprise service bus (ESB) implementation allow DIL users the capability to test multiple gateways within multiple scenarios and services. The Universal Description Discovery and Integration (UDDI) Manager provides a user friendly interface to validate endpoints for candidates to perform various services (XCPD or XCA). The DIL provides a method to manage and distribute certificates to enable the secure exchange of web services and information in the capacity of a certificate authority. The DIL can generate x.509 certificates including (but not limited to), v1, v2, and v3 through a certificate authority interface. Certificate Management via EJBCA facilitates secure communication between Gateways.

According to one embodiment of the present invention, an automated test lab for bidirectional conformance and interoperability testing of an applicant system gateway against a participating system gateway in an information exchange network comprises: a bidirectional gateway adapter configured to intercept web service messages between a sending gateway and a receiving gateway, and deliver the intercepted messages to the sending gateway or the receiving gateway; an ESB in communication with the gateway adapter and providing an integration platform configured to control the intercepted messages and execute test scenarios based on the intercepted messages for determining compliance with a set of communication standards; and a web application in communication with the ESB and configured to initiate through a user interface execution of the test scenarios, and to validate results of the executed test scenarios. In one implementation, the web application of the automated test lab is also configured to create and manage the test scenarios through the user interface.

In some embodiments, the ESB comprises a test case processor configured to determine whether each of the intercepted messages complies with the set of communication standards. An error message is generated and sent to the sending gateway in response to a noncompliant intercepted message, and a compliant intercepted message is distributed to the receiving gateway. In some embodiments, the ESB may comprise a test lab database configured for storing one or more of test scenarios, results of executed test scenarios, intercepted messages, and audit information. In some embodiments, the ESB is further configured to generate and send test data to the applicant system gateway for determining compliance with the set of communication standards, and monitoring and validating responses to the test data by the applicant system gateway.

Each of the test scenarios comprise one of an initiator scenario or a responder scenario. The initiator scenario tests compliance with the set of communication standards for requesting or sending information by the applicant system gateway to the participating system gateway. The responder scenario tests compliance with the set of communication standards for receiving requests or information from the participating system gateway to the applicant system gateway.

In some embodiments, the information exchange network is a shared architecture of multiple systems configured to interconnect health information exchange. In some embodiments, the test lab simultaneously tests multiple applicant system gateways against multiple participating system gateways. Gateway SOAP messages are captured using a Gateway agent.

The present invention also provides for a method of testing conformance and interoperability of an applicant system gateway against a participating system gateway in an information exchange network, comprising the steps of: generating a request message from an initiating gateway for a specified receiving gateway. The test gateway system identifies the sending gateway as the applicant system gateway, and determines whether the intercepted message complies with a set of communication standards. An error message is generated in response to a noncompliant intercepted message, and a validation message is generated in response to a compliance intercepted message.

In some embodiments, the test gateway system additionally generates a test scenario for determining compliance with the set of communication standards, sends the test scenario to the applicant system gateway, and monitors and validates a response by the applicant system gateway in response to the test scenario. The test gateway system may be in communication with a user interface, wherein the generation of the test scenario is in response to a user request via the user interface. In one implementation, the test scenario comprises a request to the applicant system gateway for information from the information exchange network. Test Cases are generated within a Service Set. A Service Set is made up of multiple scenarios. Scenarios can be of type 'Initiating' or 'Responding', and subsequently test the System Under Test (SUT)'s ability to initiate a message to a reference implementation gateway within the DIL, or respond appropriately to a message sent from the DIL to the SUT's system. A scenario is made up of one or more test cases, testing multiple types of services. These web services are not just for those to exchange health information bi-directionally; rather any type of web service call can be tested within this type of architecture. The test case defines multiple elements which must be sent or returned successfully by a SUT. These elements will be present within the XML SOAP messages.

In some embodiments, the disclosed method comprises the further step of validating the intercepted message as either a compliant message or a noncompliant message, and sending a corresponding validation or error message to the applicant system gateway. Test cases are created within the DIL and can be used among multiple system participants (users of the DIL system). These tests are coded within XML utilizing various standards (i.e. in Health IT, using the HL7v3 format). Various rules to validate the XML message received by the SUT are built using the Extensible Style sheet Language Transformations (XSLT). Rules provide a method to validate SOAP message structure and ensure selected elements are properly sent or returned within the scope of a test case. Within the scope of Health IT, these elements may include information regarding a selected patient name, medical information, or demographics including address, phone number, etc.

Thus, an innovative platform to test gateway to gateway communications is provided, with a flexible framework supporting multiple services and a streamlined user interface that Applicants can easily begin using right out of the box.

The disclosed system and method permits vendors to demonstrate interoperability within a DIL Ecosystem option, including, but not limited to, monitoring patients as they progress through a medical episode. A sample population affected by a medical event or episode can at any time be injected into the disclosed system and tracked through the course of treatment. Interoperability may then be readily demonstrated to improve individual medical outcomes, as patients can be semantically understood within multiple vendor systems, enabling reliable, ready access to their medical information by multiple specialists and providers during the treatment process.

The system enables a shared learning culture among stakeholders sharing healthcare or any type of information and subsequently strengthening patient-clinician outcome partnerships through better patient portals and increased availability of lay-oriented, user-friendly clinical and nonmedical health data. The web applications and user interface, or portal, of the disclosed systems provide vendors a way to exhibit their interoperability architecture, metrics, and reports displaying how well they communicate at the technical and semantic level with other vendors. This in turn enables consumers to make adequate and informed decisions on purchasing a healthcare system for their healthcare practice, hospital, or organization.

In addition, the DIL provides a method to test 'Direct' Secure Multipurpose Internet Mail Extensions utilizing a Simple Mail Transfer Protocol (SMTP) server and all items described within a Direct Health Information Service Provider (HISP), including Domain Name System (DNS) and Lightweight Directory Access Protocol (LDAP), and web service protocols as described belonging to a HISP. Thus, the DIL is not limited to testing Healthcare IT systems. It can be used to test any standards-based web service Extensible Markup Language (XML) messages.

BRIEF DESCRIPTION OF THE DRAWINGS

FIGS. 12-34 illustrate screen views of the DIL software according to the present invention, and showing process steps and functionality for establishing an account in the DIL, establishing a static test case scenario, executing a test case scenario and viewing results from the executed test case scenario;

FIGS. 35-42 illustrate screen views of the DIL software according to the present invention, and showing process steps and functionality for establishing system templates for executing dynamic test scenarios;

DETAILED DESCRIPTION OF THE INVENTION

Empirical data has been collected by the Standards and Interoperability (S&I) Test and Infrastructure Team showing that numerous applicants for NHIN participation arrive to conduct conformance testing never having tested gateway-to-gateway communication. This represents a significant risk to the Validation Team as they manage their schedule and develop approaches to scale their processes.

The DIL provides an environment for participants to experience gateway-to-gateway communication testing earlier in the development and implementation phase of a candidate's Health Information Technology (HIT) projects. It also provides an independent testing environment for emerging NHIN specifications and their implementations for the CONNECT platform or other commercial gateway products (e.g., such as Axolotl by Optum, San Jose, Calif.). The DIL provides an independent testing environment for future CONNECT releases and an integration environment to support code contribution from the open source community, including Federal Partners.

Thus, the DIL facilitates process improvement by allowing the NHIN Validation (On-Boarding) candidates to possess the requisite knowledge before starting conformance testing. In addition, it provides a platform for non-CONNECT gateway products to test NHIN conformance and interoperability with the NHIN specifications. The DIL provides a community approach to open source development contribution and integration by providing independent and enhanced testing capabilities.

Figure 1:
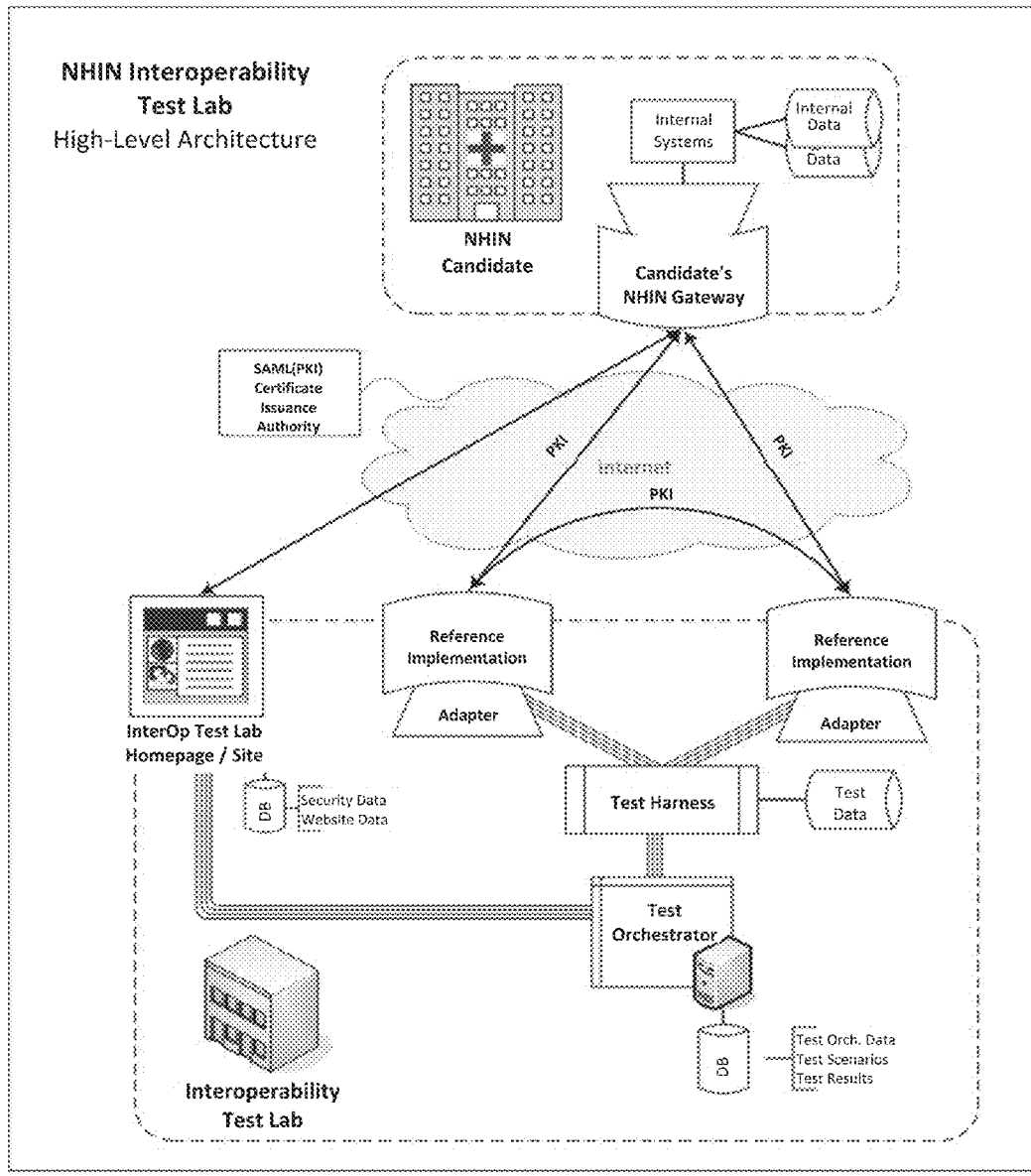
FIG. 1 illustrates a portion of the architecture of the DIL according to an embodiment of the present invention.

FIG. 1 illustrates a schematic diagram of architecture of an interoperability testing lab. The testing attempts to ensure that an Applicant and potential participant of the Exchange operates in a way that conforms to NHIN specifications. Validation confirms the testing results, which are considered during the onboarding process for NHIN participation.

As shown in FIG. 1, the architecture is broken down into two sections: a gateway and an adapter, each with services and components. The adapter incorporates those components deemed most likely to be customized or replaced by an organization to meet the requirements of its existing systems. The gateway incorporates those components deemed most likely to remain unchanged. In its default configuration, the gateway orchestrates the processing of messages sent to and received from the NHIN, typically by invoking a sequence of gateway and adapter services.

In general, each component within the gateway is implemented as a deployed web service and/or Java component. Some of these web services and components are exposed externally facing the NHIN, while others are exposed externally facing the adapter. Many web services are exposed only internally to the other gateway components. The interface between the gateway and adapter is decomposed into multiple web services or Java components based on functionality and conforming to the NHIN message specifications. However, web services at the component level inside the gateway and adapter may use separate, simplified formats.

The view of the architecture differs for handling messages from the NHIN versus messages that originate in an organization's existing system and are targeted for delivery to the NHIN. For messages to the NHIN, an existing organization's system is responsible for initiating the message. The triggering event for sending the message is completely controlled by the organization's systems, but the handling and orchestration of the message is primarily under the control of the gateway. For messages from the NHIN, the message is initiated by an external triggering event or system on the NHIN and received by the gateway. Again, orchestration of processing the message is initially under the control of the gateway until processing by the local system is required to store patient data, respond to a request for information, etc.

The gateway supports two mechanisms for bypassing the built-in orchestrated processing of messages normally performed by the gateway. For messages to the NHIN, the gateway supports a pass-through mechanism. Interfaces to some internal components are exposed externally and can therefore be accessed directly by an adapter that wishes to send a message to the NHIN, but manage orchestration itself. In this case, "proxy components" accept information components from the adapter and pass the message on to the NHIN without any significant processing. For messages from the NHIN, the gateway also supports a mechanism for bypassing orchestration. This functionality is implemented using a set of internal components that work together. A message receiver receives the inbound message from the NHIN, and calls the appropriate orchestration component in the default configuration, or passes message components directly to the adapter without orchestration.

Interfaces exposed externally and used by the NHIN to send messages to the gateway include: Patient Discovery to identify matching patients, Document Query and Document Retrieve to locate and access patient information in a query/retrieve exchange pattern, Subscription Management and Notification Processing to manage a publish/subscribe exchange pattern, Document Submission to exchange patient-specific information initiated by the sending organization in a push exchange pattern, Administrative Distribution to exchange non-patient-specific information initiated by the sending organization in a push exchange pattern, Audit Reporting to access audit records for requests and information access, and UDDI Update Manager which receives change notifications from the NHIN UDDI server as part of managing service endpoints.

Interfaces exposed externally by the gateway and facing the adapter include: Patient Correlation to provide access to patient correlations, Patient Discovery, Document Query, Document Retrieve, Subscription Management and Notification Processing, Document Submission, Administrative Distribution, Audit Reporting, and "Pass Through" implemented as a set of interfaces that provide access to the pass-through mechanism that bypasses orchestration.

Definitions

As used herein, the term "Active Test" refers to a set of test groups being executed by a Participant.

The term "Attachment" may refer to a log or other file attached to a test group for manual verification.

The term "certificate authority" or "certification authority" (CA) refers to an entity that issues digital certificates. The digital certificate certifies the ownership of a public key by the named subject of the certificate. This allows others (relying parties) to rely upon signatures or assertions made by the private key that corresponds to the public key that is certified. In this model of trust relationships, a CA is a trusted third party that is trusted by both the subject (owner) of the certificate and the party relying upon the certificate.

The Apache Software Foundation (ASF) is a decentralized community of developers, which produce software distributed under the terms of the Apache License and is free and open source software (FOSS). The Apache projects are characterized by a collaborative, consensus-based development process and an open and pragmatic software license. Each project is managed by a self-selected team of technical experts who are active contributors to the project. The ASF is a meritocracy, whereby membership to the foundation is typically granted only to volunteers who have actively contributed to Apache projects. The ASF is considered a second generation open-source organization.

The term "architecture" is used in a variety of contexts to describe an orderly arrangement of parts. In the architecture of a network, the components include generally subsystems and interfaces. For example, in the architecture of the Internet, the subsystems are clients and servers. The Internet architecture may be viewed as similar to "city planning" in that it attempts to govern best by governing least. By defining a few general subsystems and focusing primarily on the interfaces, it balances the conflicting goals of coordinating disparate elements and providing flexibility for innovation.

A Closed Test or Previous Test refers to any of the sets of test groups that are no longer active, whereby the participant has stopped executing that set of test groups.

CONNECT refers to an open source software solution that supports health information exchange—both locally and at the national level. CONNECT uses NHIN standards and governance to ensure health information exchanges are compatible with other exchanges being set up throughout the country. This software solution was initially developed by federal agencies to support their health-related missions, but it is now available to all organizations and can be used to help set up health information exchanges and share data using nationally-recognized interoperability standards.

A Cross Gateway Query sends a query from one community to another to identify the location of healthcare information satisfying specific constraints. A Cross Gateway Retrieve requests the retrieval of a specific set of healthcare information (a document or documents) from another community.

The term "decoupling" is used to identify the separation of software blocks that shouldn't depend on each other. Some building blocks are generic and shouldn't know details of others. Special design techniques allow software designers to have as few dependencies as possible. This typically reduces the risk of malfunction in one part of a system when the other part is changed. It also forces the developer to focus on one thing at a time.

The DIL Test Platform (or DIL or Test Lab or Lab) refers to a set of self-service testing tools and processes used to conduct gateway to gateway testing. This includes a test harness or automated test framework, which is a collection of software and test data configured to test a program unit by running it under varying conditions and monitoring its behavior and outputs. Test harnesses allow for the automation of tests. They can call functions with supplied parameters and print out and compare the results to the desired value. A test harness should allow specific tests to run (to help in optimization), orchestrate a runtime environment, and provide a capability to analyze results.

Eclipse is an open-source community that develops open platforms and products. The community projects focus on building an open development platform consisting of extensible frameworks, tools and runtimes for building, deploying and managing software across the lifecycle. The Eclipse Foundation is a non-profit corporation which acts as the steward of the Eclipse community.

Enterprise service bus (ESB) is a software architecture model used for designing and implementing the interaction and communication between mutually interacting software applications in Service Oriented Architecture (SOA). As a software architecture model for distributed computing, it is a specialty variant of the more general client server software architecture model and promotes strictly asynchronous message oriented design for communication and interaction between applications. Its primary use is in Enterprise Application Integration of heterogeneous and complex landscapes.

A "gateway" is a network point that acts as an entrance to another network. On the Internet, a node or stopping point can be either a gateway node or a host (end-point) node. Both the computers of Internet users and the computers that serve pages to users are host nodes.

Event Gateways fall into one of two categories: Request Gateways, or gateways sending a request message, are those that trigger an execution; Responder Gateways, or gateways that receive a request message and subsequently send a response message, are those where event execution is triggered by an external event.

GlassFish is an open-source application server project started by Sun Microsystems for the Java EE platform and now sponsored by Oracle Corporation. The supported version is called Oracle GlassFish Server. GlassFish is free software, dual-licensed under two free software licences: the Common Development and Distribution License (CDDL) and the GNU General Public License (GPL) with the classpath exception. GlassFish supports all Java EE API specifications (by definition since it is the Java EE Reference implementation), such as JDBC, RMI, e-mail, JMS, web services, XML, etc., and defines how to coordinate them. Java EE also features some specifications unique to Java EE for components. These include Enterprise JavaBeans, Connectors, servlets, portlets (following the Java Portlet specification), JavaServer Pages and several web service technologies. This allows developers to create enterprise applications that are portable and scalable, and that integrate with legacy technologies.

An Initiating Gateway initiates an inter-community communication across the NHIN.

Java refers to several computer software products and specifications from Oracle Corporation, that together provide a system for developing application software and deploying it in a cross-platform environment. Java is used in a wide variety of computing platforms from embedded devices and mobile phones on the low end, to enterprise servers and supercomputers on the high end. While less common on desktop computers, Java applets are sometimes used to provide improved and secure functions while browsing the World Wide Web.

Maven is a build automation tool typically used for Java projects. Maven serves a similar purpose to the Apache Ant tool, but it is based on different concepts and works in a different manner. It can be used to build and manage projects written in C#, Ruby, Scala, and other languages. Maven is hosted by the Apache Software Foundation. Maven uses an XML file to describe the software project being built, its dependencies on other external modules and components, the build order, directories, and required plug-ins. It comes with pre-defined targets for performing certain well-defined tasks such as compilation of code and its packaging.

The Nation Wide Health Information Exchange (NwHIN or NHIN or the Exchange) relates to methods to perform universal patient lookup, document discovery and retrieval, and exchange between organizations and federal agencies (e.g., VA, DOD, CDC, SSA, etc.). The organizations entering into an exchange with those federal agencies are typically sizable HIOs, HIEs or large IDNs. Participation in the NHIN is currently limited to federal health agencies and healthcare organizations under ONC contract and other recipients of federal grants. There are technical teams devoted to the on-boarding process (validation and conformance testing), security, authentication, and adherence to the specifications/standards, including producing/accepting structured data in defined formats.

N-tier application architecture provides a model for developers to create a flexible and reusable application. By breaking up an application into tiers, developers may modify or add a specific layer, rather than rewrite the entire application, such as if technologies change or scale up. In the term "N-tier," "N" may refer to any number (e.g., 2-tier, 4-tier, etc.). Thus, N-tier may refer to any number of distinct tiers utilized in the architecture. Application architectures are part of Layer 7 of the OSI model.

A Participant is an organization, candidate, or entity that has developed a technical solution (gateway) it wishes to test to exchange data. A Participant System refers to the Participant's technical solution, which the Participant is operating and using to test gateway connectivity.

Reference Implementation is, in general, an implementation of a specification to be used as a definitive interpretation for that specification. During the development of the conformance test suite, at least one relatively trusted implementation of each interface is necessary to: (1) discover errors or ambiguities in the specification; and (2) validate the correct functioning of the test suite. Characteristics of a Reference Implementation include: (1) concurrent development with spec and test suite; (2) verifies that specification is implementable; (3) enables the test suite to be tested; (4) serves as Gold Standard against which other implementations can be measured; (5) helps to clarify intent of specification where conformance tests are inadequate.

A Responding Gateway refers to participation in an inter-community communication in the DIL initiated by another gateway.

Service-Oriented Architecture (SOA) refers to a set of principles and methodologies for designing and developing software in the form of interoperable services. These services are well-defined business functionalities that are built as software components (discrete pieces of code and/or data structures) that can be reused for different purposes. SOA design principles are used during the phases of systems development and integration. A SOA Gateway seamlessly controls access to services, protects information through data-level encryption, ensures the integrity of a message through signatures, and controls corporate information flow.

A Simple Object Access Protocol (SOAP) is a protocol specification for exchanging structured information in the implementation of Web Services in computer networks. It relies on Extensible Markup Language (XML) for its message format, and usually relies on other application layer protocols, most notably Hypertext Transfer Protocol (HTTP) and Simple Mail Transfer Protocol (SMTP), for message negotiation and transmission. SOAP can form the foundation layer of a web services protocol stack, providing a basic messaging framework upon which web services can be built. This XML based protocol consists of three parts: an envelope, which defines what is in the message and how to process it; a set of encoding rules for expressing instances of application-defined datatypes; and a convention for representing procedure calls and responses. SOAP has three major characteristics: Extensibility (security and WS-routing are among the extensions under development), Neutrality (SOAP can be used over any transport protocol such as HTTP, SMTP or even TCP), and Independence (SOAP allows for any programming model).

A Test Case refers to a path through the DIL to test communications. The Test Case includes a set of test inputs, execution conditions, and expected results, identified for the purpose of making an evaluation of a participant's ability to test gateway communication.

Test Data refers to a set(s) of anonymous data (e.g., patient data). The DIL provides Test Data to test gateway communications.

Test harness or automated test framework refers to a collection of software and test data configured to test a program unit by running it under varying conditions and monitoring its behavior and outputs. It has two main parts: the Test execution engine and the Test script repository. Test harnesses allow for the automation of tests. They can call functions with supplied parameters and print out and compare the results to the desired value. The test harness is a hook to the developed code, which can be tested using an automation framework. A test harness should allow specific tests to run (this helps in optimizing), orchestrate a runtime environment, and provide a capability to analyze results. The typical objectives of a test harness are to: Automate the testing process, Execute test suites of test cases, Generate associated test reports.

Within the DIL, Test Results refers to a set of runs of test groups and test cases for a participant, including any attached evidence. The DIL assigns each set of test results a unique execution identification. Each participant may have one set of active test results and may retain previous sets of test results.

A User refers to a Participant Test Lead or individual conducting testing on behalf of the Participant.

VisualSVNs is a Subversion (SVN) client, implemented as an add-in for Microsoft Visual Studio, that provides an interface to perform the most common revision control operations directly from inside the Visual Studio IDE. Visual SVN is a commercial program using Tortoise SVN to execute the Subversion commands.

Environment and Functionality

The DIL allows for gateway to gateway testing. The DIL uses event based gateways with initiator and responder scenarios, ensuring candidates possess the ability to communicate with other gateways. In one implementation, the DIL utilizes a shared architecture (services, standards, and requirements) to interconnect health information exchanges and the supported participants or users. As healthcare messaging specifications evolve, the need for a test lab that can easily support multiple gateways utilizing a Service-Oriented Architecture (SOA) has arisen.

The DIL incorporates architectural improvements, such as the SOA implementation, which was developed to stream line the maintenance of multiple gateways, reducing complexity of the architecture and enhancing usability. In one embodiment, the DIL is based on an SOA design, though it may also support customized versions of the CONNECT 2.4.8 and CONNECT 3.2 gateways. When other gateways interact with the DIL, customization may be required. The intent of the DIL architecture is to support numerous gateway types and versions, avoiding customization of code altogether. The success of an SOA deployment is measured by the level of reuse of the producer services (e.g., gateways). A well thought out SOA is flexible, loosely coupled, and enables applications to rapidly integrate with published producer services.

The DIL environment is divided into three major functional areas: ESB Components, Gateway Agents, and Web Applications. ESB components provide an integration platform using SOA architecture to support executing various testing scenarios against multiple versions and implementations of NHIN Gateways (e.g., CONNECT, Axolotl, EPIC, etc). Gateway Agents provide a non-intrusive mechanism to intercept the cross gateway messages between NHIN Gateways, thus providing an opportunity to capture and analyze the test case execution results. Web Applications provide a centralized user interface for clients to create, manage, and execute various test scenarios and validate the test results.

The role of a gateway agent in the SOA based Lab provides bi-directional transaction scenarios on how it would interact with other components in the lab. The gateway agent concept allows for the eliminations of customizations to a gateway product as well as the web service stack in place for the purpose of extracting cross gateway messages.

Figure 2:
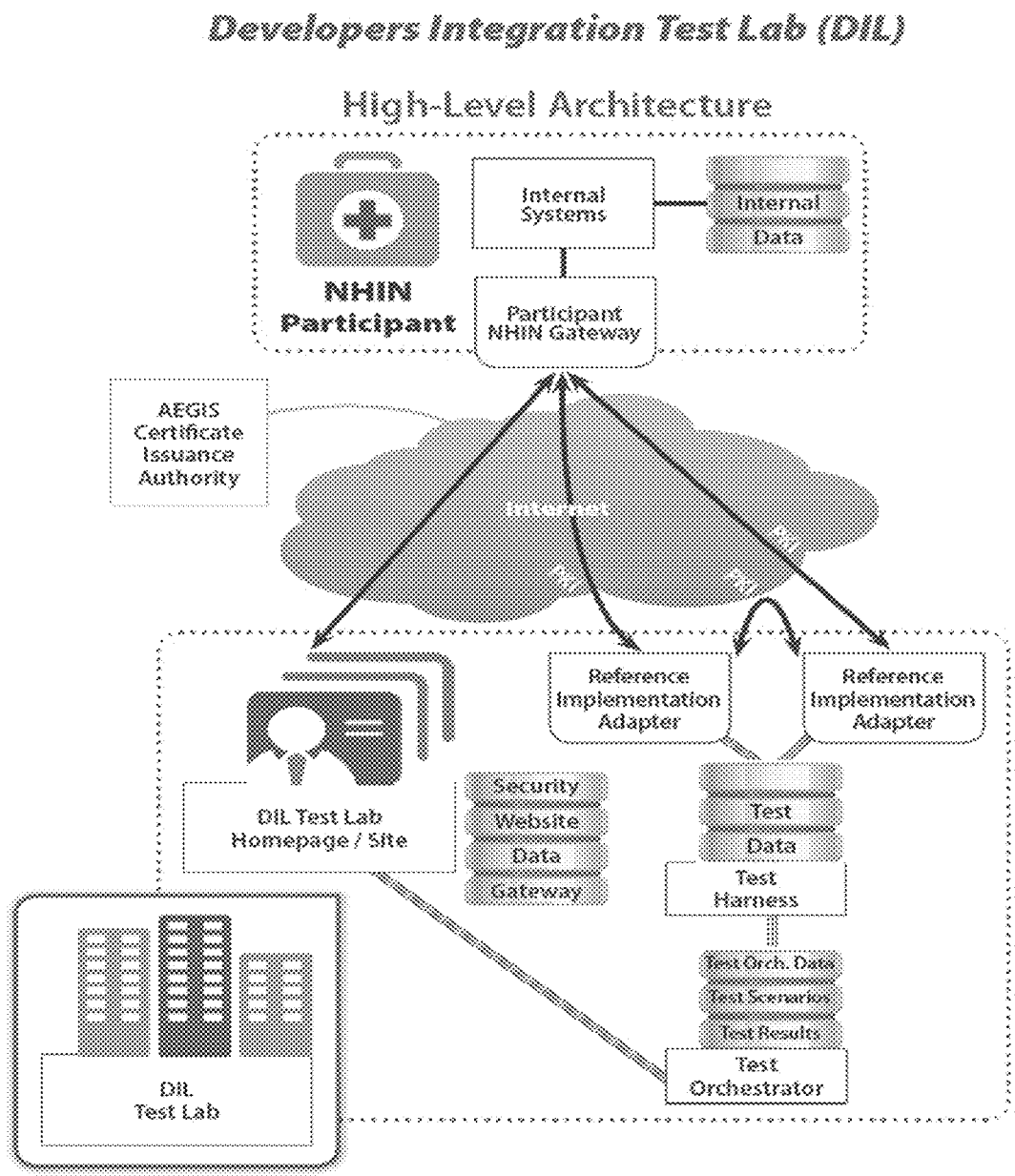
FIG. 2 illustrates a schematic diagram of architecture of the DIL according to another embodiment of the present invention.
Figure 2A:
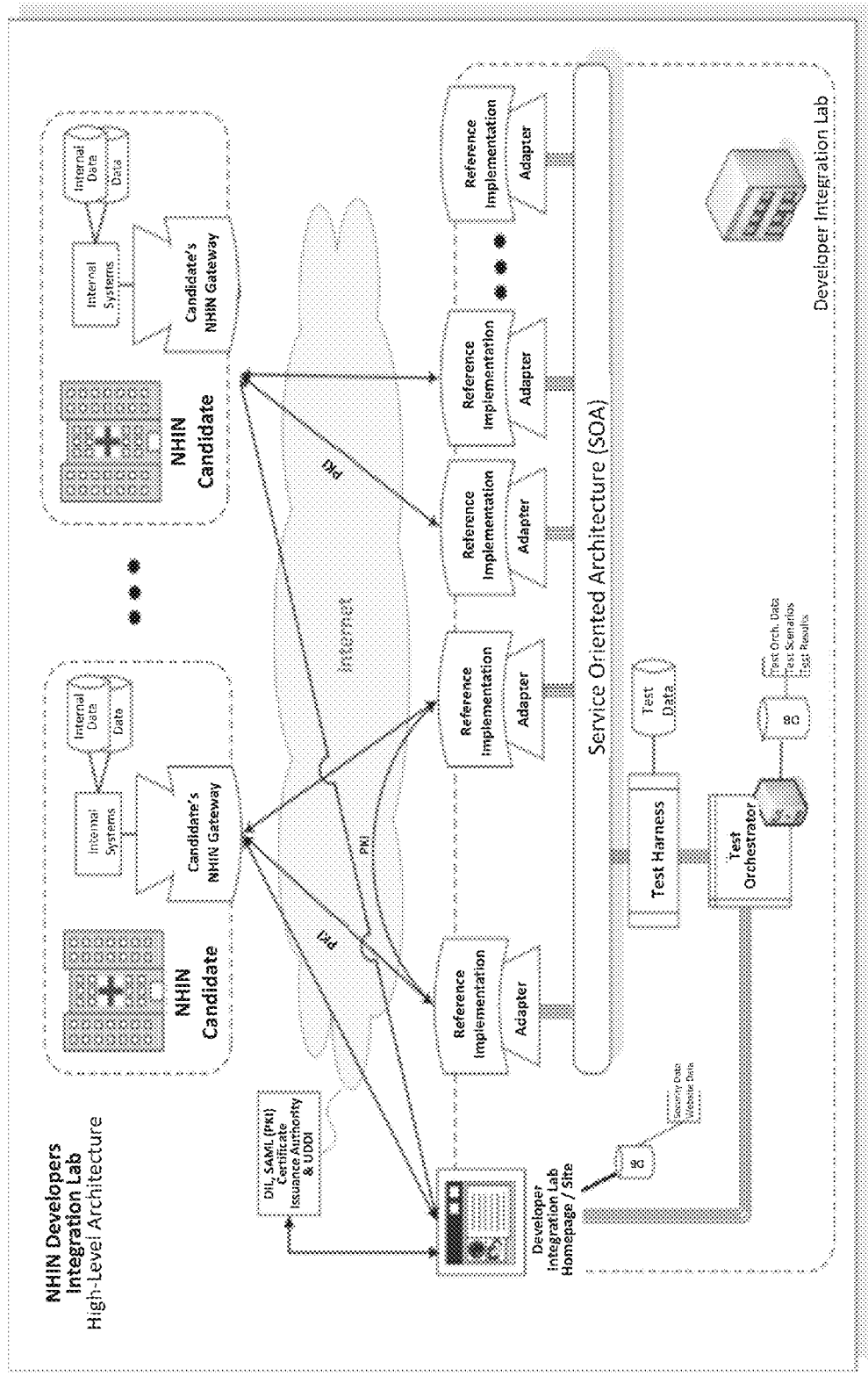
FIG. 2A illustrates a schematic diagram of architecture of the DIL according to another embodiment.

Referring to FIGS. 2 and 2A, schematic diagrams of architectures of the DIL according to embodiments of the present invention are illustrated. The main driving component behind the SOA, FUSE Source is an open Services Message Integration Services to explain the architecture principles behind the modernization of the test harness. Representations and descriptions of the architecture from both the 'initiator' and 'responder' scenarios are provided.

In one embodiment, the DIL utilizes the following test scripts: Patient Discovery (PD), Query for Documents (QD) and Retrieve Documents (RD). These test scripts represent various services a gateway or endpoint may be qualified to perform. In other embodiments, the DIL may include additional services (Test User Interface templates) to allow for on line test script creation.

FuseSource may be selected to support the development and maintenance of the DIL SOA modernization. FuseSource includes a set of open source integration and messaging tools with standards-based, enterprise products based on popular Apache projects. The FuseSource products include four open source components: Fuse ESB, Fuse Message Broker, Fuse Services Framework and Fuse Mediation Router. These four components are integrated with development and management tools, creating a comprehensive enterprise integration infrastructure deployed in many large and mission-critical IT applications.

Fuse ESB has a 'pluggable' architecture, which allows organizations to use a variety of services solutions. The Enterprise Service Bus (ESB) is a software infrastructure facilitating application integration. An ESB is valuable to the implementation of a SOA due to its ability to exchange messages, execute transactions, orchestrate services, and perform, publish and subscribe functions between disparate and distributed applications.

One component of Fuse is Apache Active MQ. The DIL can contain asynchronous initiation submissions for different test cases and test scenarios with respect to different vendor specific gateways (CONNECT, Axolotl, etc.). This permits user flexibility for submitting multiple initiations from the DIL loosely coupled with both the test lab and test lab processor components. The Test Case processor executes the initiation message which is loosely coupled to any of the gateway servers using SOA Adapters and Web services.

Figure 3:
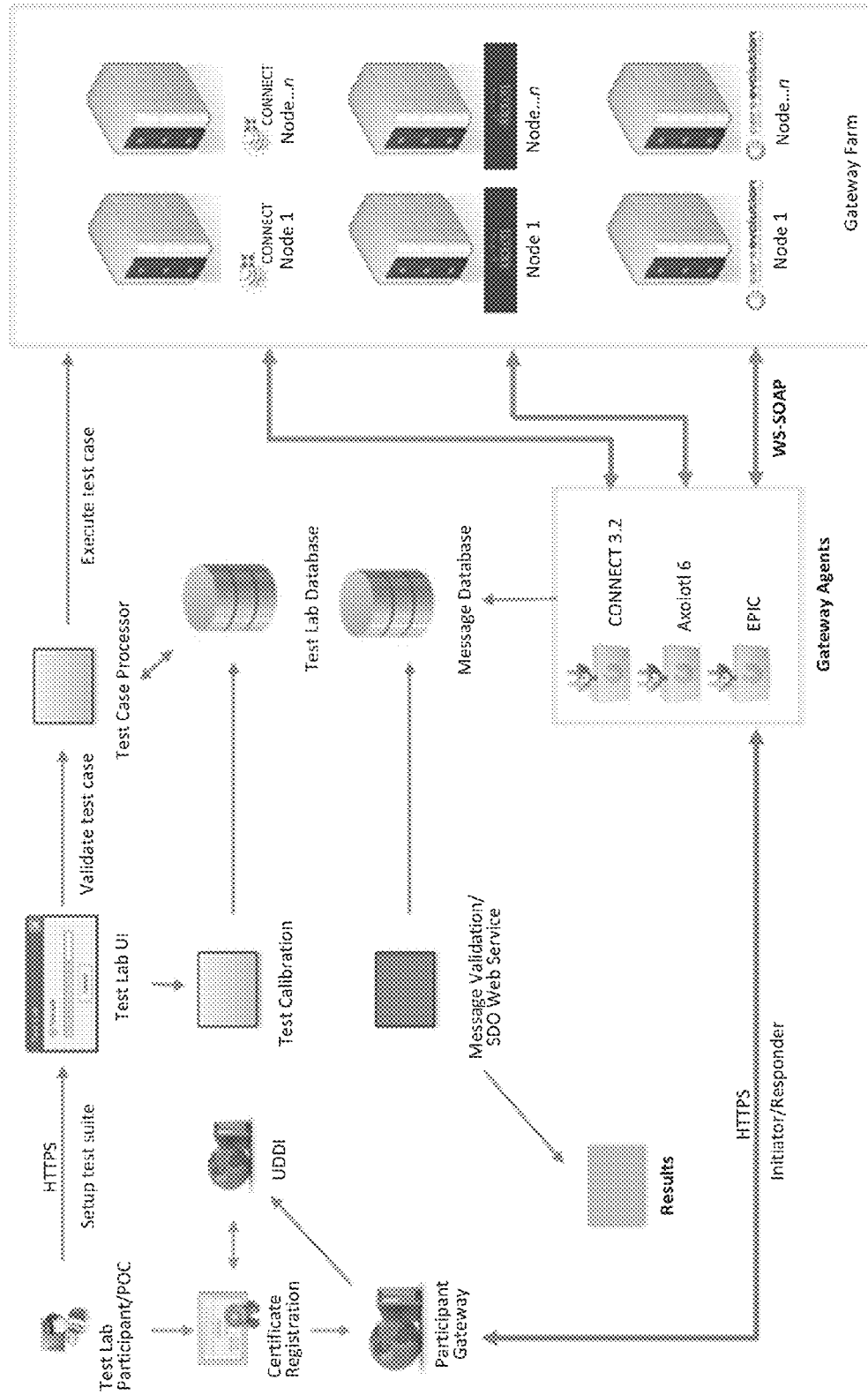
FIG. 3 illustrates a schematic diagram of the SOA Gateway enabled DIL according to an embodiment of the present invention.

Referring to FIG. 3, a schematic diagram of the SOA Gateway enabled DIL is illustrated. The view for the DIL user will be the same as the focus of this architecture is on decoupling the dependencies between components of the architecture. Implementation of the architecture provides increased flexibility to participants, enabling them to exchange messages using numerous gateway types and versions. By utilizing a low coupling strategy, greater flexibility is provided. Further, required customizations developed for a gateway product is eliminated, as well as the web service stack currently in place.

The DIL architecture may include the following components:

Test Case Processor: The Test Case Processor handles responder scenarios. Responder scenarios may be captured as test cases, scenarios (group of test cases) or as a test suite (group of scenarios). Responder scenarios are routed to the Test Case Processor. The Test Case Processor determines how the initiation (PD, QD, RD) is built. For example, when a building a PD initiation, the processor will generate information on the patient and the node location for that patient within the gateway farm. The processor then builds the request message and assigns it to a node. Participants can select the specific gateways from the lab UI.

Test Lab Database: The test lab database is the repository for all test cases. It includes static and dynamic test case information, test cases being processed, results of the test cases processed, and audit information. Static test cases are test cases built already into the system. Dynamic Test Cases are Test Cases the user can create manually within the DIL. Dynamic Test Cases are described within the document (e.g., DynamicTestCases.docx).

Gateway Agent: The Gateway Agent is a bidirectional gateway adapter, allowing users to intercept messages being exchanged from either the initiator or responder scenarios. The messages are then stored within the message database. The primary function of the gateway agent is to receive and deliver the message to the intended recipient.

Test Calibration: Test Calibration measures the capacity of each gateway, monitoring the number of messages entering and leaving the gateways. This component is mainly used for performance testing.

Message Validation/Service Data Objects (SDOs) Webservice: The message validation/Service Data Objects (SDOs) webservice handles the external service calls to external parties, e.g. a federal agency, such as NIST. This component is used to validate the incoming/outgoing messages being intercepted and stored in the message database. The validation results are presented as web service calls to the external world. External web calls will result in a reporting function published within the green box named 'Results'. The SDOs simplify and unify SOA external calls. The SDO will also provide a convenient method to work with XML documents.

Figure 4:
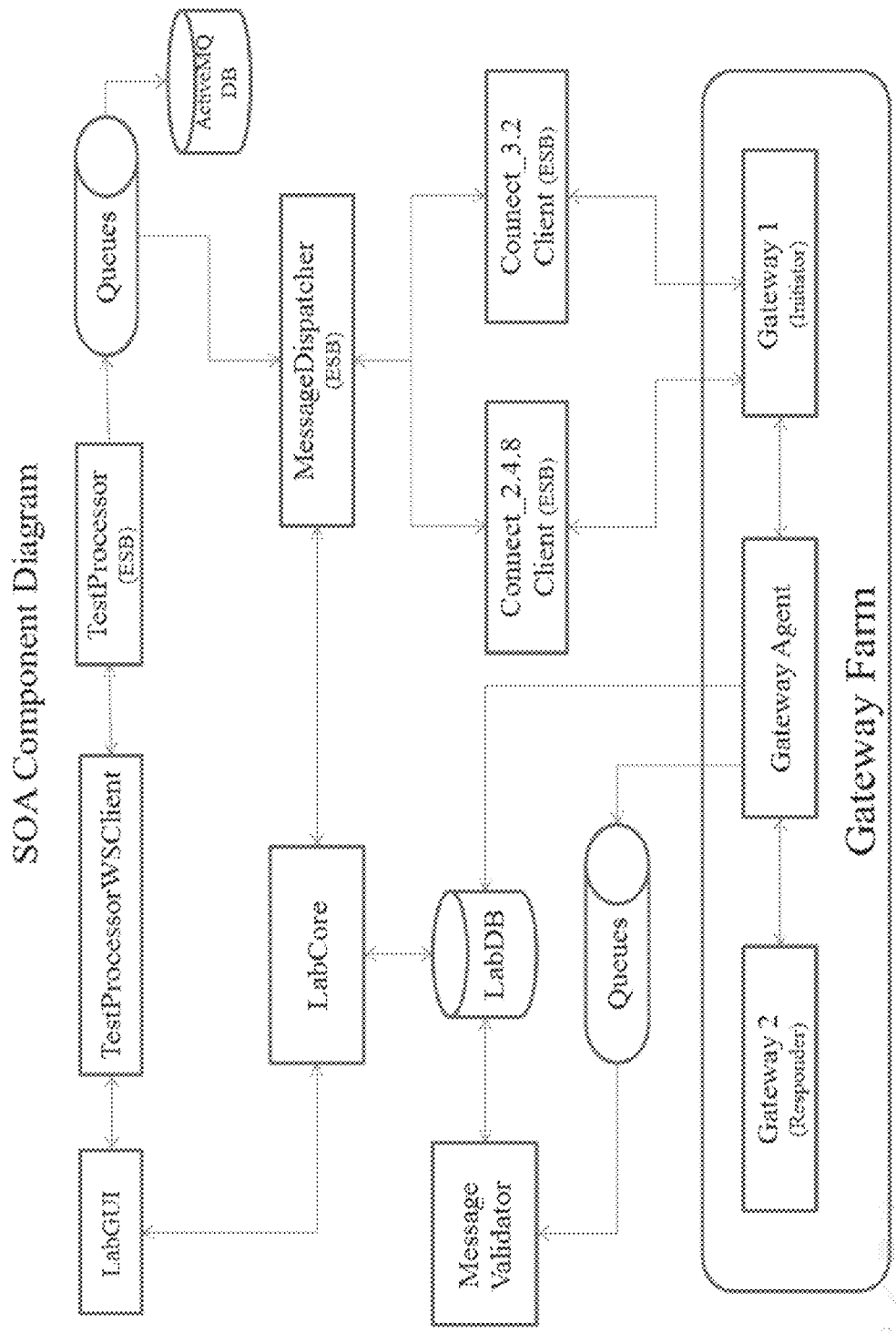
FIG. 4 illustrates a schematic diagram of various SOA components that interact within, and externally to, the Fuse ESB layer according to an embodiment of the present invention.

Referring to FIG. 4, a schematic diagram of various SOA components that interact within, and externally to, the Fuse ESB layer is illustrated. The many interactions, listeners, and the backend database functionality within the context of the SOA architecture is depicted. The client interacts with the Lab GUI to execute a service case against a specific Gateway. When a service case is executed, the information is sent to the Test Processor WS Client and is then sent to the Test Processor. The Test Processor validates the message that was sent to it from the TestProcessorWSClient.

If the TestProcessor determines the message is invalid, an error message is sent to the user. However, if the TestProcessor determines the message is valid, the message will then go into the Queue and wait to be distributed to the specified message dispatcher depending on the gateway credentials. The queue works in a 'first come, first serve' basis (i.e., the time the message enters the queue will determine what place in line the message will be before it is turned over to the message dispatcher).

The MySQL database is used in the Active MQ. No other components use this database directly. Active MQ maintains and stores messages in the DB and subsequently puts the message into the Queue.

As the message goes to the specified Message Dispatcher, a Listener records the information and the actions being taken on the message. The execution ID of the message, describing the test case being processed, is communicated to the Lab DB to allow the processor to determine the type of test being performed against the gateway. The Lab DB also holds all dates, supporting tables for the Lab GUI in regards to the participant and patient information. Entity Gateway and Cross Gateway initiation messages are generated within CONNECT 2.4.8 and 3.2 clients in the first iteration of the architecture modernization. These clients determine the requestor and responder information from the Lab Core, and subsequently the requesting gateway begins communicating with the responding gateway.

The Gateway Agent initiates the gateway and sends initiation messages to the target/responding gateway. The gateway agent captures both the message and the corresponding response. The Interceptor captures the request and response messages sent between the gateways. The Message Validator component reads the messages and validates the IDs and the test case associated with the message, updating the case state of the corresponding test case.

Figure 5:
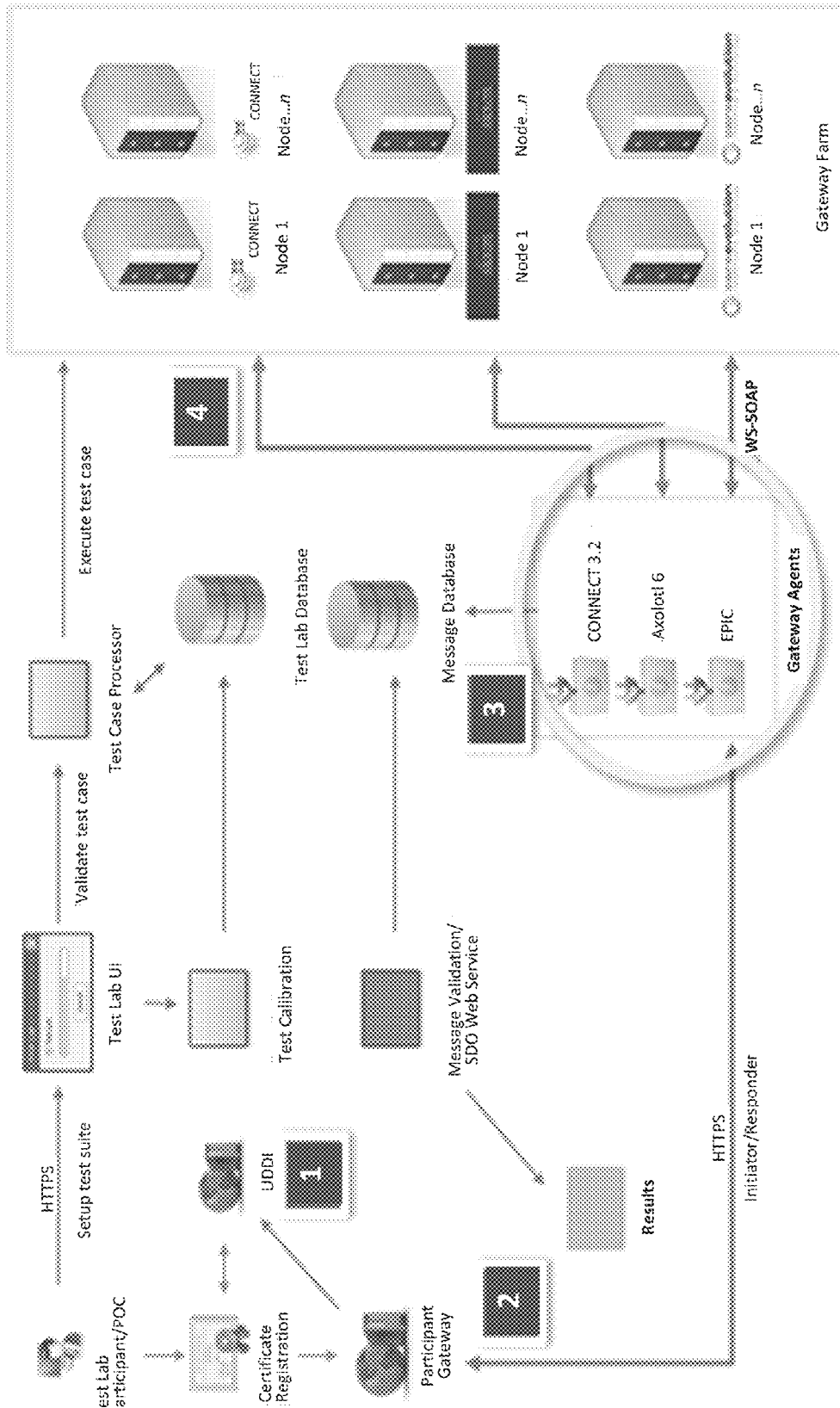
FIG. 5 illustrates a schematic diagram of the DIL Requestor Architecture according to an embodiment of the present invention.

Referring to FIG. 5, if the Applicant's system is the Requestor, the following steps will take place: 1) Identify the system that contains the requesting gateway through the test case description in the Test Lab UI. 2) Initiate the corresponding cross gateway exchange from the system under test. 3) The Gateway Agent takes on the role of an interceptor, intercepting the message sent from the requesting gateway. Based on the type of message intercepted, the agent delivers it to the corresponding SOA gateway adapter hosted by the FUSE ESB container. The Gateway Agent is a bidirectional component, intercepting messages and storing details within the message database. 4) The message database is used for auditing and test case results.

Unlike the Responder scenario, the test case results cannot be viewed immediately. The user needs to allow two to three minutes for the Exchange Lab GUI to refresh and display the status of the test case. This is because the audited message needed to be processed to display the result. Message Validation validates the messages being exchanged and stored within a message database. This message validator validates the message and prepares the result. These results can be retrieved as service calls to the external world.

Figure 6:
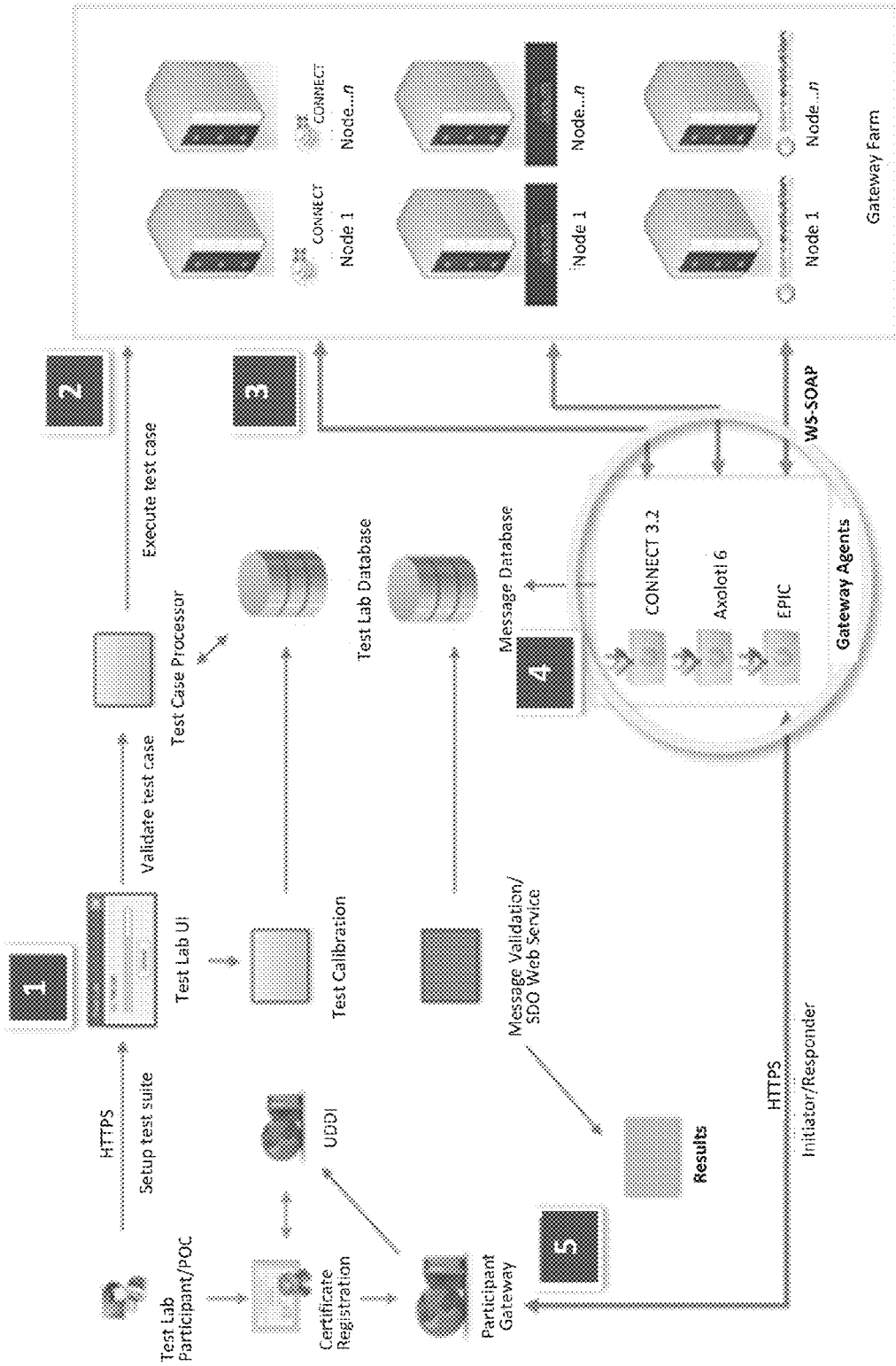
FIG. 6 illustrates a schematic diagram of the DIL Responder Architecture according to an embodiment of the present invention.

Referring to FIG. 6, if the Applicant's system is the Responder, the following steps will take place: 1) The Participant/User sets up the test suite in the Test Lab to run the scenarios. The Participant/User can create test cases using the existing test cases (static test cases). This step is carried out by the HTTPS setup Test Suite with the help of Test Lab UI in the diagram. Test Case validation has been performed prior to the test case submission to the Test Case Processor. 2) As described, the Test Case Processor component is based on SOA, routing the messages based on the node and the type of gateway it wants to communicate to, such as CONNECT, EPIC, etc. This component is hosted by Fuse ESB to specifically obtain SOA support. The Test Lab UI captures information such as the gateway version, the requesting gateway submitted, and other important elements. Based on the version with which the participant wants to test their gateway or exchange messages, an initiation message is submitted to the corresponding queue with that particular gateway adapter chosen (i.e. CONNECT 2.4.8, CONNECT 3.2, etc.) and the corresponding test case executed. The gateway adapters are also hosted by the Fuse ESB container. 3) The Test Lab Database is a repository containing all static and dynamic test cases using templates and supporting data to run the test lab. The Test Case Processor invokes the Test Lab database to select the queue, writing test case execution results to reflect in the Test Lab UI, and audit information. 4) With the help of Test Calibration, the Test Lab posts results of various gateway performance related parameters. 5) For a Responder Scenario, the results will be available immediately following the completion of test case execution.

DIL Multi-Tiered Architecture

Figure 7:
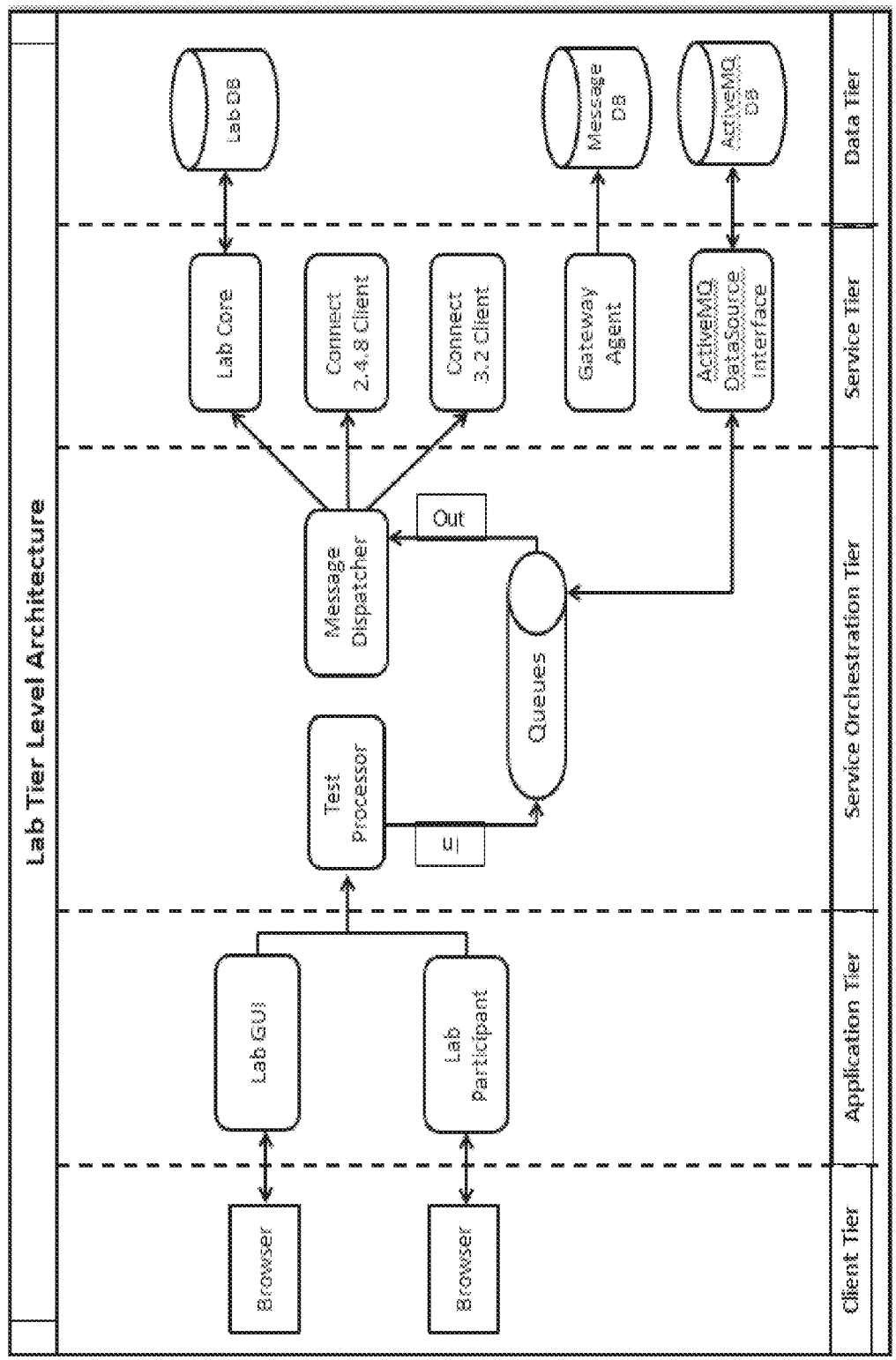
FIG. 7 illustrates a schematic diagram of the DIL architecture separated into five tiers according to a disclosed embodiment.

The new SOA gateway DIL adopts a scalable application architecture (over two-tier and three-tier). A multi-tiered architecture is used when the architecture contains four or more tiers/levels within its architecture. Such architecture promotes de-coupling and performance optimization. An embodiment of the architecture separated into five tiers is shown in FIG. 7. The five tiers include: Client, Application, Service Orchestration Tier, Service Tier and Data Tier.

EXAMPLE 1

DIL Request/Response Messages

Cross gateway SOAP messages are classified as either a request or response message interacting within an Initiator or Responder scenario. An initiator scenario tests the candidate's gateway request functionality; the candidate sends a request message to the DIL gateway which subsequently sends a response message. The responder scenario tests the candidate's gateway response functionality; the DIL gateway sends a request message to the candidate that in turn receives the request message and sends a response message. Both request and response messages must follow the HL7 specifications.

The various elements which make up the request/response SOAP messages may include:

Key XML Message Elements

Utilizing sample request/response XML message data from a Patient Discovery (PD) service, the purpose of this section is to identify, within the XML code, important elements and their interactions within a request message. Values and elements with elevated importance are underlined. The Certificate token is the only element found in both request and response messages.

Certificate Token:

```
Value="DB0+uH5ClADKVjzsF5UOM9wa0hEpQE9jUC7H2MvnJbogWFcywaQA2
3uBIy/YSMzd4QwOQnSV15ArGbF2exuwqzexBLh6Sf/C7Ub7R1B26w6WgVa4I8p
2kkPQV/eutH49Rgd+ocRsItcI0k3nk8JD8r76nmPSAt82ii6EU038znYU/b+QPk1gOB
c1LPWIZh3H98T95koGIXCn/2Qwws6QpbN2i5/04+nxeXUkhKmvrQEiRVW6zfBr
+GrMfpQKm37pw0tqIln4a2uTGtZUdi8iun9pf8Ur3TeyLFjmF4L/FRtpMTbO2loBeP
iLYN/OCPyb73zGz951I/FJAzDP/1E5WQ==" />
```

The certificate token value, found in both request and response XML messages, allows for the 'handshake' to occur between the requesting and responding gateways. In order for a handshake to properly occur, the responding gateway must accept the certificate token that is sent to it from the initiating gateway. The certificate token includes information on the organization sending the message. The responding gateway is able to identify the organization sending the messaging and may decide to accept or reject the message.

Key Elements of the Sample Request PD Message:

Request Message Identifier:

```
<S:Body>
<PRPA_IN201305UV02 xmlns="urn:hl7-org:v3"
xmlns:ns2="urn:gov:hhs:fha:nhinc:common:nhinccommon"
xmlns:ns3="http://schemas.xmlsoap.org/ws/2004/08/addressing"
xmlns:ns4="urn:gov:hhs:fha:nhinc:common:patientcorrelationfacade"
ITSVersion="XML_1.0">
```

This identifier displays the type of message being sent between gateways. Request and response messages pass similar fields amongst one another (i.e. livingSubjectName, streetAddressLine); the message identifier determines what message, either a request or response, is currently being passed. The value 305 within the value IN201305UV02, denotes a request message type is being sent. Subsequently, the value 306 denotes a response message type.

queryByParameter Element:

```
<queryByParameter><queryId extension="-abd3453dcd24wkkks545"
root="2.16.840.1.113883.0.102"/><statusCode
code="new"/><responseModalityCode code="R"/><responsePriorityCode code="I"/>
```

The queryByParameter element sends the request to the gateway for patient information.

SOAP Message Following HL7 Specs:

```
<parameterList><livingSubjectAdministrativeGender><value
code="F"/><semanticsText
representation="TXT"/></livingSubjectAdministrativeGender><livingSubjectBirthTi
me><value value="19400807"/><semanticsText
representation="TXT"/></livingSubjectBirthTime><livingSubjectId><value
extension="RI2.102.00008"root="2.16.840.1.113883.0.102"/><semanticsText
representation="TXT"/></livingSubjectId><livingSubjectId><value
extension="666660008" root="2.16.840.1.113883.4.1"/><semanticsText
representation="TXT"/></livingSubjectId><livingSubjectName><value><family
partType="FAM">Fleming</family><given
partType="GIV">Jennifer</given></value><semanticsText
representation="TXT"/></livingSubjectName><patientAddress><value><streetAddre
ssLine>4000 Minor
St</streetAddressLine><city>Phoenix</city><state>AZ</state><postalCode>85001<
/postalCode></value></patientAddress><patientTelecom><value value="tel:+1-408-
454-9800"/><semanticsText
representation="TXT"/></patientTelecom></parameterList></queryByParameter></c
ontrolActProcess>
```

The above SOAP message contains embedded HL7 parameters such as 'livingSubjectId' or 'livingSubjectAdministrativeGender'. These various parameters represent the Patient Demographics, or specific patient information.

Key Elements of the Sample Responder PD Message
Responding Message Identifier:

```
<S:Body>
<PRPA_IN201306UV02 xmlns="urn:hl7-ore:v3"
xmlns:ns2="urn:gov:hhs:fha:nhinc:common:nhinccommon"
xmlns:ns3="http://schemas.xmlsoap.org/ws/2004/08/addressing"
xmlns:ns4="urn:gov:hhs:fha:nhinc:common:patientcorrelationfacade"
ITSVersion="XML_1.0">
<id extension="7588e4d5:133fa2fc035:-7f76" root="2.16.840.1.113883.0.207"/>
```

The responding message identifier, much like the request message identifier, categorizes and identifies the type of message being sent. Both message schemes contain much of the similar information and fields; the identifiers are used to determine if the message originated from an initiating or responding gateway. The number '305' is used to denote an initiating scenario for these messages. However, '306' within the above identifier is used to identify the responding message.

HCID:
<value    extension="RI2.102.00008" root="2.16.840.1.113883.0.102"/>

Home Community Identifier (HCID) documented within the XML scheme. The HCID is built within both the request and the responder messages, and is used to help identify the organization which the message is originating from.

Validation: Request/Response Message

EXAMPLE 2

SOA DIL Installation

Figure 8:
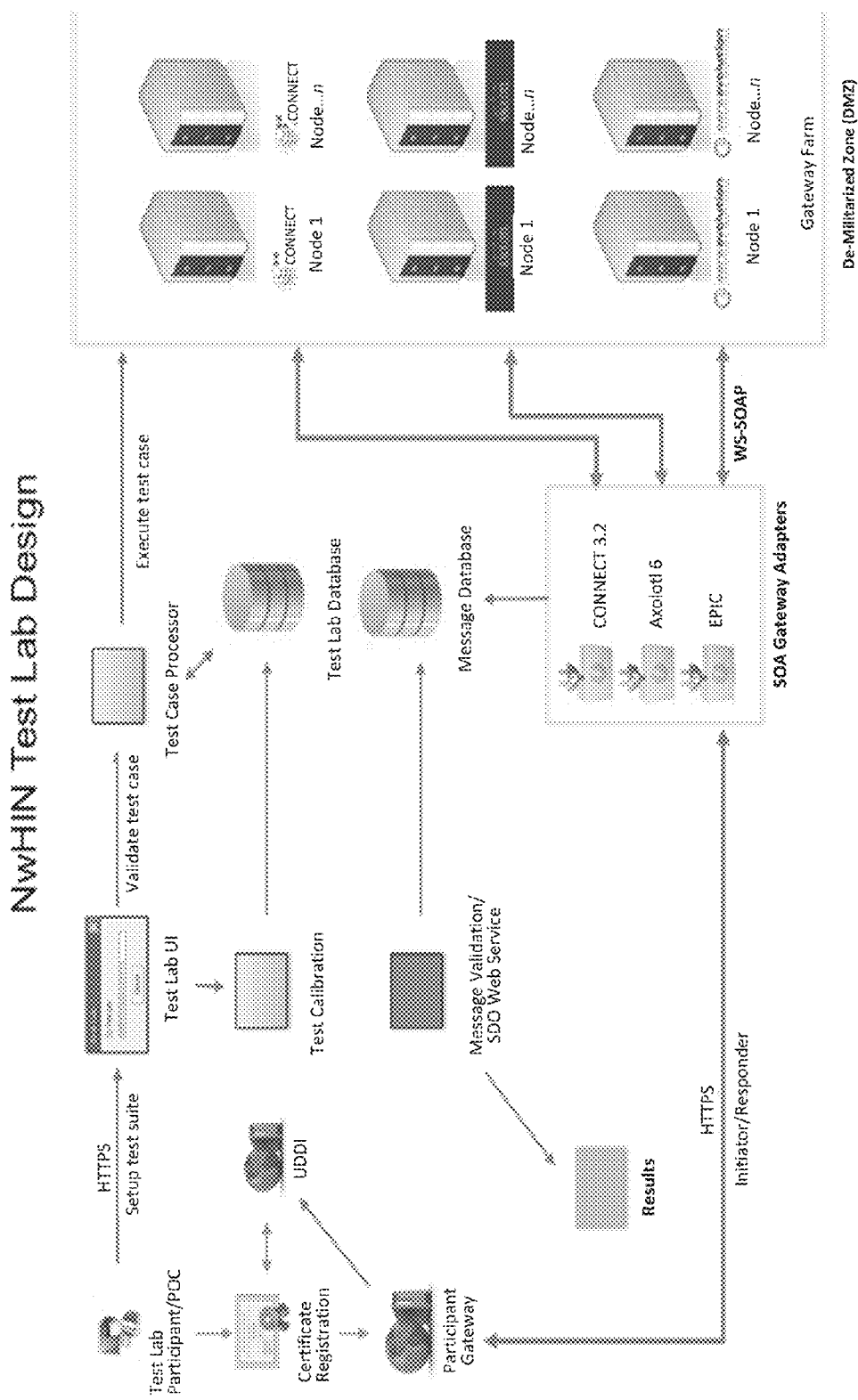
FIG. 8 illustrates a schematic diagram of the DIL architecture according to an embodiment of the present invention and showing components of the SOA Test Harness.

An exemplary process for building the software and setting up a lab environment for executing and validating system test cases against CONNECT software using a SOA architecture is disclosed. The exemplary installation process is illustrative of the architecture, hardware and software components, as well as steps for installation of the environment. Components of the SOA Test Harness are illustrated in FIG. 8.

The Test Lab may be installed and maintained, and provide developers with an understanding of the following concepts or components: a) a SOA environment for the NHIN test lab; b) the hardware and software infrastructure needed to support the lab; c) the user interface which supports the lab; d) a gateway agent; and e) Software Components, including Java, SVN client, Apache Maven, Eclipse, Apache, SQL Server Database, Fuse ESB, Connect, Glassfish. Exemplary developers for the DIL may include: NwHIN Developers, Participants and Organizations; Developers and System Administrators; and Government Organizations (Onboarding Partners).

As discussed above, the DIL environment is divided into three primary functional areas: ESB Components, Gateway Agents, and Web Applications.

At the heart of the Lab environment, ESB components provide an integration platform using SOA architecture to support executing various testing scenarios against multiple versions and implementations of NHIN Gateways (CONNECT, Axolotl, EPIC etc). Gateway Agents provide a non-intrusive mechanism to intercept the cross gateway messages between NHIN Gateways thus providing an opportunity to capture and analyze the test case execution results. Web Applications Provide a centralized user interface for clients to create, manage, and execute various test scenarios and validate the test results.

Figure 9:
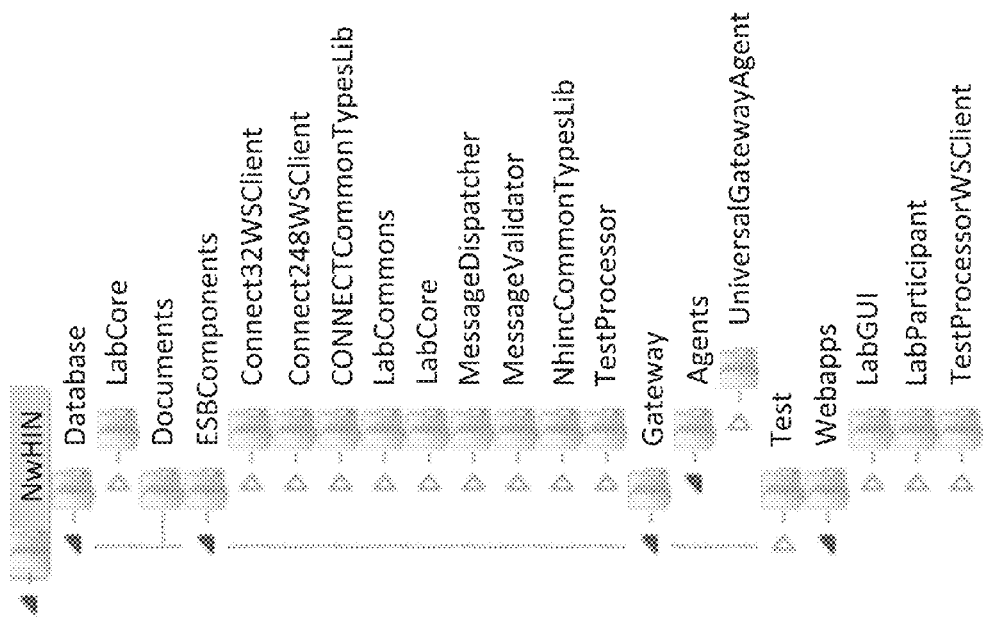
FIG. 9 illustrates a screen view of an exemplary source code project structure of the DIL Lab software.

An exemplary directory structure of DIL Lab software is set forth in Table I below. An exemplary source code project structure is illustrated in FIG. 9.

TABLE I

| Directory | Description |
| --- | --- |
| NwHIN | Parent level project directory |
| ESBComponents | Contains all projects to be deployed to Fuse ESB server as well as common projects used in Fuse ESB and User Interface LabCore and LabCommons are common project for both ESBComponents and WebApps |
| Gateway/Agents | Universal Gateway Agent to capture all cross gateway messages |

TABLE I-continued

| Directory | Description |
| --- | --- |
| WebApps | User interface projects |
| Test | Used for testing ESB projects |
| Database | Contains Lab data base script file, clinical documents for QD, RD testing. |
| Documents | Contains reference documents and configuration files for ESBComponents and the internalConnectionInfo.xml for the Connect Gateway. |

ESB Components

Fuse ESB is an open source, standards based integration platform. It reduces the complexity of integrating disparate applications by leveraging the SOA principles and standardized packaging frameworks. ESB acts as a shared messaging layer for connecting applications and other services and it supplements its core asynchronous messaging backbone with intelligent transformation and routing to ensure messages are passed reliably.

The Lab in SOA environment is the enhanced version on current Test lab. The SOA lab supports the existing functionality with various additional features: 1) Multiple gateway version support; 2) Asynchronous processing; 3) Capturing and validating the actual Inbound/Outbound cross gateway SOAP messages; and 4) Event based test case status updates.

The source code for the ESB Components may include various projects, as shown in Table II.

TABLE II

| Project | Description |
| --- | --- |
| LabCore | DAO & Service component used in other components to access the Lab database. |
| MessageDispatcher | Service component that dispatch the test case parameters to the corresponding client based on the target gateway type. |
| LabCommons | Utility component used by all components. |
| MessageValidator | Service component that validates the Inbound/Outbound messages to determine the pass/fail status for the test case. |
| CONNECTCommonTypesLib | Connect 3.2 Commons library used by Connect32WSClient component |
| NhincCommonTypesLib | Connect 2.4.8 Commons library used by Connect248WSClient component |
| Connect32WSClient | Connect 3.2 web service client. |
| Connect248WSClient | Connect 2.4.8 web service client. |
| TestProcessor | Web Service component used to submit requests from GUI applications to the queues. |

Web Applications (User Interface)

The user interface contains all the Test Scenarios and their associated Test Cases to test an NwHIN Health Information Exchange's (NHIE) ability to interact with other NHIE gateways to exchange healthcare information on consumers. The Test Scenarios are categorized by NwHIN core service functionality. An NHIE must conduct tests as both an initiating gateway and a responding gateway and the interoperability user interface provides a platform for the NHIE participants to register and execute these Test Cases.

The source code for an exemplary User Interface may include the web projects set forth in Table III below.

TABLE III

| Project | Description |
| --- | --- |
| LabGUI | User Interface component for interoperability testing. |

TABLE III-continued

| Project | Description |
| --- | --- |
| LabParticipant | User Interface component used to execute the test cases which is part of active service set. |
| TestProcessorWSClient | TestProcessor webService client used in LabGUI and LabParticipant. |

The concept of a Gateway Agent allows for the complete elimination of customizations to a gateway product as well as the web service stack in place for the purpose of extracting cross gateway messages. A cross gateway transaction may be observed in two fundamental scenarios, namely, the initiator scenario and the responder scenario. The SOA diagrams illustrated in FIGS. 5 and 6 present the workflow steps identified in the sequential order based on the two types of scenarios. The initiator or Requestor scenario is illustrated in FIG. 5. The Responder scenario is illustrated in FIG. 6.

In the Requestor scenario, the participant's gateway initiates a request at Step 1. This request is sent to a certain web service endpoint URL as found in the UDDI registry based on the HCID. This URL in the pre-SOA lab would be the endpoint of the actual gateway node in the test lab as defined in the test case. In the proposed SOA based lab, an abstract endpoint is used to set up a URL in the UDDI that points to the agent's hostname rather than the actual gateway that provides the web services. For each type of a gateway node, an endpoint is published using the gateway agent's host name distinguished by the node parameter. If needed, agents could be deployed in a dedicated fashion to handle one node at a time as well.

At Step 2, a request is submitted to a lab agent's endpoint. When a message is en-route to its intended destination the gateway agent acts as a representative of the target gateway to help assist the message delivery to the actual gateway node. The focal point of the diagram is the Agent component and it portrays how it interacts with other components as part of the whole cross-gateway message exchange process.

At Step 3, a request is handled by the gateway agent. When any type of transaction is handled by the agent, it would be recorded using a message queue which is later persisted into a database table. A gateway agent provides a rule based interceptor that takes the original agent's endpoint and rewrites it to point to an actual gateway in the gateway farm.

At Step 4, a lab gateway node receives a request. After the request has been processed by gateway node the response is sent back to the initiating gateway through the agent.

In the Responder scenario (FIG. 6), the request is initiated by a gateway within the gateway farm at Step 1. The endpoint of the participant's gateway is retrieved from the UDDI but it is encoded in a base 64 encoded form parameter to the agent. At Step 2, a gateway client will be used to prepare a request with the encoded URL as shown in FIG. 5. At Step 3, the gateway sends a cross-gateway request to the agent with an encoded URL. At Step 4, the agent decodes the encoded parameter. At Step 5, the request is sent to the participant's gateway using the decoded URL.

Reference documents for CONNECT installation are publically available at developer.connectopensource.org. While the NwHIN lab setup can have ESB components and CONNECT installed on different physical machines, it is assumed for this example that both are installed on the same machine and CONNECT is installed before the ESB components. Connect must be installed prior to setting up any ESB components.

The Lab software may include a pre-canned test scenario(s) prepared to test against a predefined network of CONNECT Gateways, such as listed in TABLE IV below. A User can either replicate the similar configuration of the CONNECT Gateways, or modify the test scenarios to suite their CONNECT Gateways setup.

The hardware set up referenced below runs the test case scenarios and test cases. The exemplary set up is available in the DIL lab. Preferably, the participant gateway is set up with both CONNECT and NwHIN SOA Lab components on the same machine, given connection status check functionality of SOA LAB depends on CONNECT code.

TABLE IV

| | Environment | | | |
|---|---|---|---|---|
| Machine | Hardware/Software | HCID/AA | Description | |
| RI1 Gateway (required) | Win2003 Server; 5 Gb RAM | 2.16.840.1.113883.0.101 | Connect 2.4.8 software | |
| RI2 Gateway (required) | Win2003 Server; 5 Gb RAM | 2.16.840.1.113883.0.102 | Connect 2.4.8 software | |
| RI3 Gateway (required) | Win2003 Server; 5 Gb RAM | 2.16.840.1.113883.0.103 | Connect 2.4.8 software | |
| Participant Gateway (recommended) | Win2003 Server; 6 Gb RAM | 2.16.840.1.113883.0.200 | Connect 2.4.8 and NwHIN Lab software | |
| RI1-3.2 Gateway (required) | Win2003 Server; 5 Gb RAM | 2.16.840.1.113883.0.104 | Connect 3.2 Gateway software | |

Exemplary Software Installation
The following software is downloaded and installed for the development environment setup:

| INSTALL: | PROCESS STEPS/COMMENTS: |
|---|---|
| JAVA | Download and install Java Platform (e.g., Standard Edition (Java SE) 6 Update 18, available from Oracle Corporation, Redwood Shores, CA) Set the environment variable "JAVA HOME" Update the system environment variable "PATH" as PATH=%JAVA_HOME%\bin;%PATH% Open command prompt window and enter the command "java-version" to ensure correct version of JAVA is displayed |
| Tortoise SVN | Download TortoiseSVN 1.6.12, Build 20536 - 64 Bit, Subversion 1.6.15 (a free Windows Shell Extension for Subversion) |
| NwHIN TestLab software | Download the software from https://rd-ssp-01.aegis.net:8443/svn/lab/trunk/NwHIN into a location "C:\NwHIN" on the local file system Assume directory as "<NwHIN_software_install_dir>" (includes source code, database and related documentation) The SVN repository server or other source control tool will be available. |
| Apache Maven | Download Apache Maven 2.2.1 (not 3.x version) available from The Apache Software Foundation, Los Angeles, CA) Ensure that the M2_HOME environment variable is set to your Maven installation directory and also set the PATH=%PATH%\%M2_HOME%\bin Increase the amount of memory available to Maven by setting the MAVEN_OPTIONS environment variable as follows: Windows: set MAVEN_OPTS=-Xmx768m Open a Windows command prompt and run "mvn-version" to display the maven version installed Maven uses the directory <user home directory>\.m2 as the default root directory for maintaining its local repository and configuration - create .m2 directory if doesn't exist under user's home directory (Windows may not allow creating a directory with name .m2 from the Windows explorer. If so, use Windows command prompt (<user home directory>mkdir .m2)) Copy the settings.xml from <NwHIN TestLab software root dir>\Documents into <user home directory>\.m2 (This file contains the necessary configuration used by Maven to download third party jars from Fuse ESB repository) |
| Eclipse | Download Eclipse Java EE IDE for Web Developers, Version: Helios Service Release 2 from below URL (available from The Eclipse Foundation) Windows 64-bit version: Unzip the contents into a location "C\Eclipse3.6" and assume eclipse installation directory "C\Eclipse3.6" as <eclipse_install_dir>; Go to <eclipse_install_dir> and create a shortcut for eclipse.exe and add it to the Start menu (eclipse icon is added to the Start menu); ] Click on the eclipse icon to open eclipse IDE. (Refer Appendix "0 to import projects in to eclipse IDE") |
| Source Code Install (Windows) Database (MySQL) | Follow CONNECT reference instructions to install MySQL database (programmatic access to this database is done using Hibernate configuration files) |

To set up Lab Database:

1. Open command prompt and issue the following command (Note that since the MySQL install has made changes to the path environment variable, it will be necessary to open a new command window.):
cd <NwHIN_software_install_dir>\Database\labdb
mysql -v -uroot -pNHIE-Gateway < lab_DDL.sql
2. Load data for Lab Database (Naresh)
Open the file lab_DML.sql under <NwHIN_software_install_dir>\Database\labdb \ folder and update the set host name parameters values
set @hostname_participant := 'participant_hostname';
set @hostname_RI1 = 'RI1_hostname';
set @hostname_RI2 = 'RI2_hostname';
set @hostname_RI3 = 'RI3_hostname';
set @hostname_RI1_Connect32 := 'RI1_Connect32_hostname';
Open command prompt and issue the following command:
cd <NwHIN_software_install_dir>\Database\labdb
mysql -v -uroot -pNHIE-Gateway < lab_DML.sql
3. Load Documents in Reference Implementation Database
Log on to RI1 server
Download RI1_patient_docs.sql to C:\DBScripts from the repository
Open command prompt and issue the following command:
C:\> cd DB Scripts
C:\ DBScripts > mysql -v -uroot -pNHIE-Gateway < RI1_patient_docs.sql
Log on to RI2 server
Download RI2_patient_docs.sql to C:\DBScripts from the repository
Open command prompt and issue the following command:
C:\> cd DBScripts
C:\ DBScripts > mysql -v -uroot -pNHIE-Gateway < RI2_patient_docs.sql
Log on to RI3 server
Download RI3_patient docs.sql to C:\DBScripts from the repository
Open command prompt and issue the following command:
C:\> cd DBScripts
C:\ DBScripts > mysql -v -uroot -pNHIE-Gateway < RI3_patient docs.sql
Log on to RI1-3.2 server (Connect 3.2 Gateway)
Download RI1_connect32_patient docs.sql to C:\DBScripts from the repository
Open the file and update the HCID value (set @HCID: = '2.16.840.1.113883.0.104';)
Open command prompt and issue the following command:
C:\> cd DB Scripts
C:\ DBScripts > mysql -v -uroot -pNHIE-Gateway < RI1 connect32_patient_docs.sql
4. Load Documents in Participant Gateway Database
Log on to Participant server
Download Participant_patient_docs.sql to C:\DBScripts from the repository
Open command prompt and issue the following command:
C:\> cd DBScripts
C:\ DBScripts > mysql -v -uroot -pNHIE-Gateway < Participant_patient_docs.sql Additional software downloads and installation for environment setup:

| INSTALL: | PROCESS STEPS: |
| --- | --- |
| Fuse ESB | Download Apache-Servicemix-4.4.0-Fuse-00-43 from FuseSource |
| | Unzip the downloaded zip file into a location on the local file system (ensure the path doesn't contain spaces; name FuseESB installation directory as FUSE_HOME) |
| | Open the file < FUSE_HOME >/etc/system.properties and update the property "org.osgi.service.http.port=7001". |
| | Open the file < FUSE_HOME >/bin/servicemix.bat and append the following options to DEFAULT_JAVA_OPTS. |
| | "-X:PermSize=256m -XX:MaxPermSize=256m" |
| | Open a Windows command prompt and execute the following commands: |
| | <FUSE_HOME>\bin\servicemix.bat (Launch FuseESB) |
| | karaf@root>list (List installed features and bundles) |
| | karaf@root>shutdown (Shutdown FuseESB) |
| Karaf web console (optional) | (Karaf is a lightweight OSGi container that is bundled with ServiceMix and provides a console interface for managing the ServiceMix) |
| | If not already running ServiceMix, open a Windows command prompt and execute the following commands: |
| | <FUSE_HOME>\bin\servicemix.bat (Launch FuseESB) |
| | karaf@root>features:install webconsole |
| | karaf@root>refresh |
| | karaf@root>list |
| | To access Karaf console, open a browser for localhost:7001/system/console (enter login details) |

| INSTALL: | PROCESS STEPS: |
|---|---|
| ActiveMQ web console(optional) | Shutdown the ServiceMix if already running (karaf@root>shutdown)<br>Edit <FUSE_HOME>\etc\system.properties and add the following configuration:<br>webconsole.type=properties<br>webconsole.jms.url=tcp://localhost:61616<br>webconsole.jmx.url=service:jmx:rmi:///jndi/rmi://localhost:1099/karaf-root<br>webconsole.jmx.user=smx<br>webconsole.jmx.password=smx<br>Launch FuseESB:<br><FUSE_HOME>\bin\servicemix.bat<br>karaf@root> features:install activemq-web-console<br>karaf@root>refresh<br>karaf@root>list<br>To access the ActiveMQ web console, open a browser and go to localhost:7001/activemqweb |

To Configure Database for ActiveMQ:

| Create the database schema for ActiveMQ by executing the following commands: |
|---|
| mysql -uroot -p<password><br>mysql> CREATE DATABASE 'activemq' ;<br>mysql> GRANT ALL ON activemq.* TO 'nhincuser'@'localhost' IDENTIFIED BY 'nhincpass';<br>mysql> GRANT ALL ON activemq.* TO 'nhincuser'@'127.0.0.1' IDENTIFIED BY 'nhincpass';<br>mysql> GRANT ALL ON activemq.* TO 'nhincuser'@'{host name}' IDENTIFIED BY 'nhincpass';<br>Copy < NwHIN_software_install_dir >\Documents\activemq-broker.xml to <FUSE_HOME>\etc.<br>Install the JDBC driver in ServiceMix:<br>karaf>osgi:install -s mvn:com.mysql.jdbc/com.springsource.com.mysql.jdbc/5.1.6<br>Install Apache commons dbcp in ServiceMix:<br>karaf>osgi:install -s mvn:org.apache.servicemix.bundles/org.apache.servicemix.bundles.commons-dbcp/1.2.2_5<br>Re-install the ActiveMQ broker in ServiceMix:<br>karaf> features:uninstall activemq-broker<br>karaf> features:install activemq-broker<br>Verify that the following three tables are created under the schema:<br>1) "activemq"<br>2) activemq_acks, activemq_lock<br>3) activemq_msgs |

(Note:
If the above tables are not created in MySQL, restart the Fuse server so it can pick up the new changes).

For installation of ESB Components:

| | |
|---|---|
| Build and install ESB Components into Maven local repository | Open command line window and go to:<br><NwHIN_software_install_dir>\ESBComponents<br>Execute the following maven command:<br>mvn clean install<br>Verify that the jar files are installed in maven local repository:<br>.m2\repository\net\aegis\ LabCommons\1.0.0\ LabCommons-1.0.0.jar<br>.m2\repository\net\aegis\gateway\client\Connect248WSClient\1.0.0\ Connect248WSClient-1.0.0.jar<br>.m2\repository\net\aegis\gateway\client\Connect32WSClient\1.0.0\ Connect32WSClient-1.0.0.jar<br>.m2\repository\net\aegis\ TestProcessor \1.0.0\ TestProcessor -1.0.0.jar<br>.m2\repository\net\aegis\LabCore\1.0.0\LabCore-1.0.0.jar<br>.m2\repository\net\aegis\MessageDispatcher\1.0.0\MessageDispatcher-1.0.0.jar<br>.m2\repository\net\aegis\MessageValidator\1.0.0\MessageValidator-1.0.0.jar |
| Deploy artifacts into Fuse ESB | Copy features.xml from https://rd-ssp-01.aegis.net.8443/svn/lab/trunk/NwHIN/Documents/features.xml to "<FUSE_HOME>\etc\" folder<br>Execute the following commands from the Karaf console:<br>karaf@root> features:addUrl file: <file path>/features.xml (Install the features file) |

-continued

```
Ex : features:addUrl file: <FUSE_HOME>/etc/features.xml
karaf@root> features:listUrl verify the installation of the file)
karaf@root> features:install esb-components (Install the Lab ESB feature)
karaf@root> features:list | grep esb-components (verify the ESB feature)
karaf@root>list
```

For installation of User Interface:

| | |
|---|---|
| Build and install Web Applications into Maven local repository | Open command line window and navigate to <NwHIN_software_install_dir>\ Webapps and execute the following command:<br>mvn clean process-resources -DbuildNumber="1" -DbuildVersion="2.0" install<br>(Note: The buildNumber and buildVersion parameters need to be incremented for each build which will be used only in the LabGUI project)<br>Make sure the jar files are installed in maven local repository:<br>\.m2\repository\net\aegis\ TestProcessorWSClient \1.0.0\ TestProcessorWSClient -1.0.0.jar<br>\.m2\repository\net\aegis\LABGUI\1.0.0\ LABGUI-1.0.0.war<br>\.m2\repository\net\aegis\LabParticipant\1.0.0\ LabParticipant-1.0.0.war |
| Deploy the artifacts into Participant Gateway glassfish server | Ensure environment variable is added:<br>"aegis.implementation.environment=dev" in order to pick the development data base.<br>Deploy "LabGUI.war" from:<br>"<NwHIN_software_install_dir>\Webapps\LabGUI\target" to participant/candidate gateway server using Glassfish admin console.<br>Deploy "LabParticipant.war" from:<br>"<NwHIN_software_install_dir>\Webapps\ LabParticipant \target" to participant/candidate gateway server using Glassfish admin console. |

For installation of Gateway Agent:

Download contents from https://rd-ssp-01.aegis.net:8443/svn/lab/trunk/Gateway/Agents/UniversalGatewayAgent/bin.zip into a location "C:\NwHIN"
Unzip the downloaded zip file.
Set MEMBRANE_HOME to <install_path>\router\membrane-router-2.0.4\
Edit monitor-beans.xml <install_path>\router\membrane-router-2.0.4\config
Set database URL
Edit rules.xml under <install_path>\router\membrane-router-2.0.4\config
Ensure certificates and keystores are valid in rules.xml
Ensure hostnames are set
Ensure port numbers do no conflict
Update the service endpoint hostname and port number in InternalConnectionInfo.xml on the participant and RI's servers:
Participant_Hostname:portnumber –> agent_Hostname:portnumber
Server_Hostname:portnumber –> agent_Hostname:portnumber
Test by entering the updated endpoint with ?wsdl in a browser window: Run memrouter.bat Installation Appendix CONNECT Gateway:

As part of the CONNECT installation process, CONNECT copies default configuration files to "<server>/domain/domain1/config/nhin" folder, which files have been modified per Conformance and Interop test cases definition.
Configuration files to update in participant and Reference Implement (RI) gateway servers include:
config/mpi.xml
config/nhin/ internalConnectionInfo.xml
(Note: open internalConnectionInfo.xml in notepad and verify HCID and host names are correct; open mpi.xml in notepad and verify HCID value)
Participant Configuration
Navigate to "<NwHIN_software_install_dir>\Documents\Connect-Gateways\Participant" folder
Copy "config" directory from "<NwHIN_software_install_dir>\Documents\Connect-Gateways\Participant to "<Participant -Server>/domain/domain1/config/nhin" directory using remote desktop option -continued

| CONNECT Gateway: |
|---|
| Reference Implementation Configuration
RI1 configuration files:
Assumption: The format of "Unique Patient-Id" in mpi.xml is assumed as "RI1. <last 3 digits of HCID>.<5-digit-patientID>"
Navigate to "<NwHIN_software_install_dir>\Documents\Connect-Gateways\RIs\RI1" folder path
Copy "config" directory from "<NwHIN_software_install_dir>\Documents\Connect-Gateways\RIs\RI1" to "<RI1-server>/domain/domain1/config/nhin" directory using remote desktop option
RI2 configuration files:
Assumption: The format of "Unique Patient-Id" in mpi.xml is assumed as "RI2. <last 3 digits of HCID>.<5-digit-patientID>"
Navigate to "<NwHIN_software_install_dir>\Documents\Connect-Gateways\RIs\RI2" folder path
Copy "config" directory from "<NwHIN_software_install_dir>\Documents\Connect-Gateways\RIs\RI2" to "<RI2-server>/domain/domain1/config/nhin" directory using remote desktop option
RI3 configuration files:
Assumption: The format of "Unique Patient-Id" in mpi.xml is assumed as "RI3. <last 3 digits of HCID>.<5-digit-patientID>"
Navigate to "<NwHIN_software_install_dir>\Documents\Connect-Gateways\RIs\RI3" folder path
Copy "config" directory from "<NwHIN_software_install_dir>\Documents\Connect-Gateways\RIs\RI3" to "<RI3-server>/domain/domain1/config/nhin" directory using remote desktop option
RI1-3.2 configuration files:
Assumption: The format of "Unique Patient-Id" in mpi.xml is assumed as "RI1. <last 3 digits of HCID>.<5-digit-patientID>"
Navigate to "<NwHIN_software_install_dir>\Documents\Connect-Gateways\RIs\RI1-3.2" folder path
Copy "config" directory from "<NwHIN_software_install_dir>\Documents\Connect-Gateways\RIs\RI1-3.2" to "<RI1-3.2-server>/domain/domain1/config/nhin" directory using remote desktop option |

| Apache Tomcat |
|---|
| Assumption: Install the tomcat server on the connect participant gateway machine
Install tomcat
Download Apache Tomcat v6.0.35
Unzip the contents into a location "C:\tomcat-6" and assume tomcat installation directory "C:\tomcat-6" as <tomcat_install_dir>
Tomcat listens on the default port 8080. If this port is conflicting with any software that is running on the system for example CONNECT, change the default port 8080 to an unused port for example 8282 in <tomcat_install_dir>\conf\server.xml.
Set up certificate in tomcat
Append Java options for trust store and trust store password in
<tomcat_install_dir>\bin\catalina.bat
-Djavax.net.ssl.trustStore="<connect_server>/config/cacerts.jks"
-Djavax.net.ssl.trustStorePassword="changeit"
Note: cacerts.jks contains all certificates information and the file will be available in participant connect gateway server path
Reference content of catalina.bat file is below:
set JAVA_OPTS=%JAVA_OPTS% -Djavax.net.ssl.trustStore="C:/Sun/AppServer/domains/domain1/config/cacerts.jks" -Djavax.net.ssl.trustStorePassword="changeit" %LOGGING_CONFIG%
Copy third party jars to tomcat lib folder
Copy all jars from "<NwHIN_software_install_dir>\ThirdPartyJars\XStream" directory to "<tomcat_install_dir>\lib" folder
Deploy the artifacts into Tomcat server
Make sure environment variable is added "aegis.implementation.environment=dev" in order to pick development data base.
Copy "LabGUI.war" from "<NwHrN_software_install_dir>\Webapps\LabGUI\target" to "<tomcat_install_dir>\webapps" directory .
Copy "LabParticipant.war " from "<NwHIN_software_install_dir>\Webapps\LabParticipant \target" to "<tomcat_install_dir>\webapps" directory
Start the tomcat server from "<tomcat_install_dir>\bin\ startup.bat
Open browser and type http://localhost:8080/LabGUI/security/SignOn to access login to LabGUI
Note: Verify the port number that is configured as part of tomcat installation step |

Figure 10:
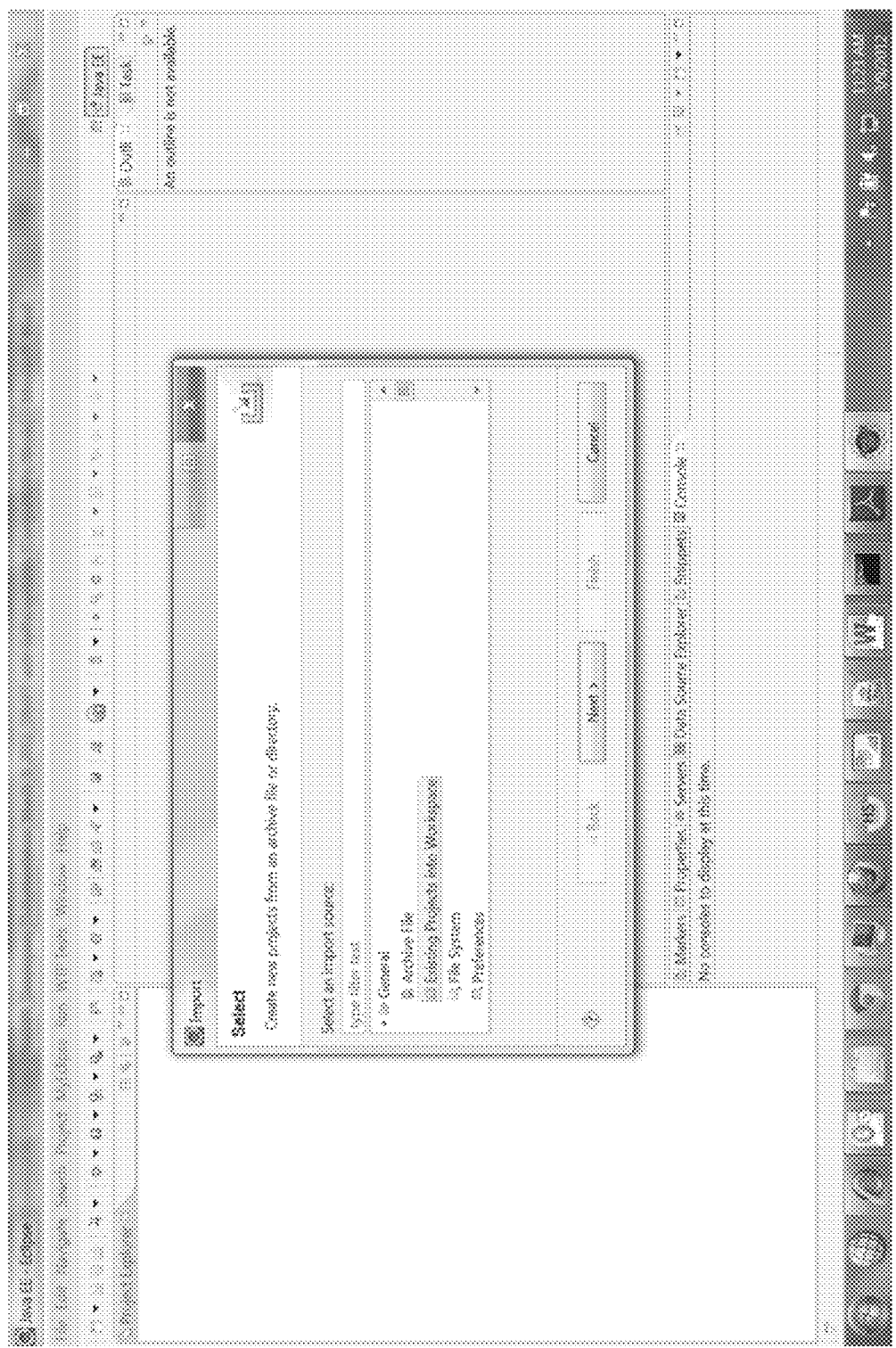
FIG. 10 illustrates a screen view during an importation of Eclipse IDE.
Figure 11:
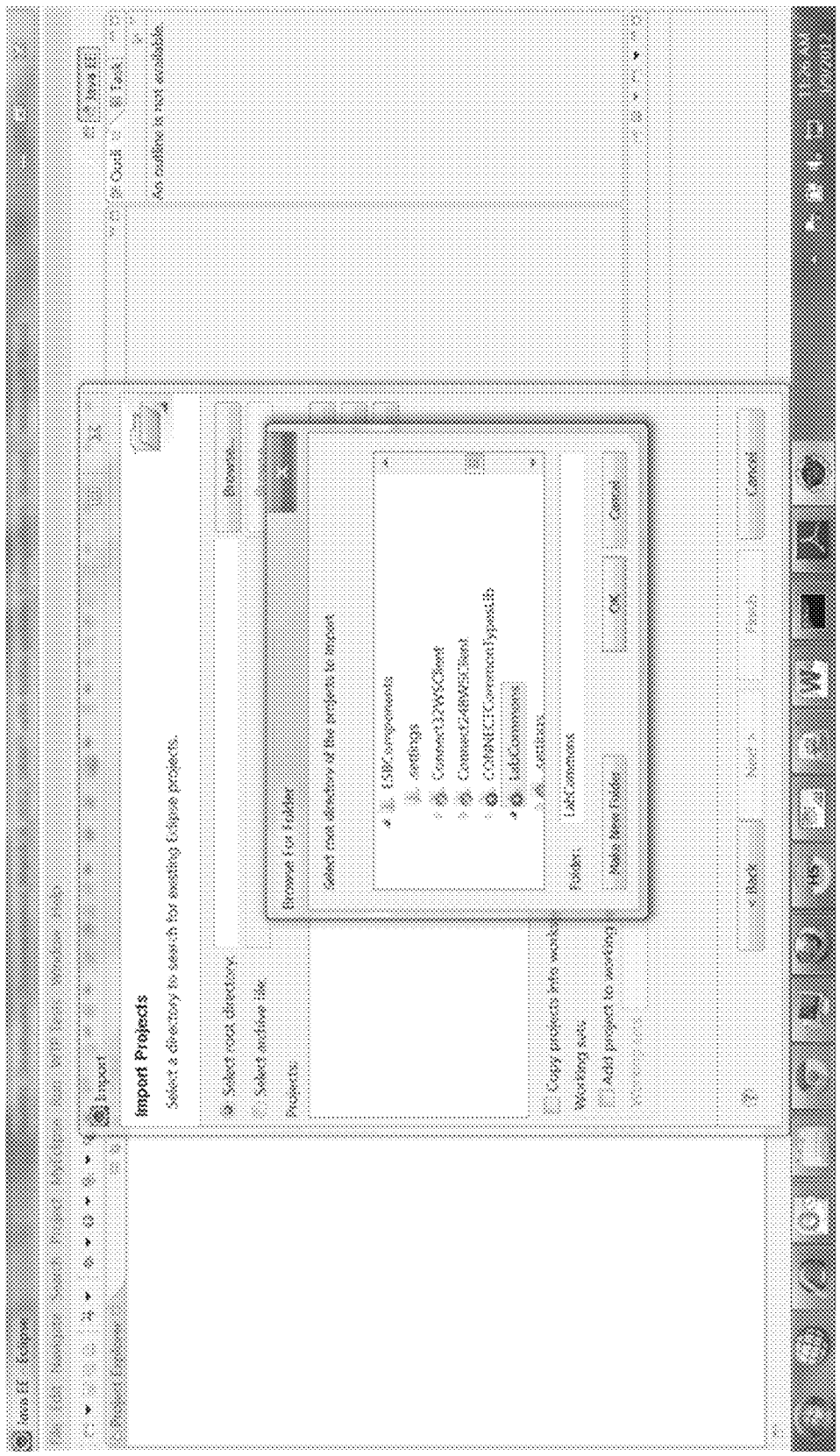
FIG. 11 illustrates another screen view during the importation process of FIG. 10.

| Import Projects into Eclipse IDE |
|---|
| Open Eclipse IDE and chose work space for projects as:<br>"<NwHrN_software_install_dir>"(C:\NwHIN)<br>Navigate to "File" menu and choose "import" sub menu under File which will open pop up window and choose "existing projects in workspace under General in pop up window (Figure 10)<br>Click Next to select the specific project<br>Click the browse button to select specific project (Ex : LabCommons under ESBcomponents) (FIG. 11)<br>Click OK button<br>Click Finish Button to complete project import in to Eclipse IDE.<br>Follow above steps to import all remaining projects under ESB Components and WebApps |

EXAMPLE 3

Static Test Cases

With reference to FIGS. 12-34, exemplary process steps and functionality for establishing an account in the DIL, establishing a static test case scenario, executing a test case scenario and viewing results from the executed static test case are disclosed.

Figure 12:
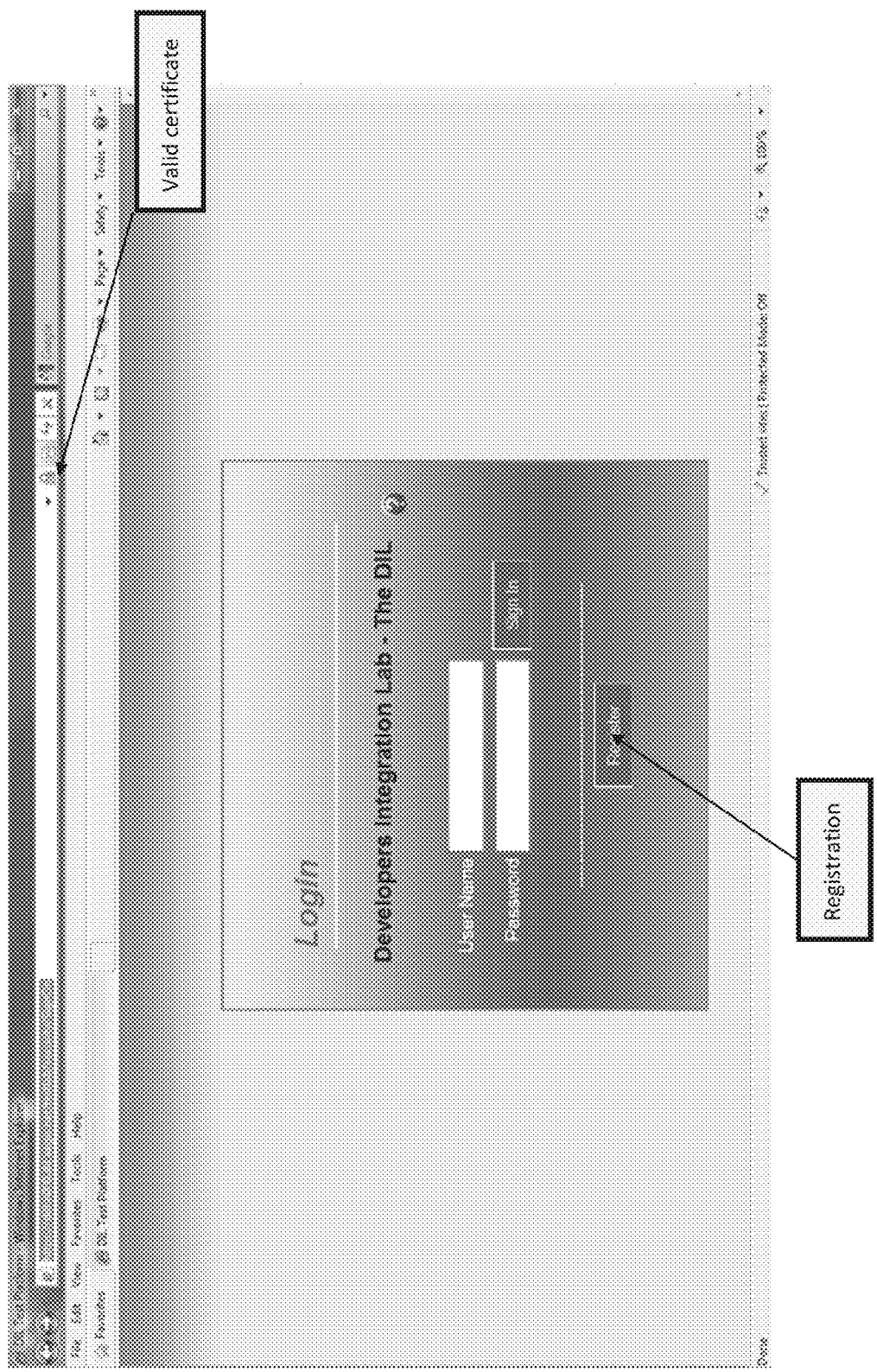
Figure 13:
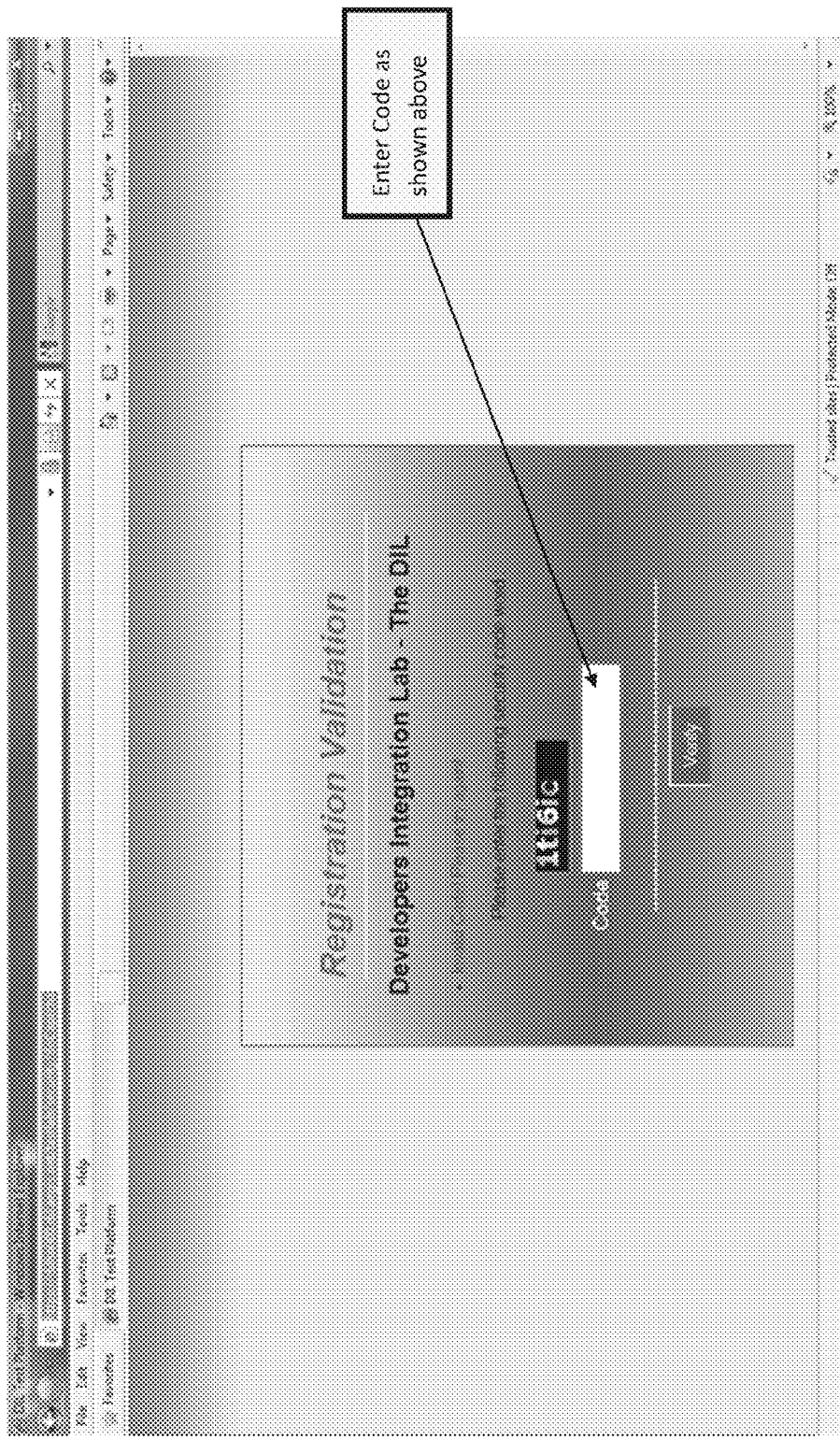

After a user first obtains a valid certificate (FIG. 12, showing a 'lock' icon indicating secure https exchange of encrypted information), account registration may then proceed. The user clicks on a "Register" tab to proceed with the DIL registration process. The user is then prompted to enter a security code (FIG. 13) to perform registration validation. If the code is not entered correctly, the user will be prompted to re-enter the code for security purposes. The user then clicks on the "Verify" tab.

Figure 14:
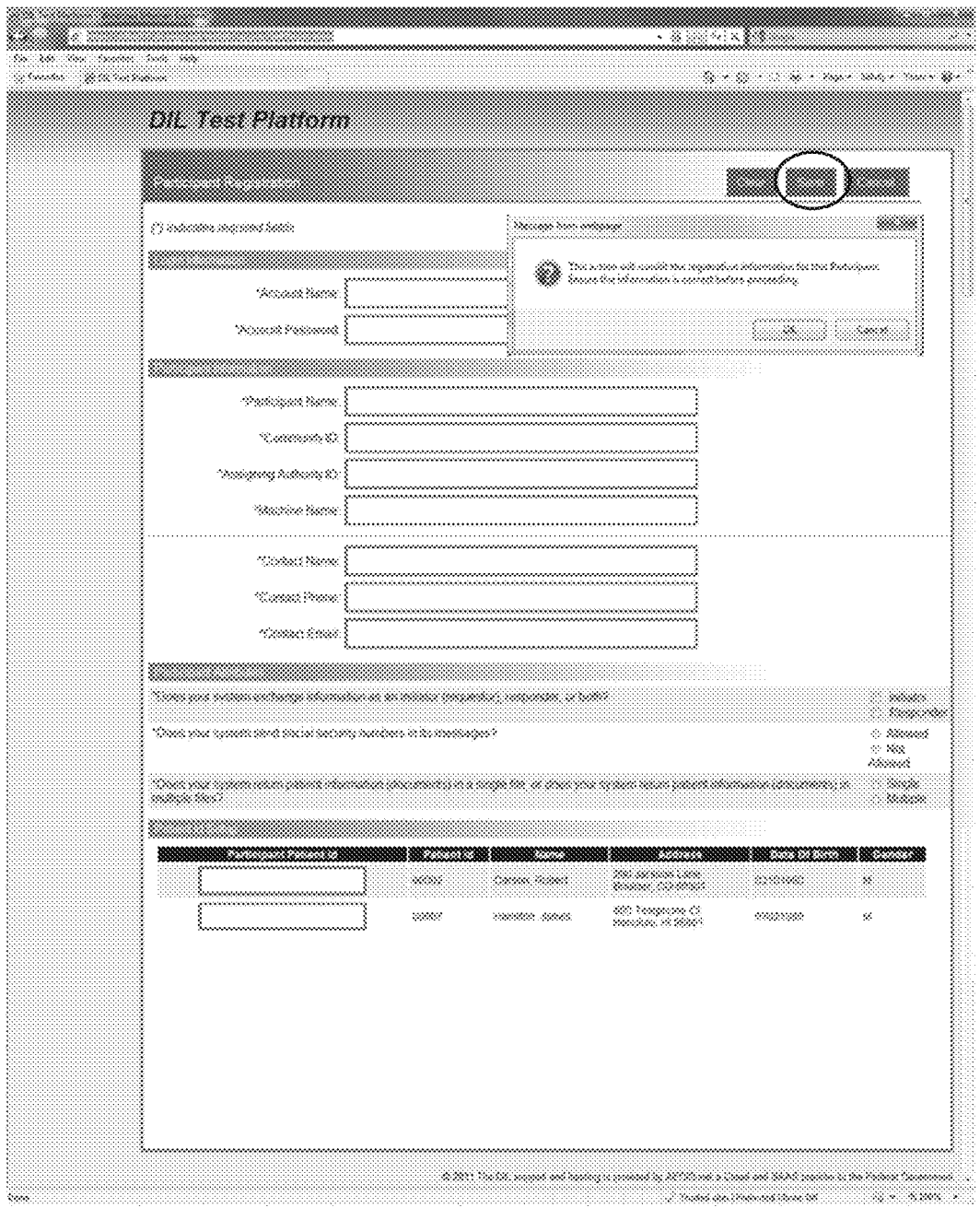

After the security code has been verified, the user is directed to a registration form. The user must complete various fields on the form (FIG. 14), for example: account name, password, participant name, community identification, assigning authority identification, machine name, contact name, phone, email, etc.). Once a user's information is entered in the DIL, the DIL uses the information for purposes of tracking test information. The user also enters patient identification information in a "Patient ID Setup". When entering patient information, all should be completed, and each patient identification entry should be unique. The user may then save (via clicking the "Save" tab) the registration and patient information. The user may be prompted to ensure all information is correct prior to clicking the Save tab (as shown in FIG. 14).

Figure 15:
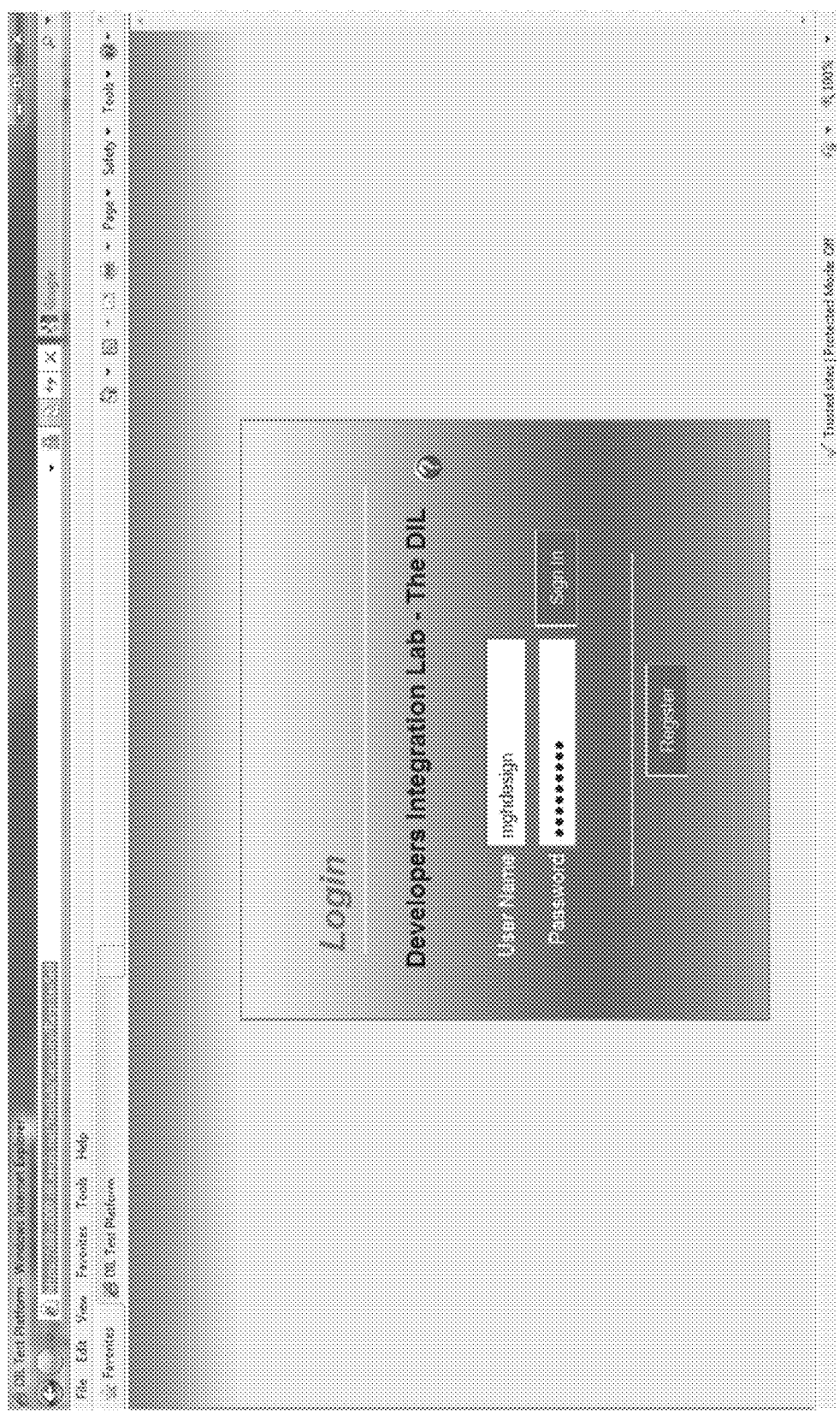

After saving the information, the registration is complete. The user may then log into the DIL to set up and execute a test case (FIG. 15). In a Log In screen, the user name and password may be entered. The user then enters the DIL by clicking the "Sign In" tab.

Figure 16:
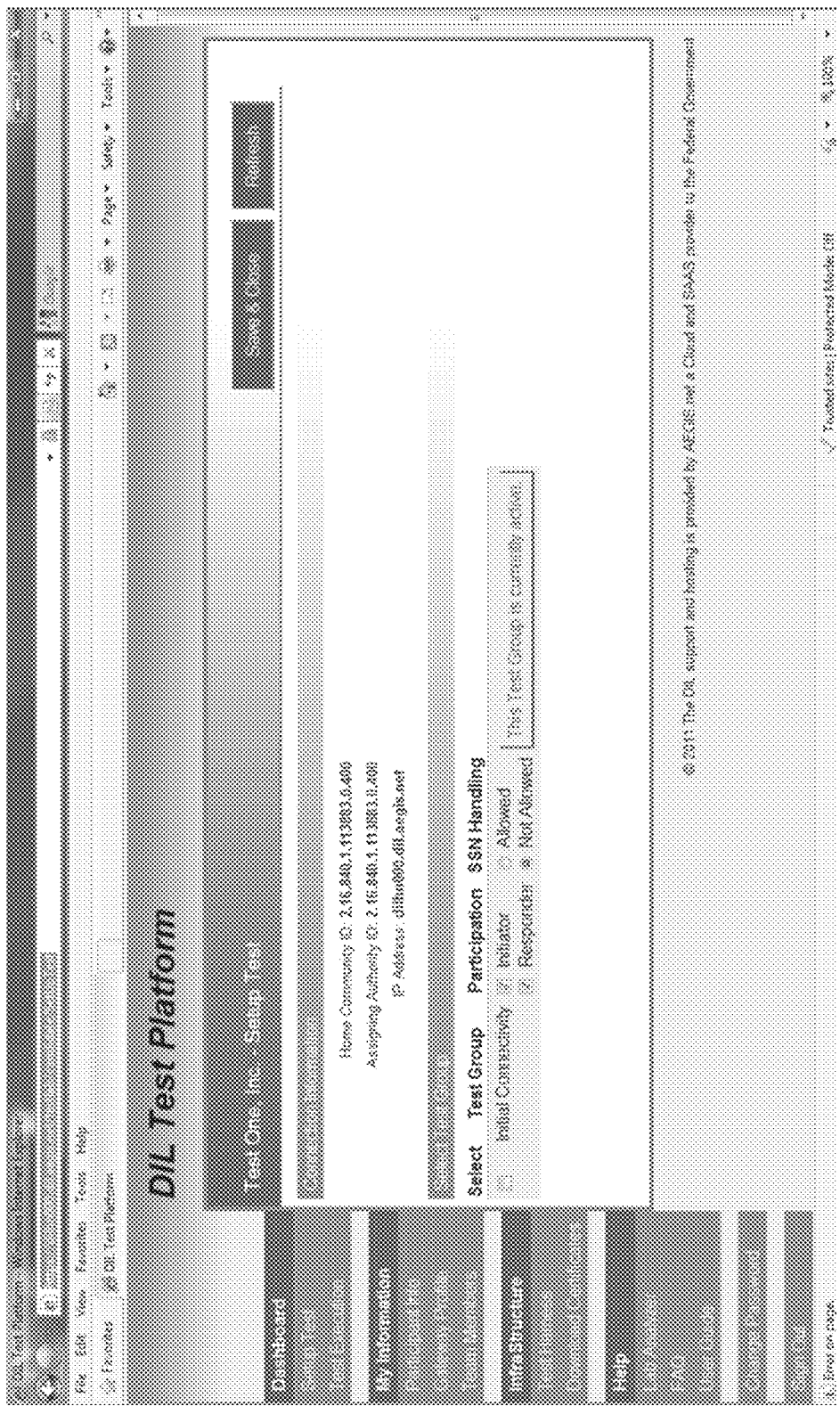
Figure 17:
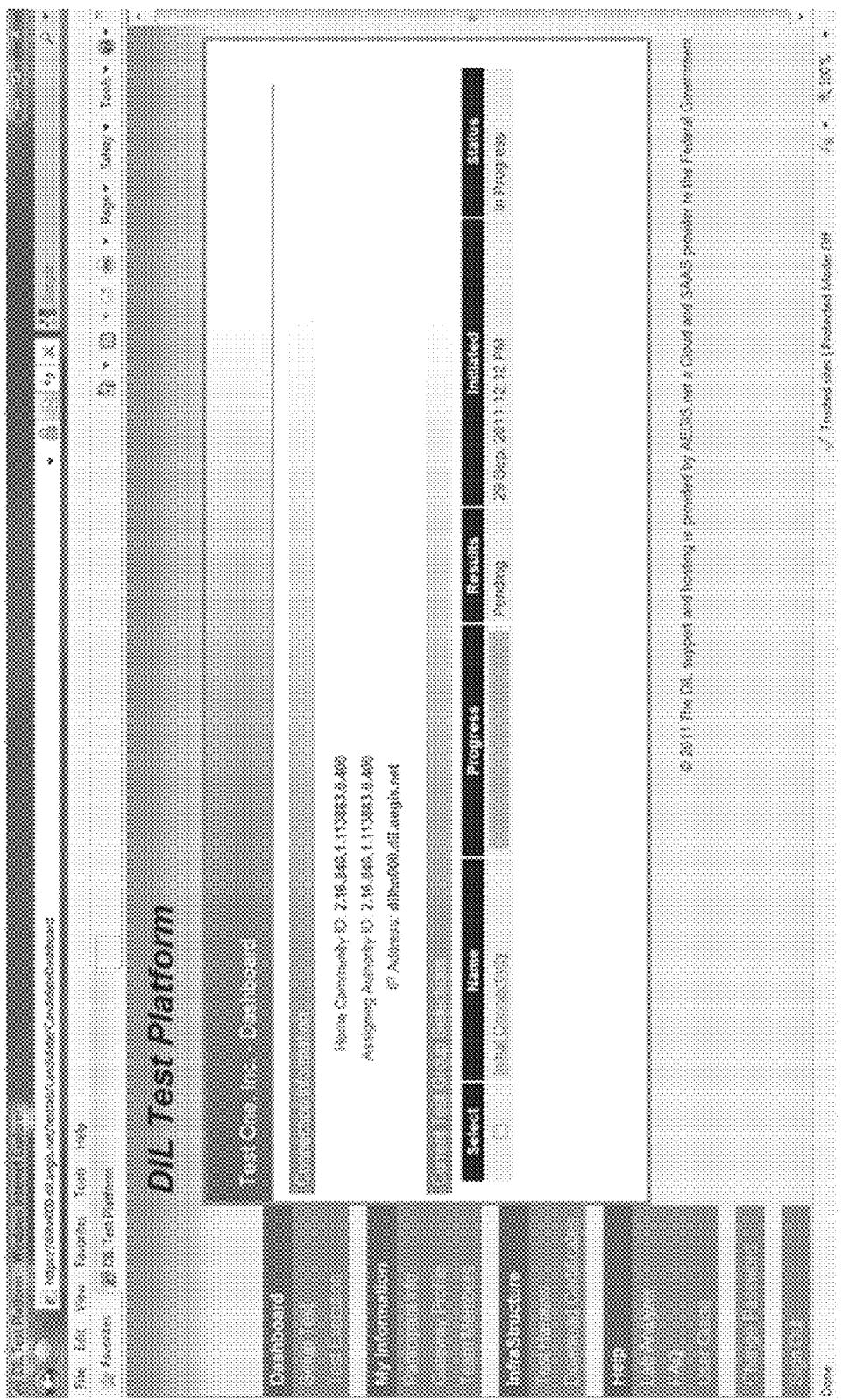

Once logged in, the user may set up a test case and select the test group (FIG. 16). The test group may include the following attributes: 1) initiator or responder, and 2) Social Security Handling. The user can verify the connection between the participants system and the DIL. If the user attempts to navigate away from the screen with unsaved changes, the DIL prompts the user to "Save & Close" or "Refresh". A Dashboard screen displays and manages test cases and shows the test case(s) in progress (FIG. 17).

Figure 18:
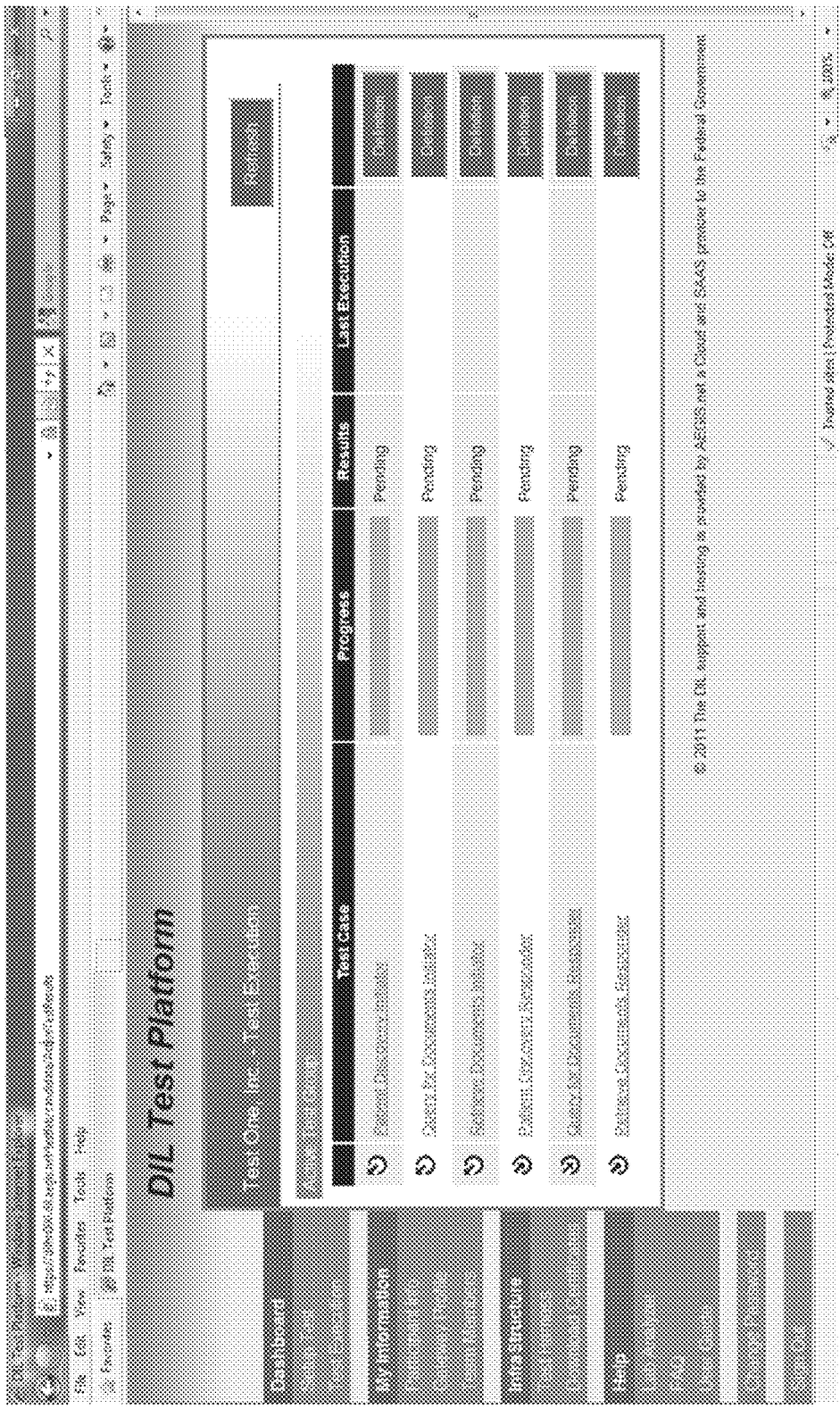

A Test Execution screen provides the user information relating to an active test group and allows the user to view the definition of a test case (FIG. 18). The Test Execution screen includes a "Refresh" button, which polls the database for the latest test results. By clicking on a "Definition" tab, the user is navigated to a pop-up window to view a detailed description of the test cases included in a given test scenario.

The DIL testing process intends for tests to be run one scenario at a time. The Initiator and Responder scenarios accomplish this differently. When the applicant's system is the Initiator, the user does the following for each test scenario: 1) reads through the test case description; 2) initiates the corresponding cross gateway exchange from the system under test, allowing two to three minutes for the DIL Lab GUI to refresh and display the status of the test case; and 3) clicks on the Test Case to view the results of the test case execution, as needed.

Figure 19:
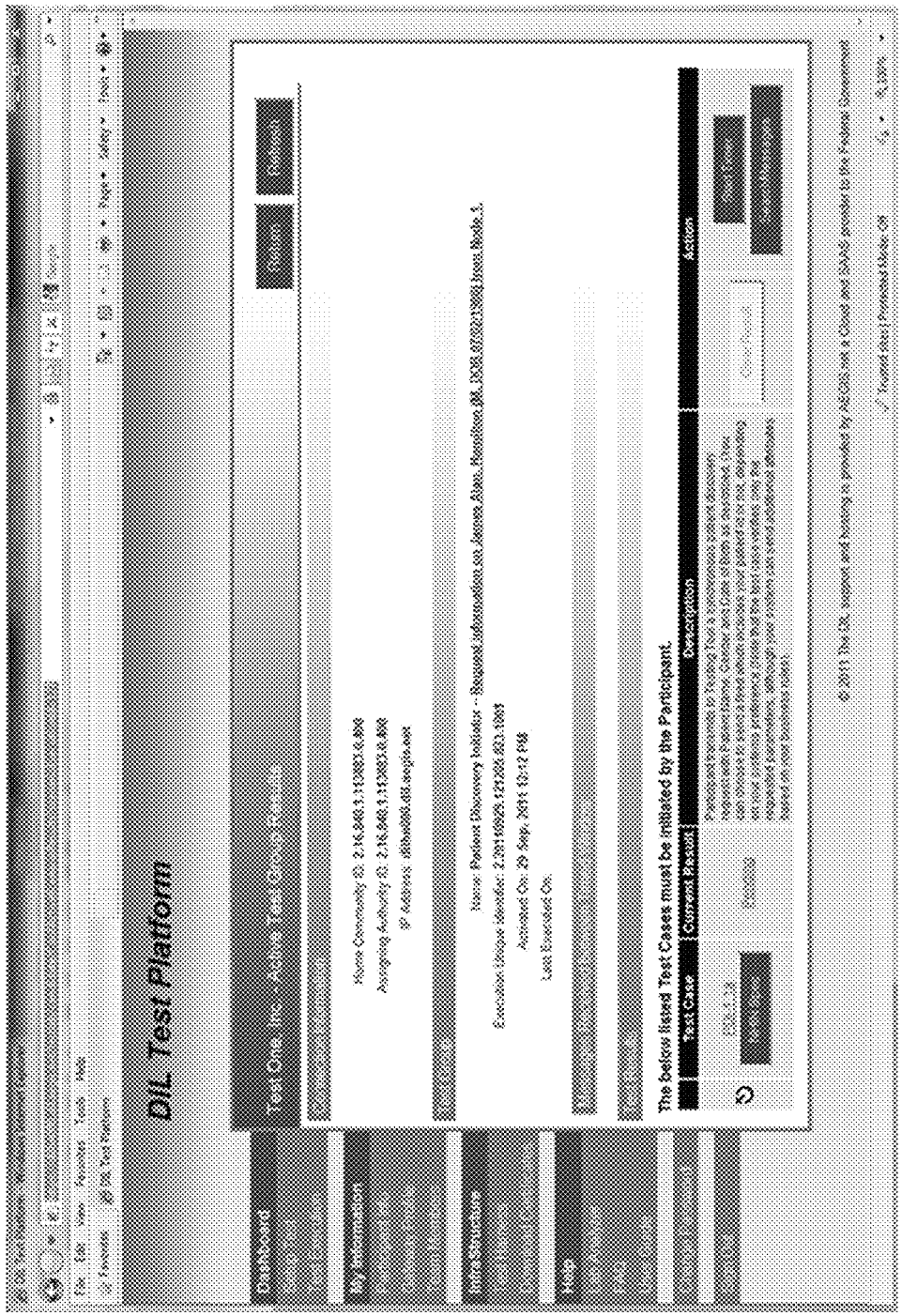

The user may click a particular "Test Case" and receive the NHIN specifications (such as, e.g., PDI-1.1a as shown in FIG. 19). The user is then navigated to a reference NHIN Specification (FIG. 20). The NHIN Specification reference from the initiator test scenario is displayed. The user may click on "Close" to exit the NHIN Specification.

Figure 21:
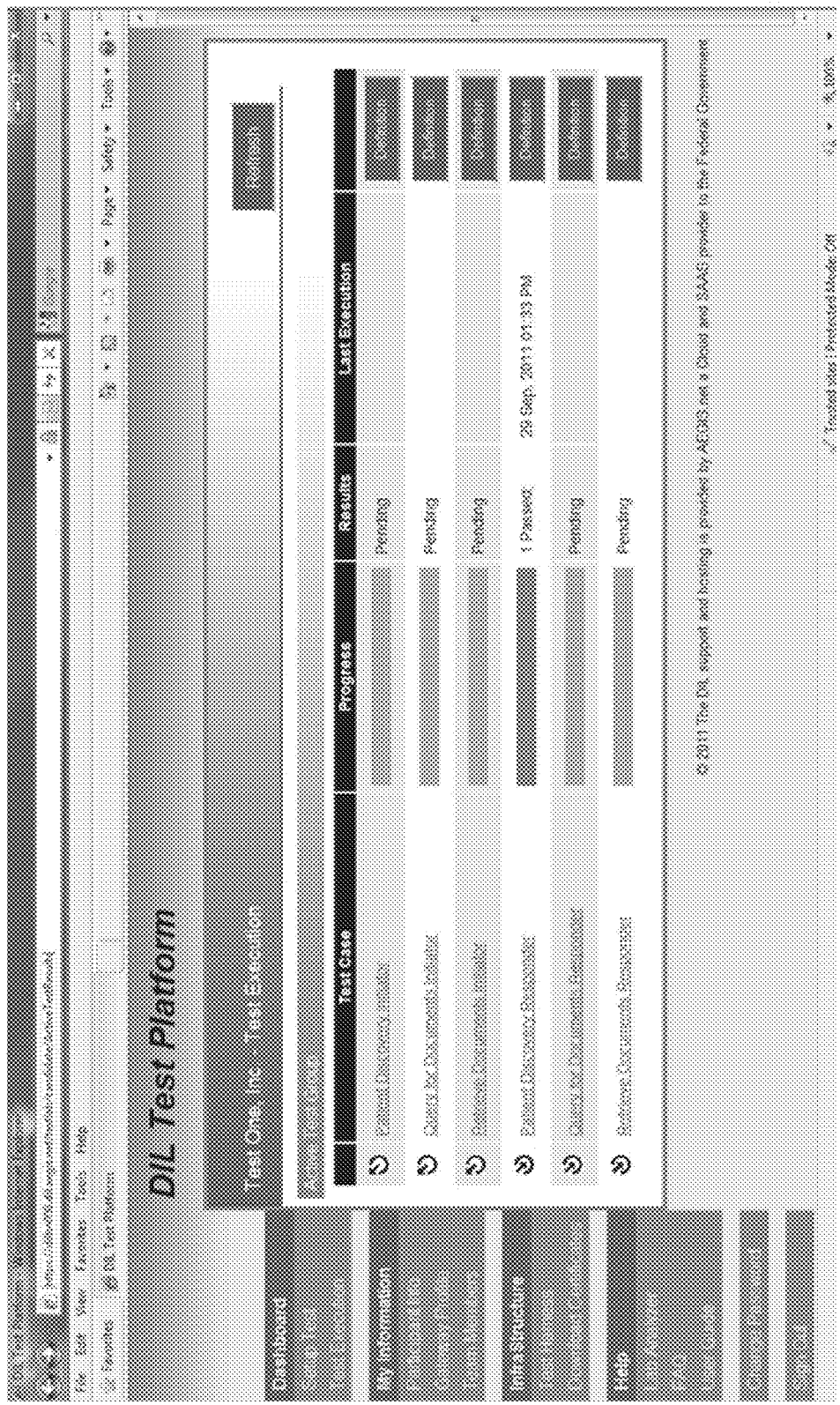
Figure 22:
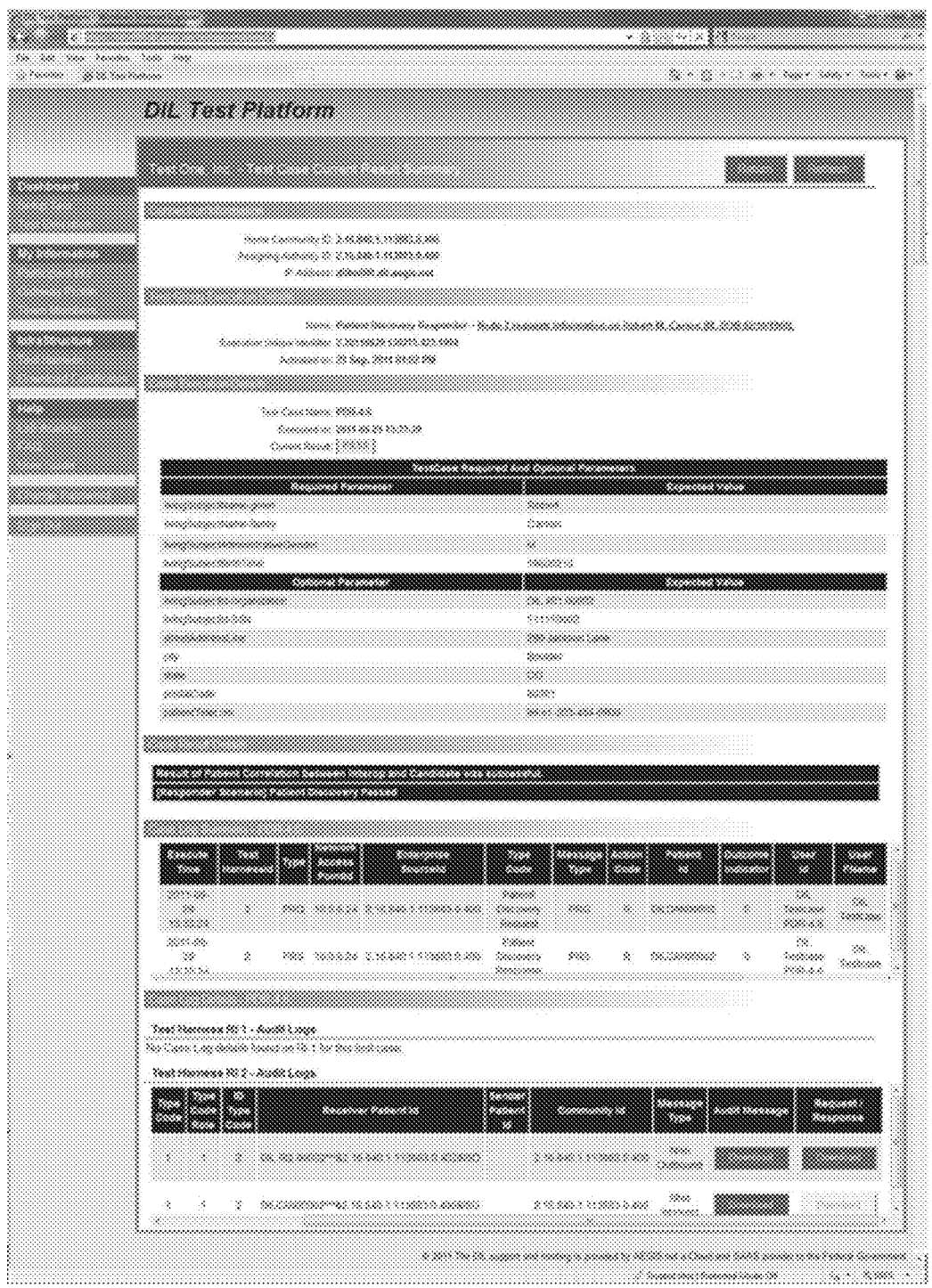

The Active Test Results screen (FIG. 21) includes a "Refresh" button, which polls the database for the latest test results. The DIL may display color-coded test results and/or identify the test case status at a particular date and time (FIG. 21). By clicking on "Definition", the user navigates to a pop-up window to view a detailed description of the test case (such as shown in FIG. 22).

Figure 23:
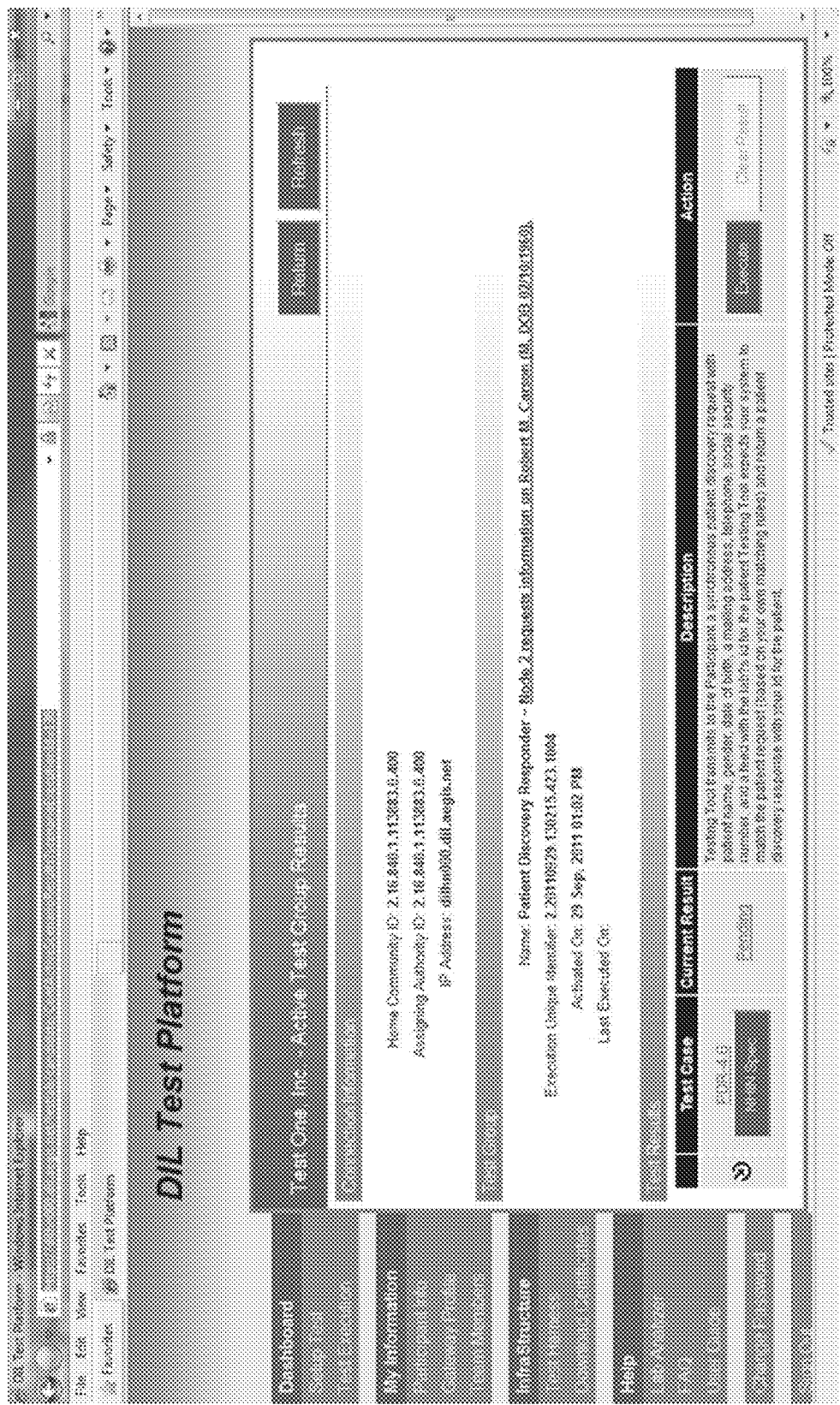
Figure 24:
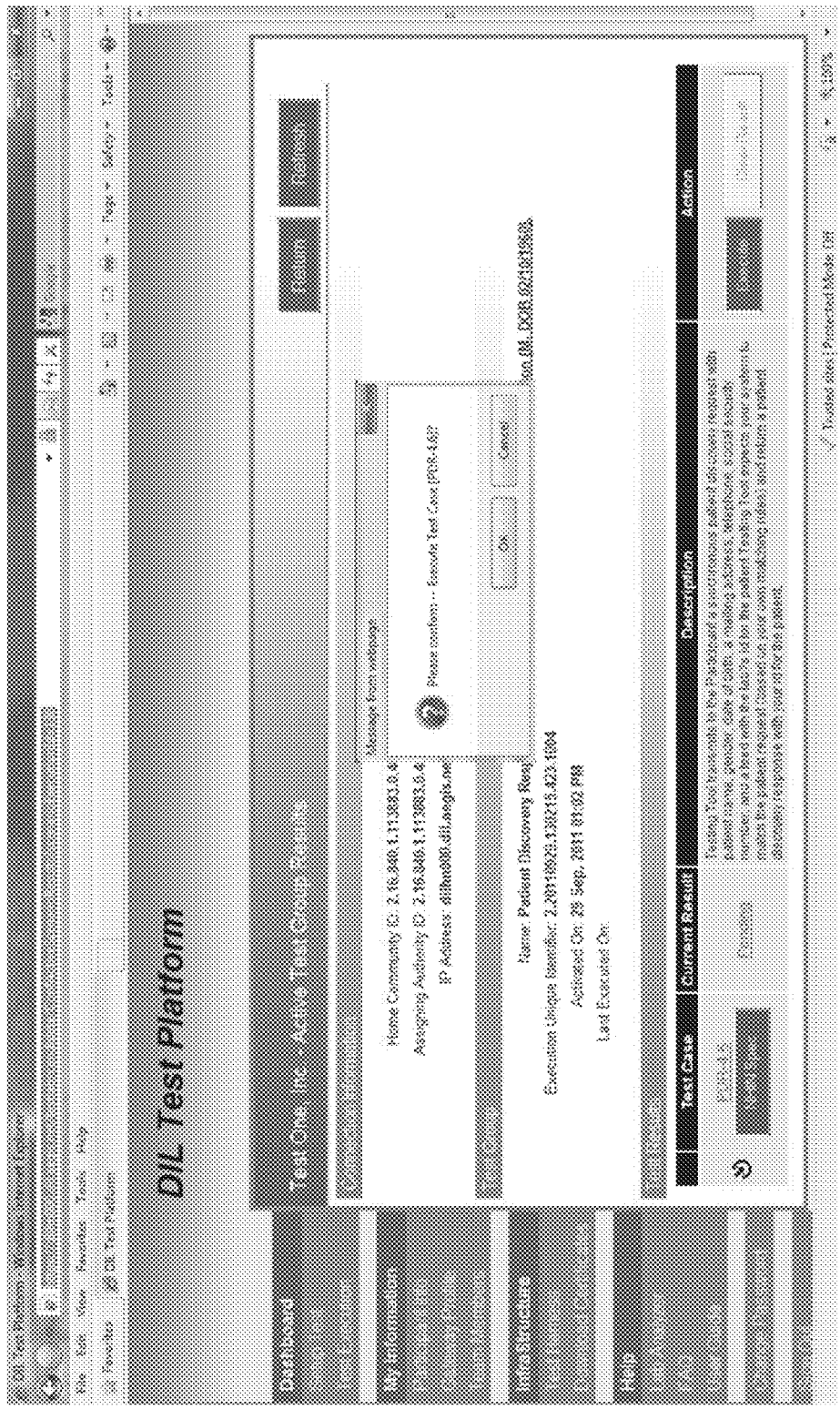

A Test Case Current Result Summary screen shows the results of a test case and allows the user to view audit information as well as specific test case information (FIG. 23). By checking the Case Execution Details section in the Case Result Details section, the user can compare the expected test results and the actual test results. Within a Case Log Details section, the DIL displays Download buttons, whereby the user may click on and download specific audit messages related to the audit and request/response exchange results.

Figure 25:
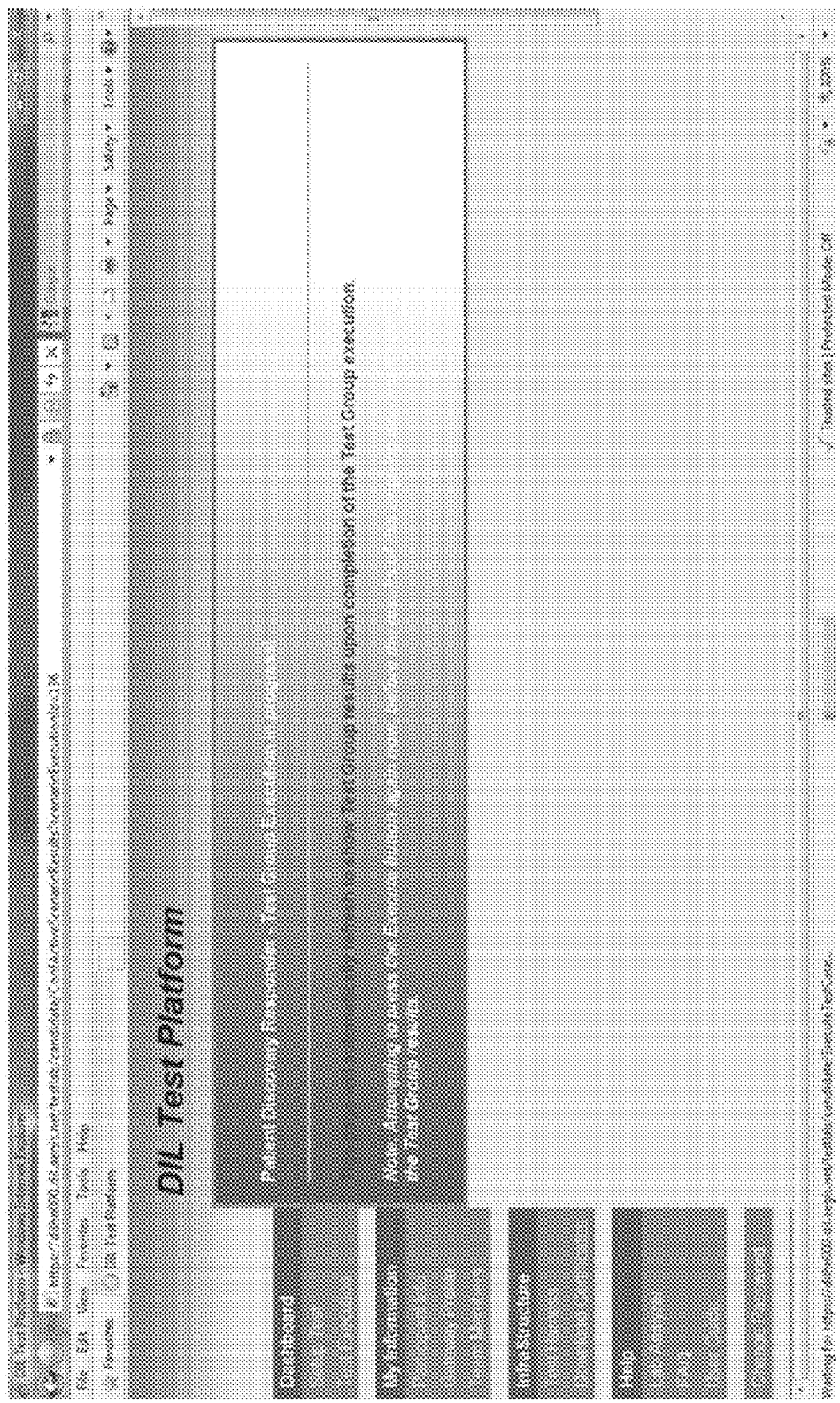

When the participant system is the Responder (FIG. 24), the user does the following for each test scenario: 1) the user runs the PD tests before running the QD or RD tests; 2) when the User runs the PD tests, the DIL populates the Patient ID field; QD and RD tests need these parameters prior to running; 3) clicks on "Execute Test Scenario" for the test case, which triggers the DIL to initiate requests and collect results. The user confirms execution of a responder test case by clicking on the "Execute" tab, and then clicking "OK" to confirm. Once confirmed, a screen showing that the test is in progress is displayed (FIG. 25).

Figure 26:
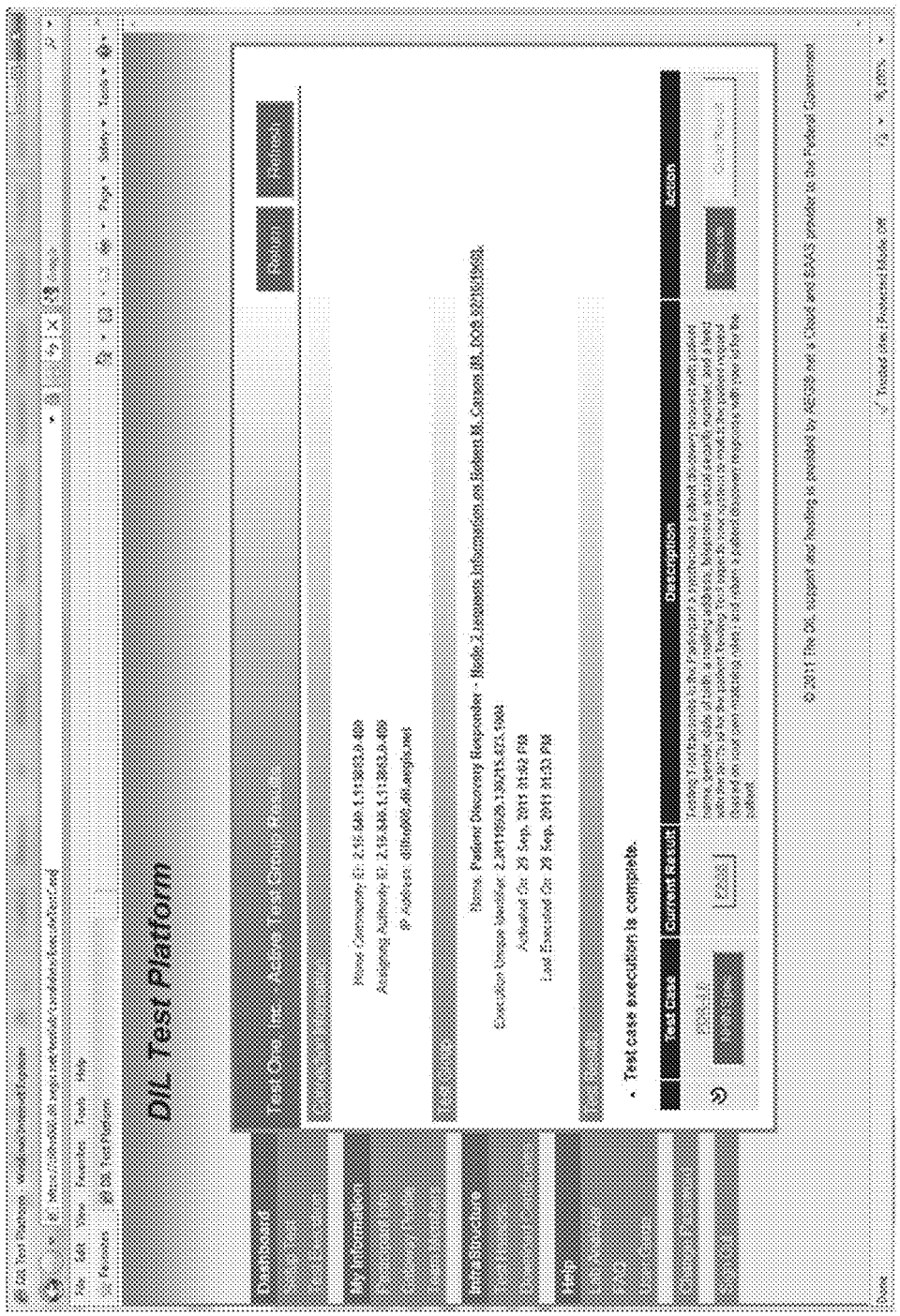

While the tests are running, the DIL populates live results as it receives messages. The DIL parses and reviews audit logs periodically (e.g., every two minutes) to correlate and populate test results within a given test case (FIG. 26). By clicking on "Refresh", the DIL updates the Current Result field on the screen. The status of each test may be identified (e.g., not yet started, in progress (typically the DIL is waiting for a response or an incoming message), success, failure, or requires external validation).

Figure 27:
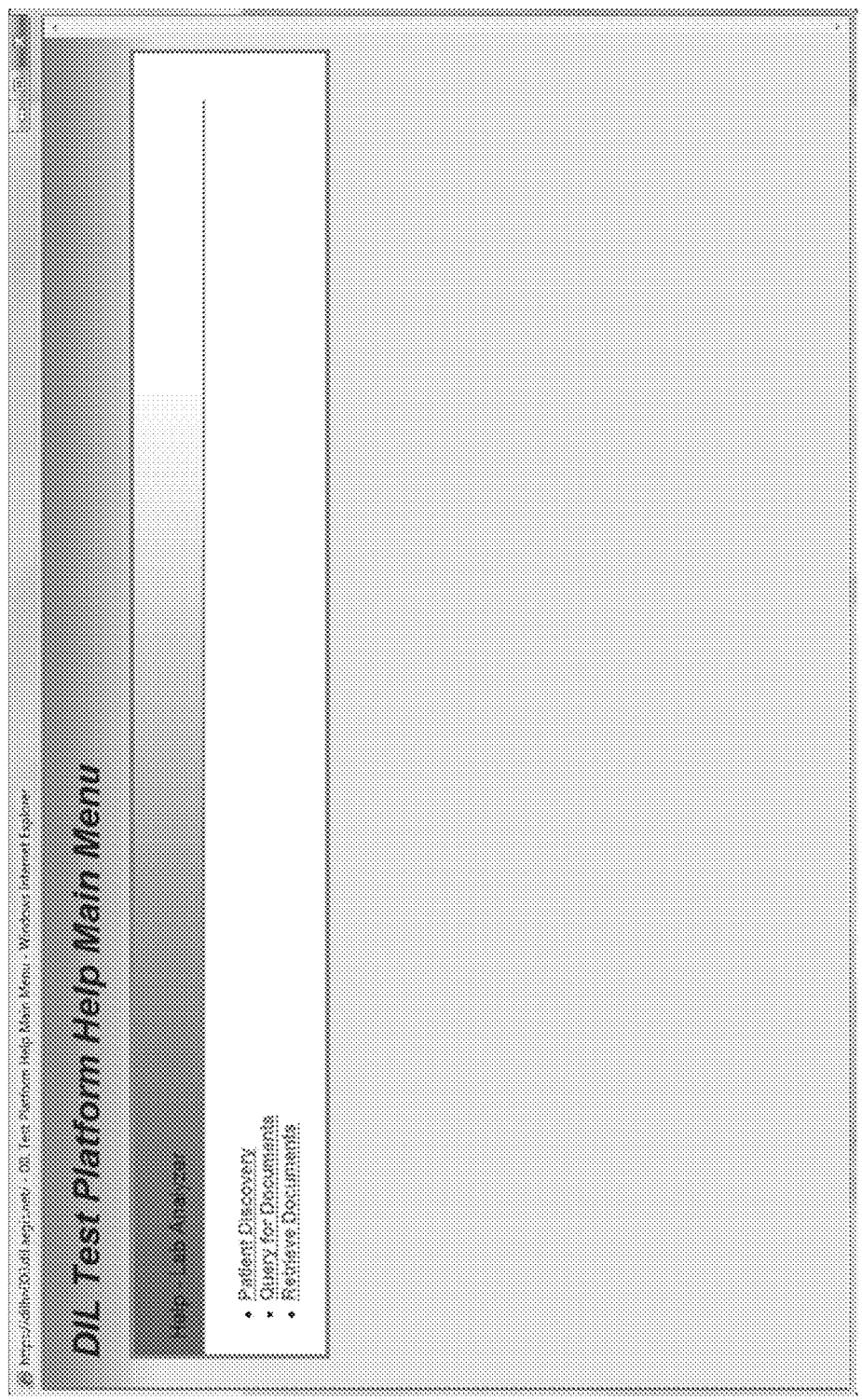
Figure 28:
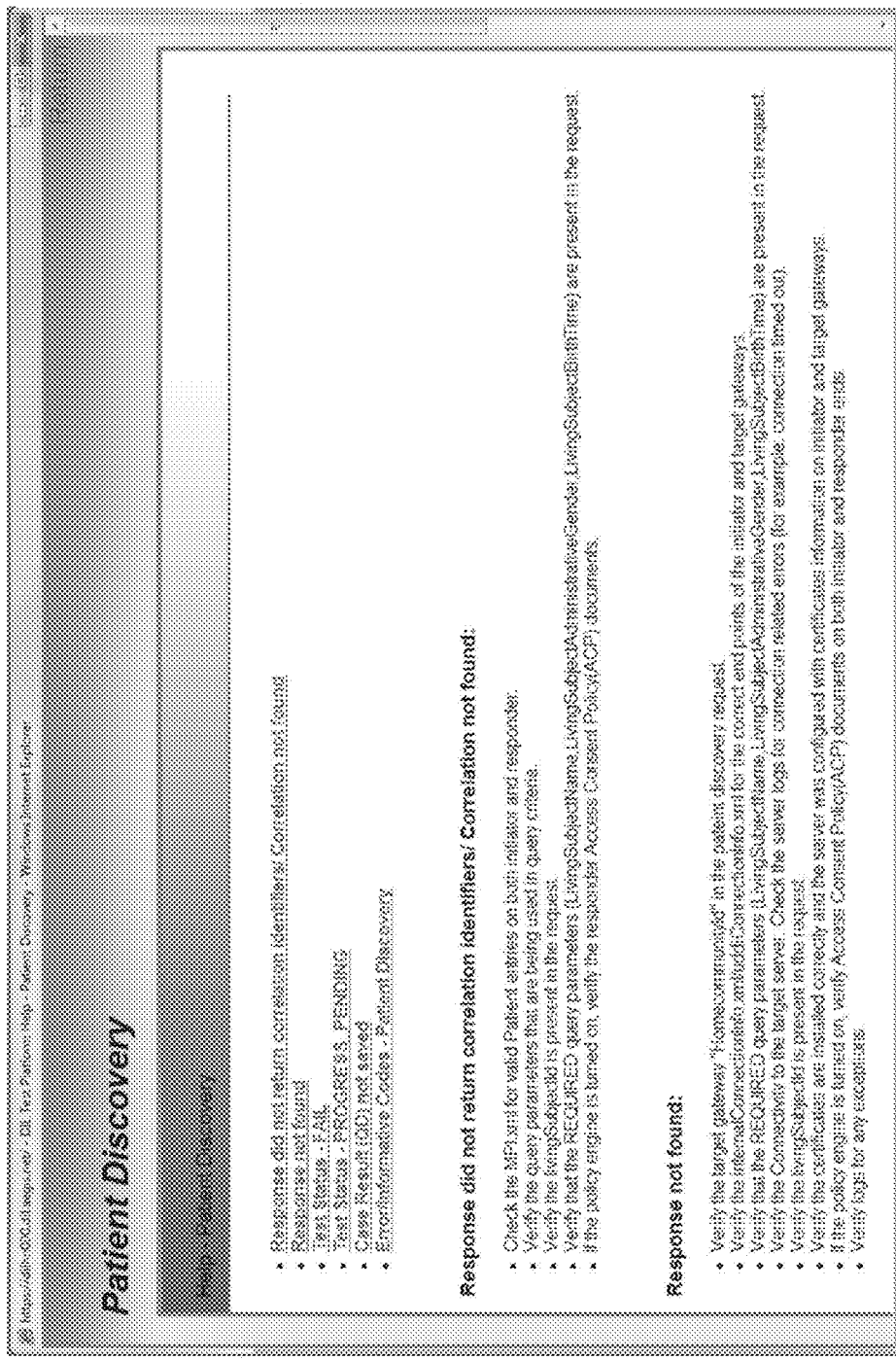
Figure 29:
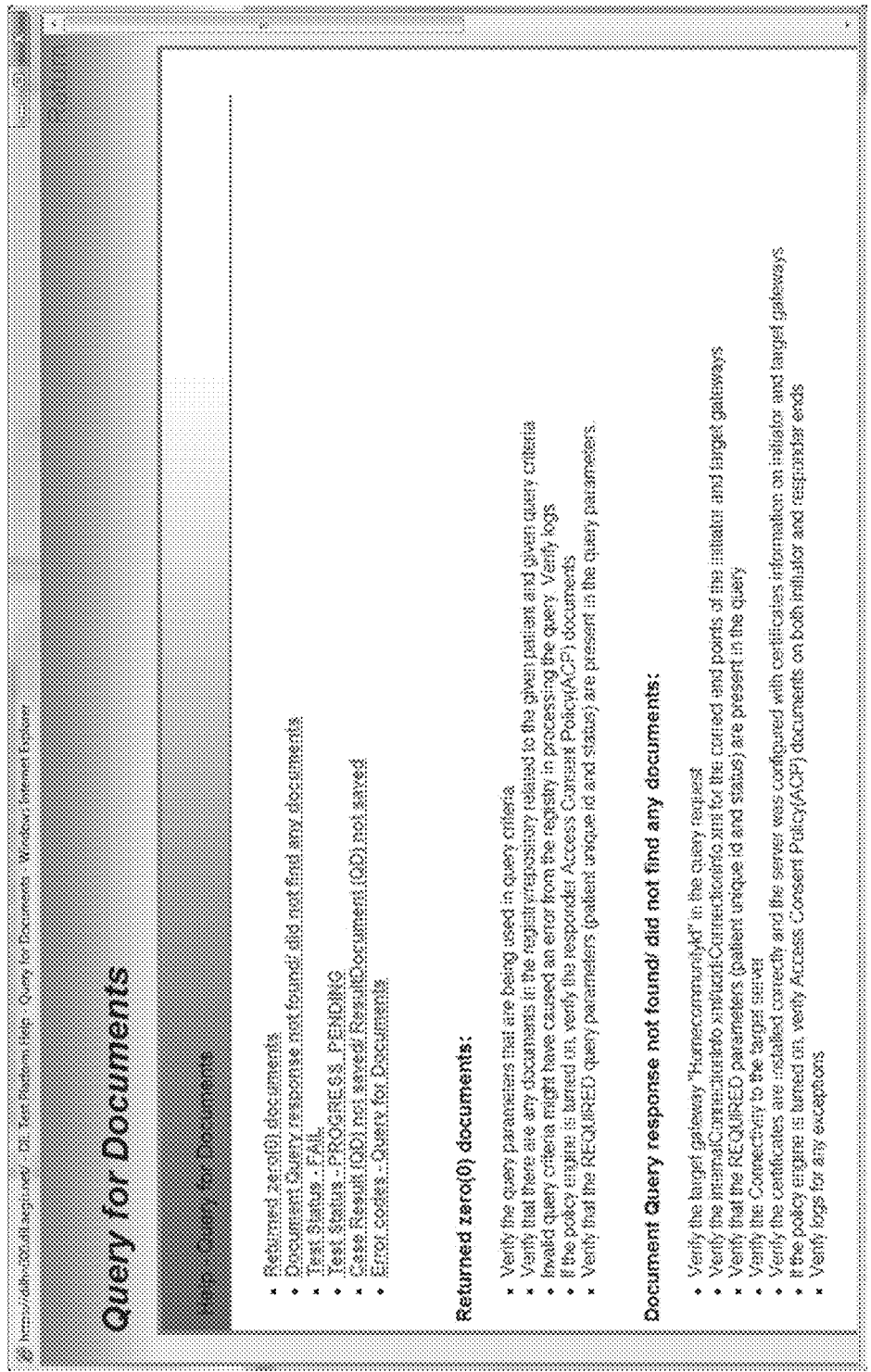

The user may click on the "Lab Analyzer" under the Help section (see FIG. 26), which brings up a pop-up window that links to specific troubleshooting information for PD, QD, and RD testing information (FIG. 27). Thus, the user may easily refer to such troubleshooting information if any problems arise when executing the test case.

Figure 30:
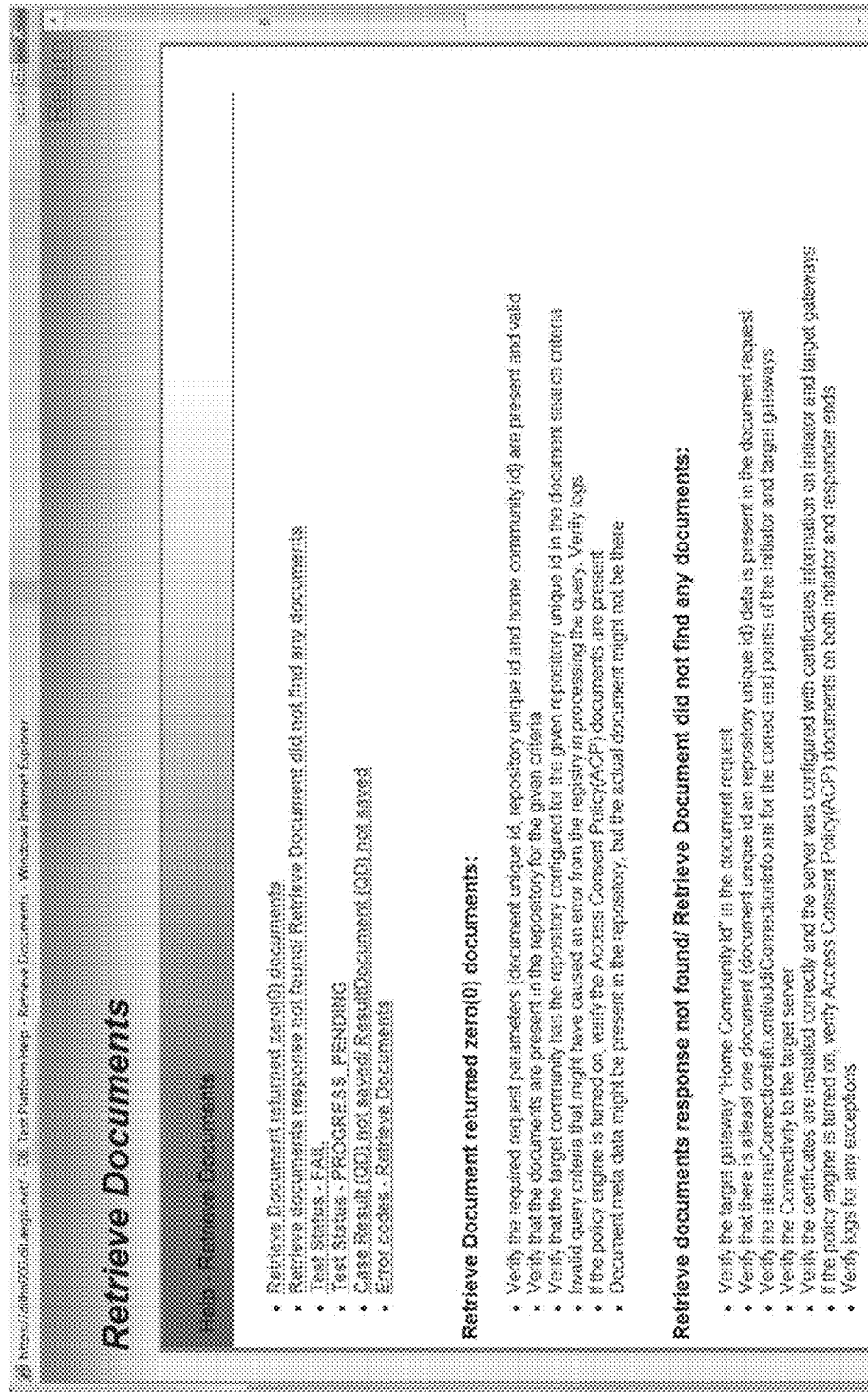

Additional information may be presented to the user via additional screens: a Lab Analyzer Patient Discovery screen displays patient discovery details (FIG. 28); a Lab Analyzer Query for Documents screen displays query for documents results (FIG. 29); and a Lab Analyzer Retrieve Documents screen displays retrieve documents results (FIG. 30).

Figure 31:
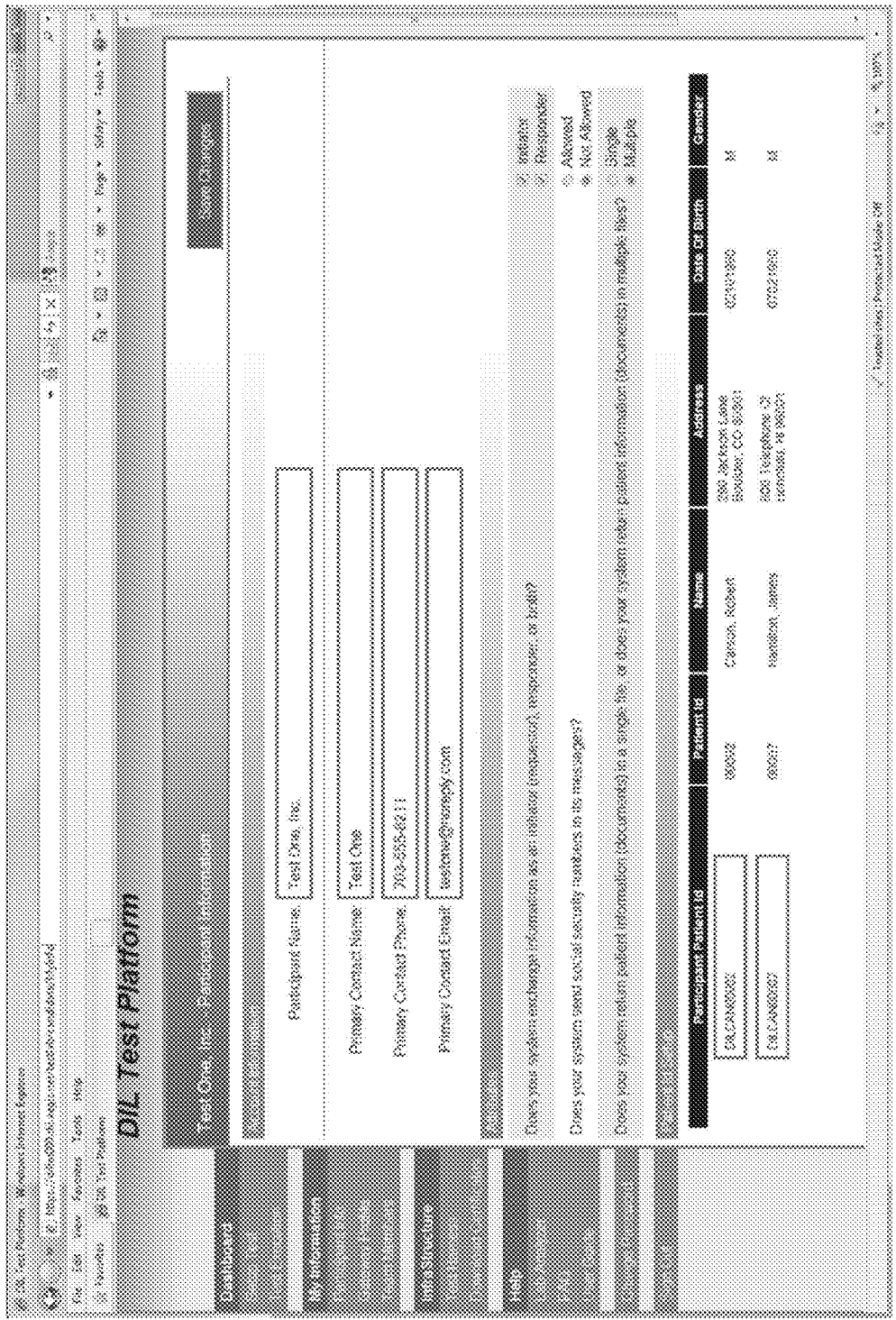

A Participant system's information may be viewed and/or edited in a Participant Information screen (FIG. 31). Under the "Account Information" section, the participant system's contact information is displayed. Under the "Attributes" section, default settings for test configuration attributes are displayed and/or may be set, such as social security number (SSN) handling, initiator or responder status, and patient document information. However, these attributes may vary per test case.

Figure 32:
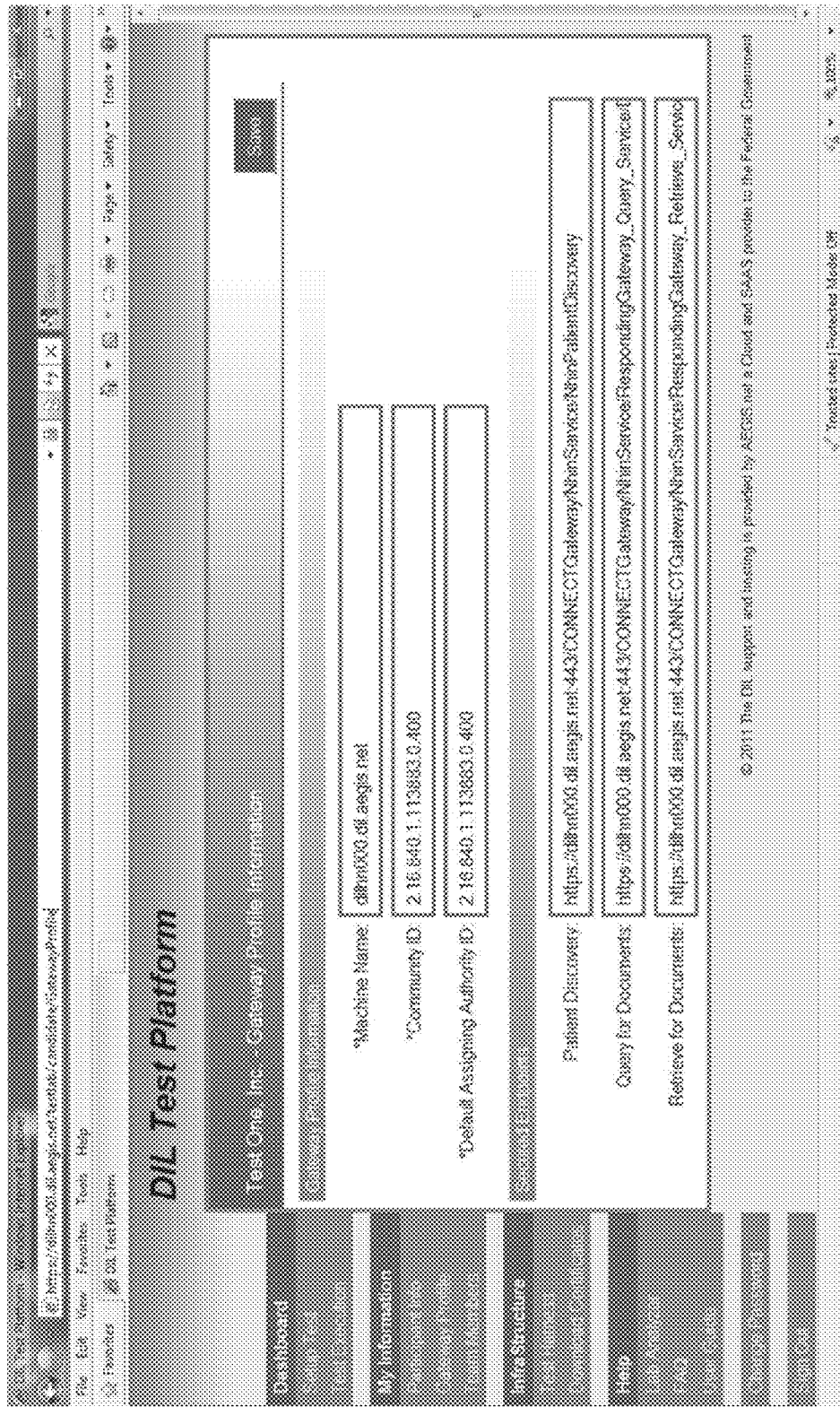
Figure 33:
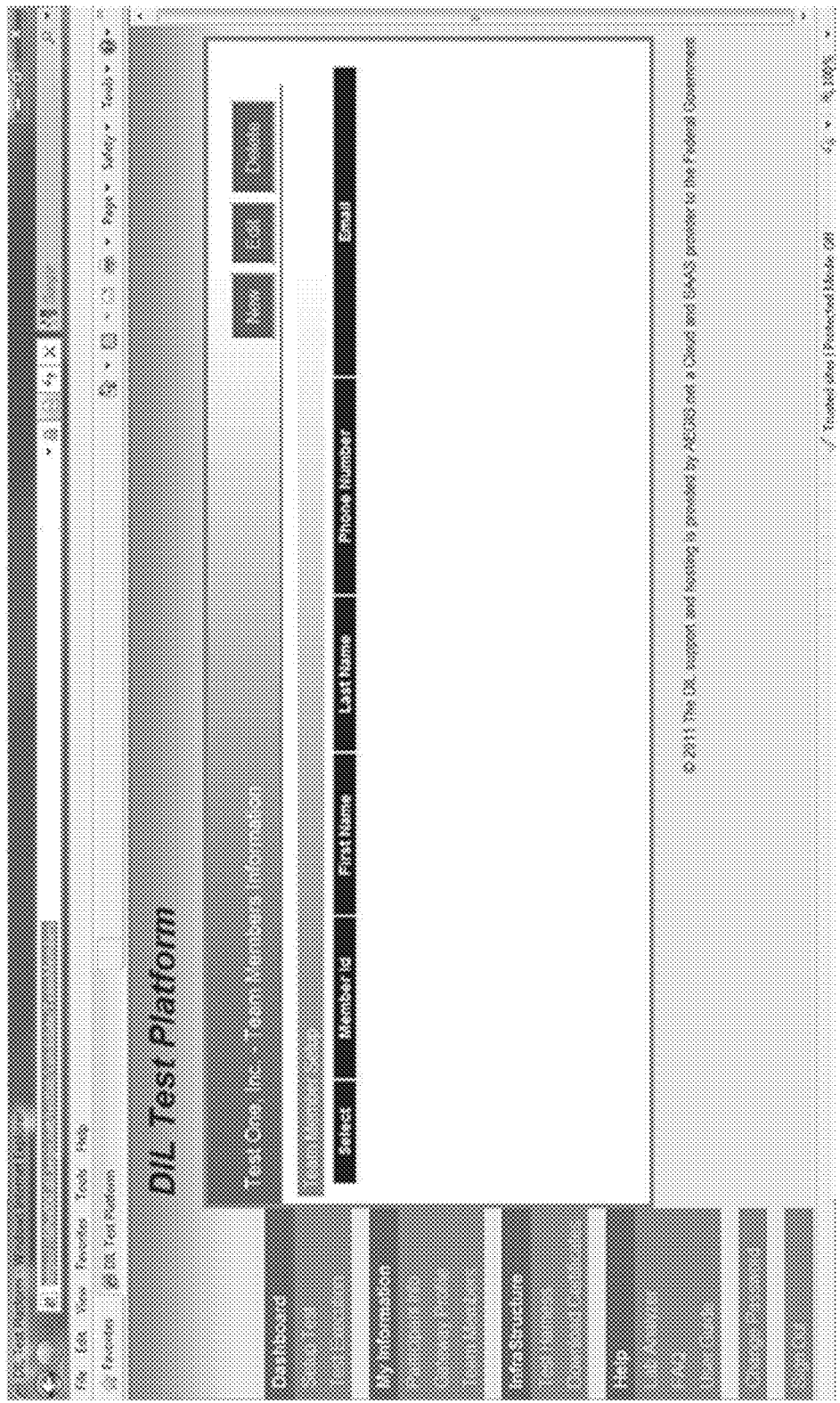

A Gateway Profile screen displays gateway profile and secured endpoint information (FIG. 32). A Team Members Information screen displays team member setup information, and allows participants to list team members associated with test case execution activities (FIG. 33). Numerous team members may be provided for one participant.

Figure 34:
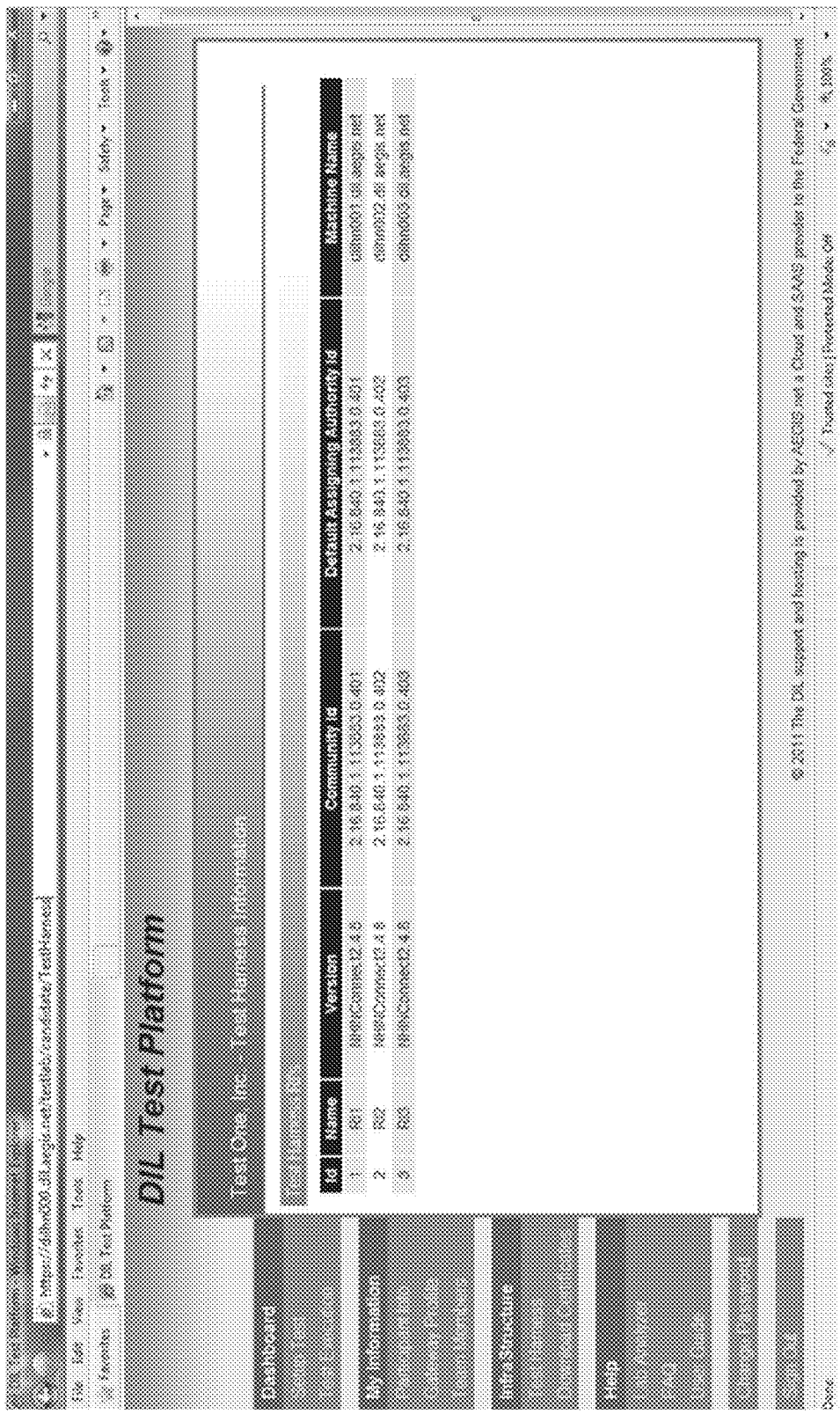
Figure 35:

A Test Harness Information screen displays the reference implementations, community identification, assigning authority (AA), and machine name for the DIL Test Harness (FIG. 34). A Frequently Asked Questions (FAQ) tab navigates the user to a screen with links for additional information. A Change Password screen permits a user to change their password.

EXAMPLE 4

Dynamic Test Cases

Dynamic test cases are defined in the system via templates. A variety of system templates may be provided, including for example templates for Patient Discovery (PD), Query Document (QD), and Retrieve Document (RD) messages. Support for other message types may also be provided as desired. Users may utilize the system templates as a starting point for creation of their own templates. Users can then reuse the templates in test case definitions and override various settings through a user-friendly web interface.

Referring to FIGS. 35-42, a User may navigate to a Manage PD Templates screen by clicking a "Case Templates" tab. The Manage PD Templates screen displays a list of defined templates. The User can filter the templates by message type (PD, QD, RD, etc.), template name, description, etc. Templates can be deleted if they're no longer needed.

Figure 36:
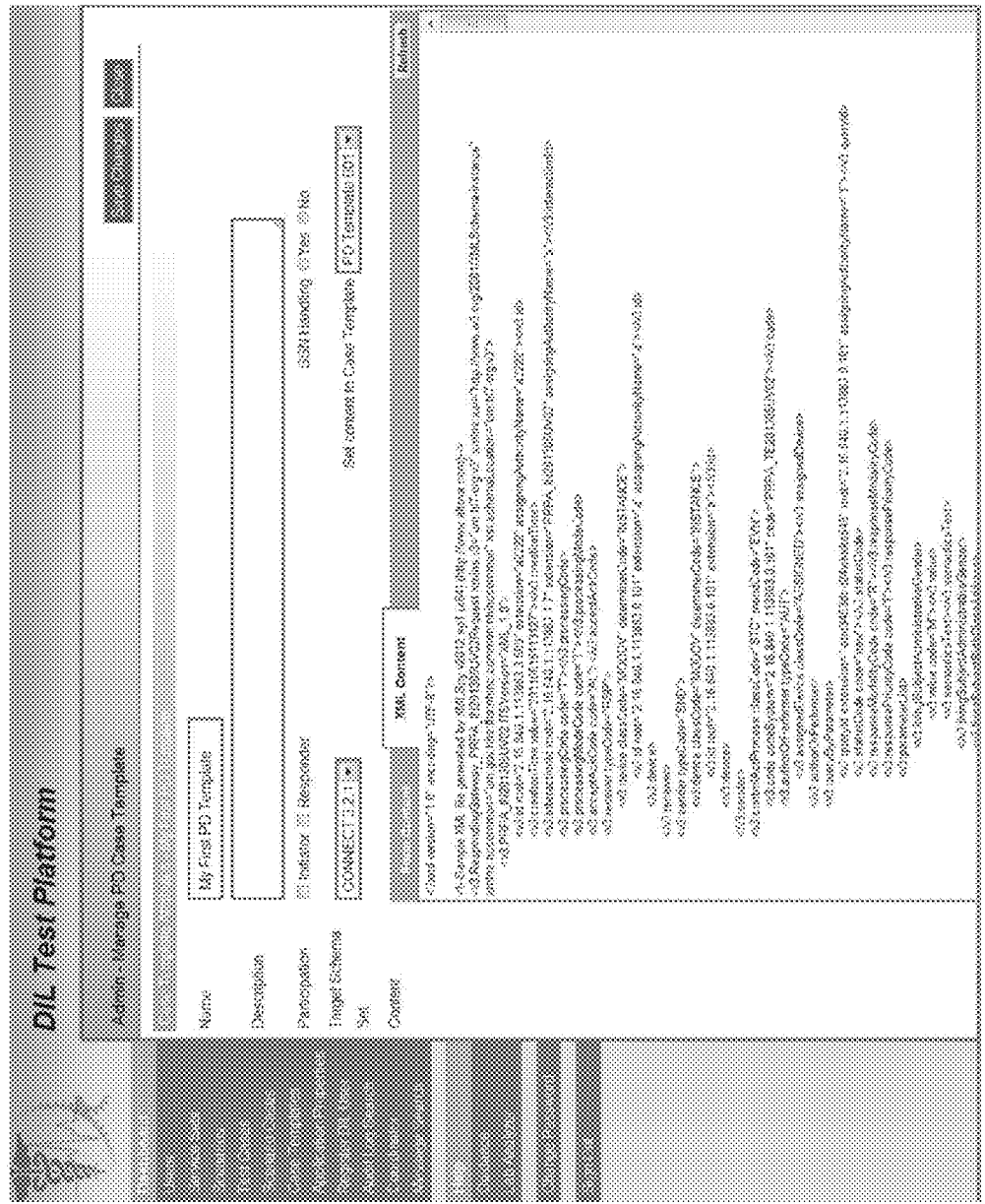

Templates may also be created. The user can define Patient Discovery messages using raw XML. By default, when the user clicks on "New Template" tab (FIG. 35), the system navigates the user to XML view of the template definition (FIG. 36). The template XML can be validated against different schema sets which are in turn defined by NHIN and other Health IT specifications. The user can base the template XML on another existing template by using the "Set Content to Template" drop-down menu. The system will not save the template unless it has been validated successfully against the specifications.

Figure 37:
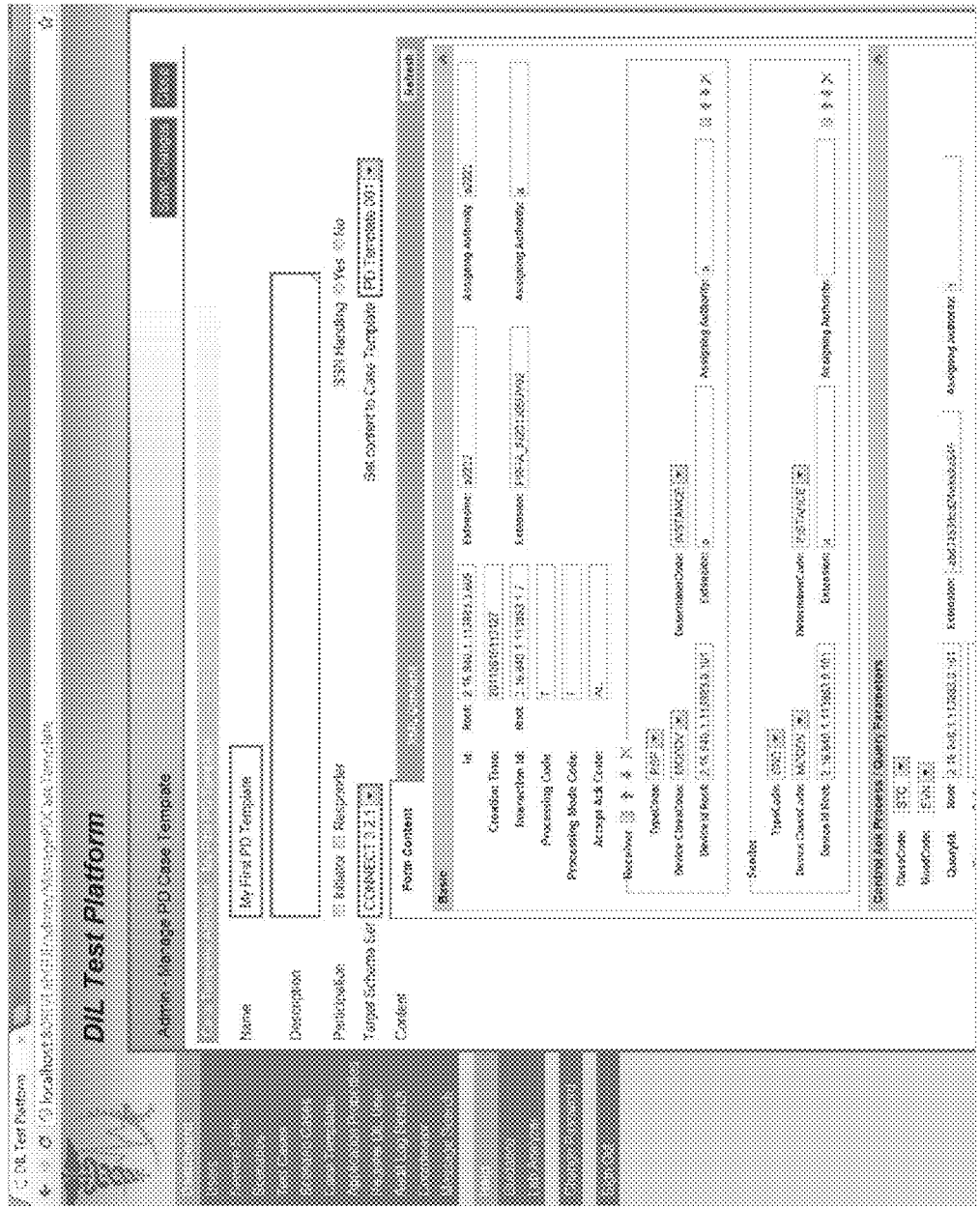

The user may edit the raw XML in XML view or navigate to the Form Content tab (FIG. 37). Changes on the two tabs are synchronized with each other. In the Form Content display screen, content is broken down into different sections (e.g., Basic, Control Ack Process, etc.).

Figure 38:
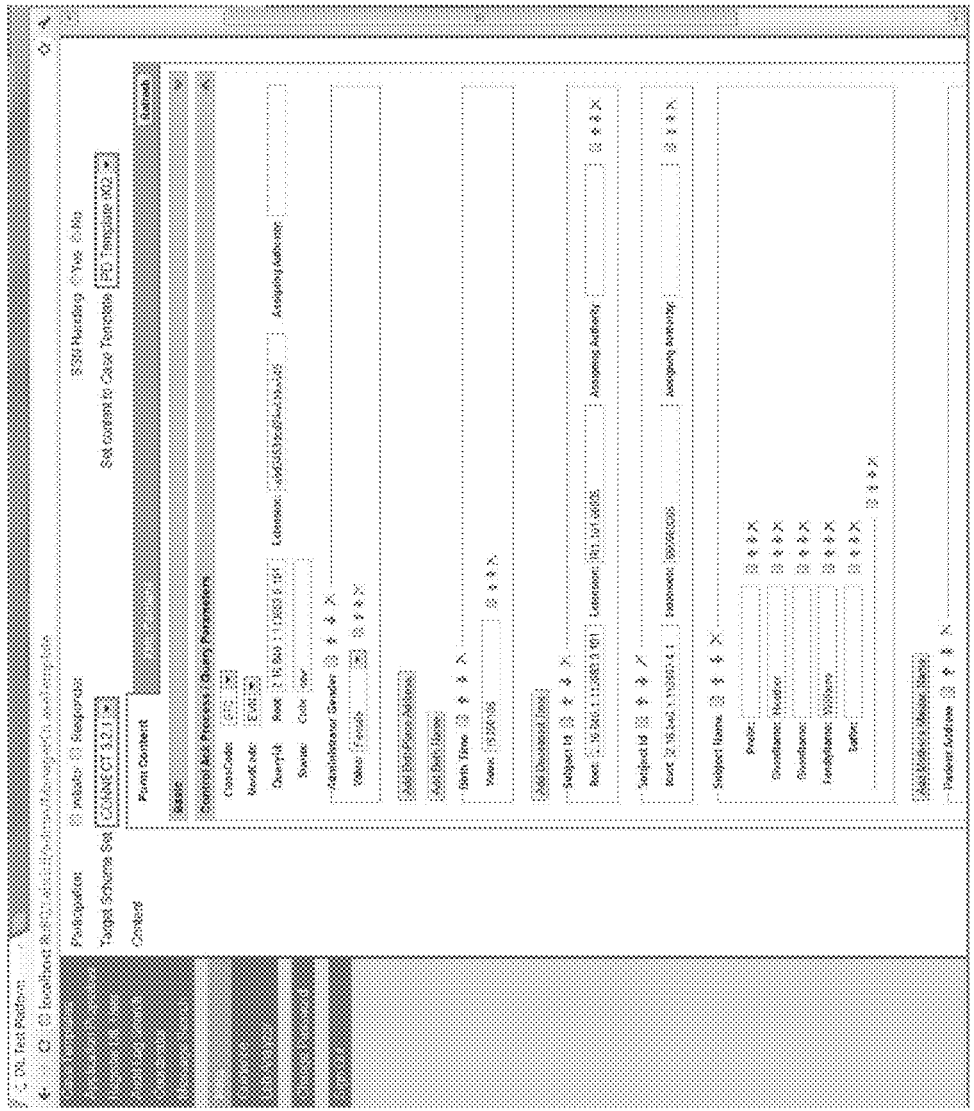

A User may click on the header of a section (e.g. "Basic") to toggle/minimize the section for an enhanced or better view of subsequent sections (FIG. 38). Validation against specifications and setting the content to a different template are supported in the Form Content screen just as they are on XML view. When the user revisits an existing template, the system will remember the last display (Form or XML) and section the user was viewing, and navigate the user to the same tab and section the user was on previously.

Figure 39:
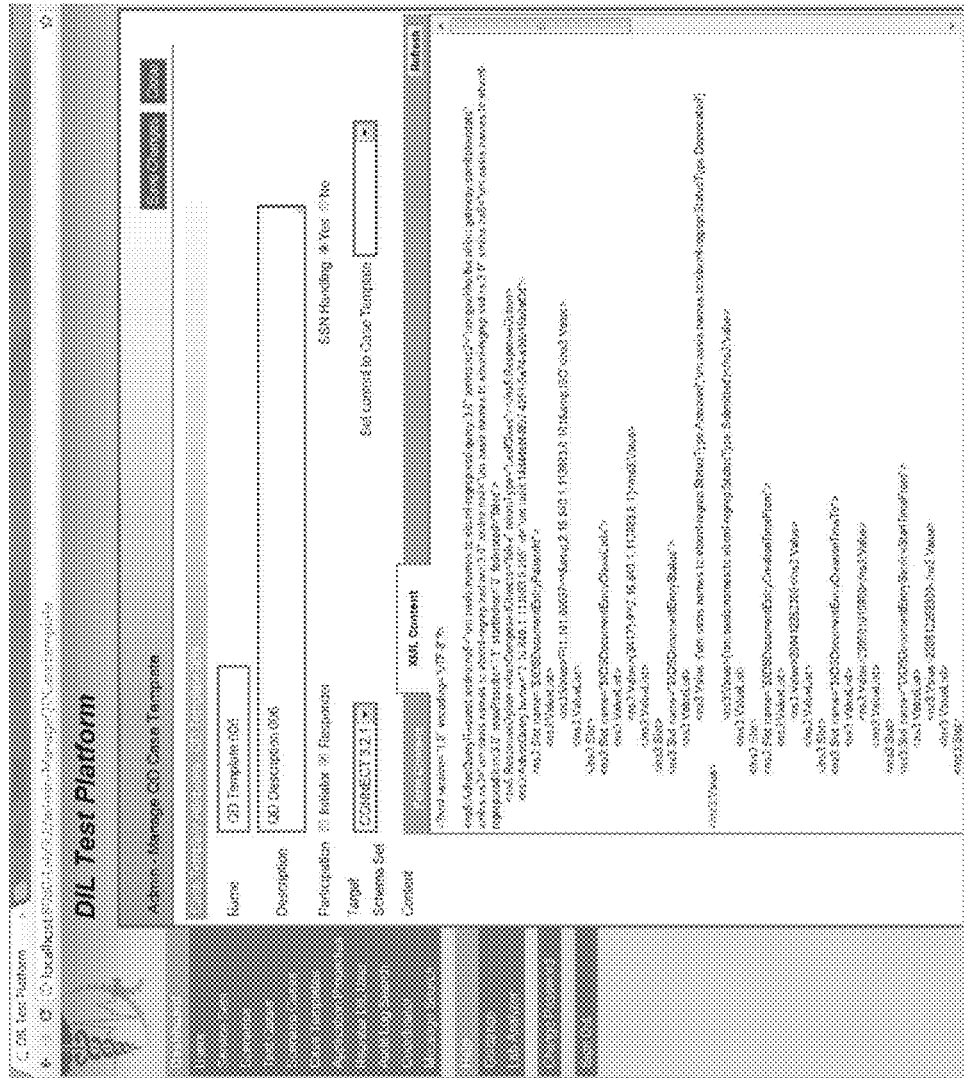
Figure 40:
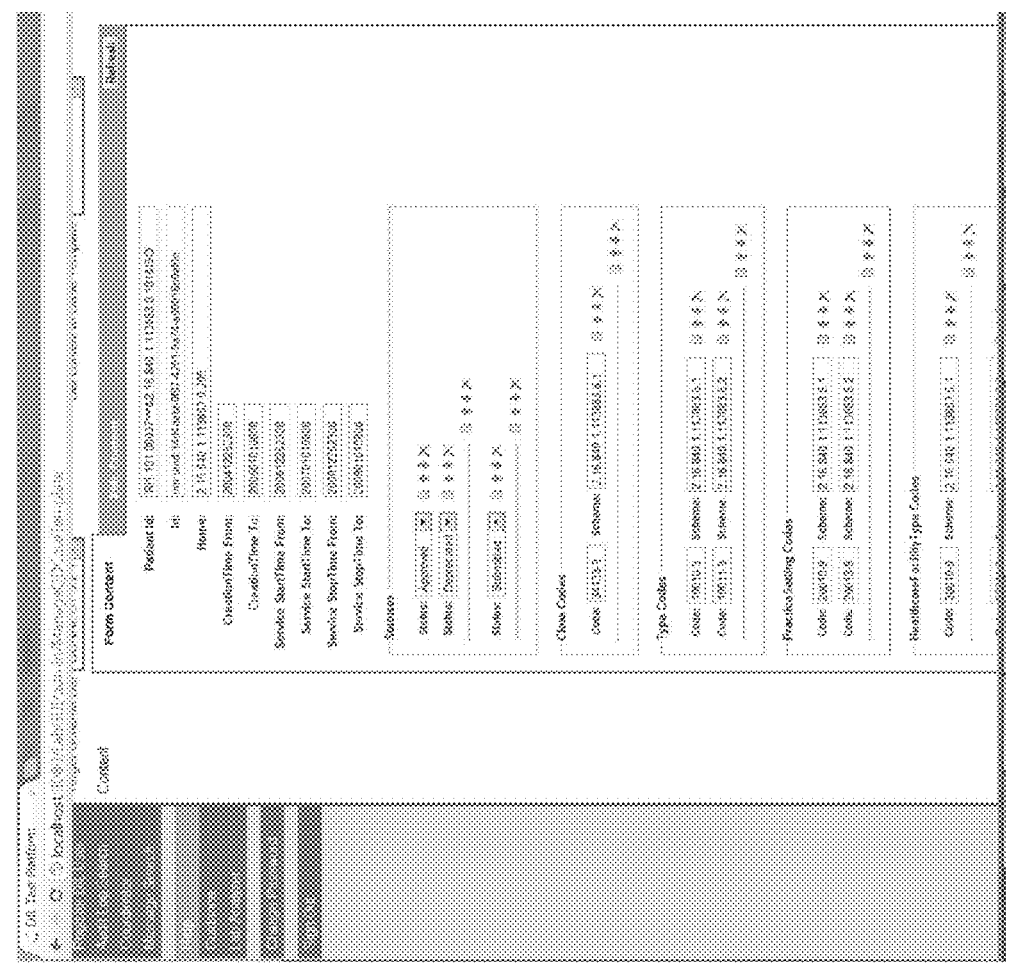

QD templates are defined and edited in a similar way as PD templates. XML and Form Content displays for an existing QD template are shown in FIGS. 39 and 40, respectively.

Figure 41:
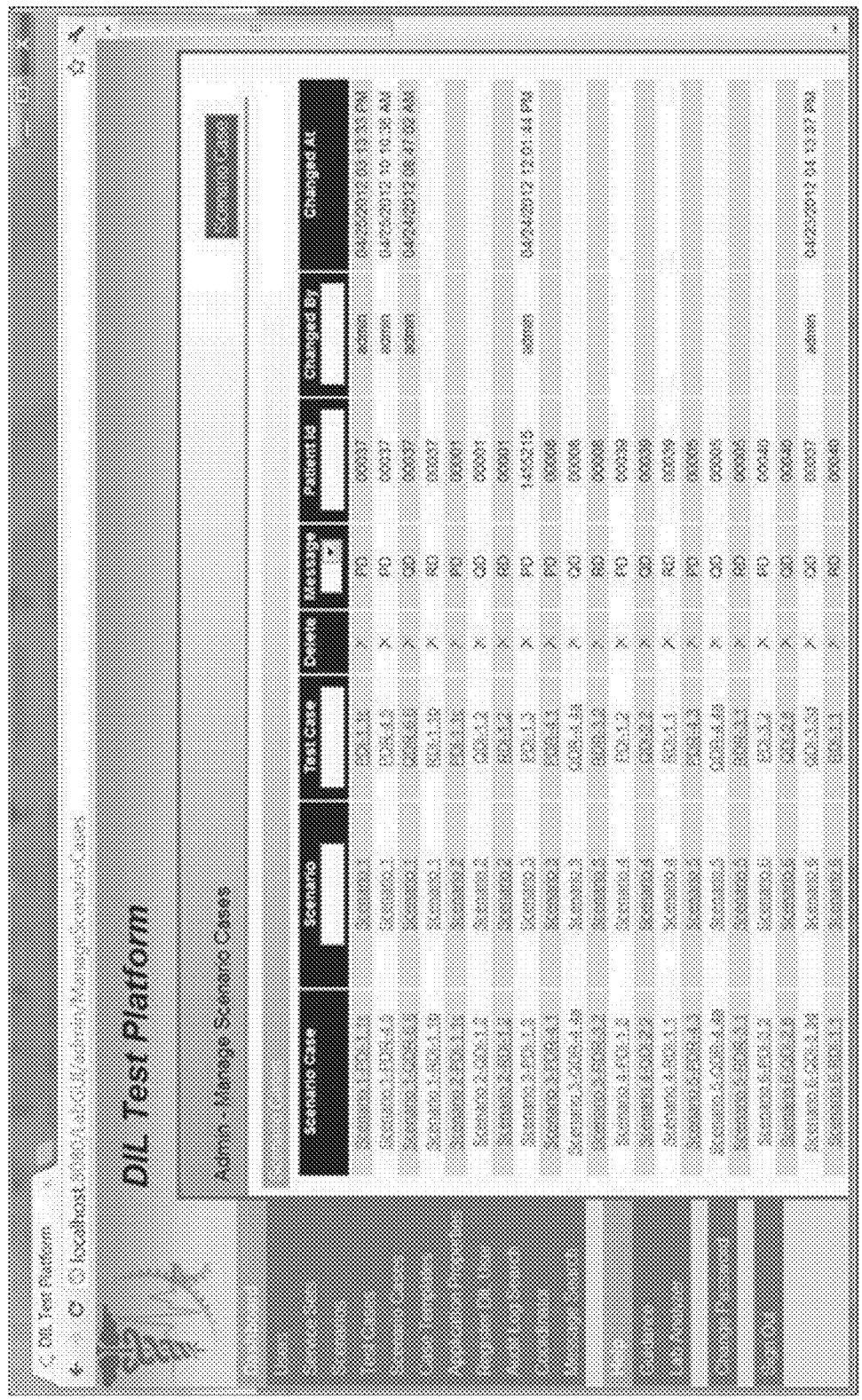

A user may view a listing of all defined scenario cases using the Scenario Cases menu link (FIG. 41). The User may filter the scenario cases by message type (PD, QD, RD, etc.), scenario name, test case name, etc. Scenario cases can be deleted if no longer needed.

Figure 42:
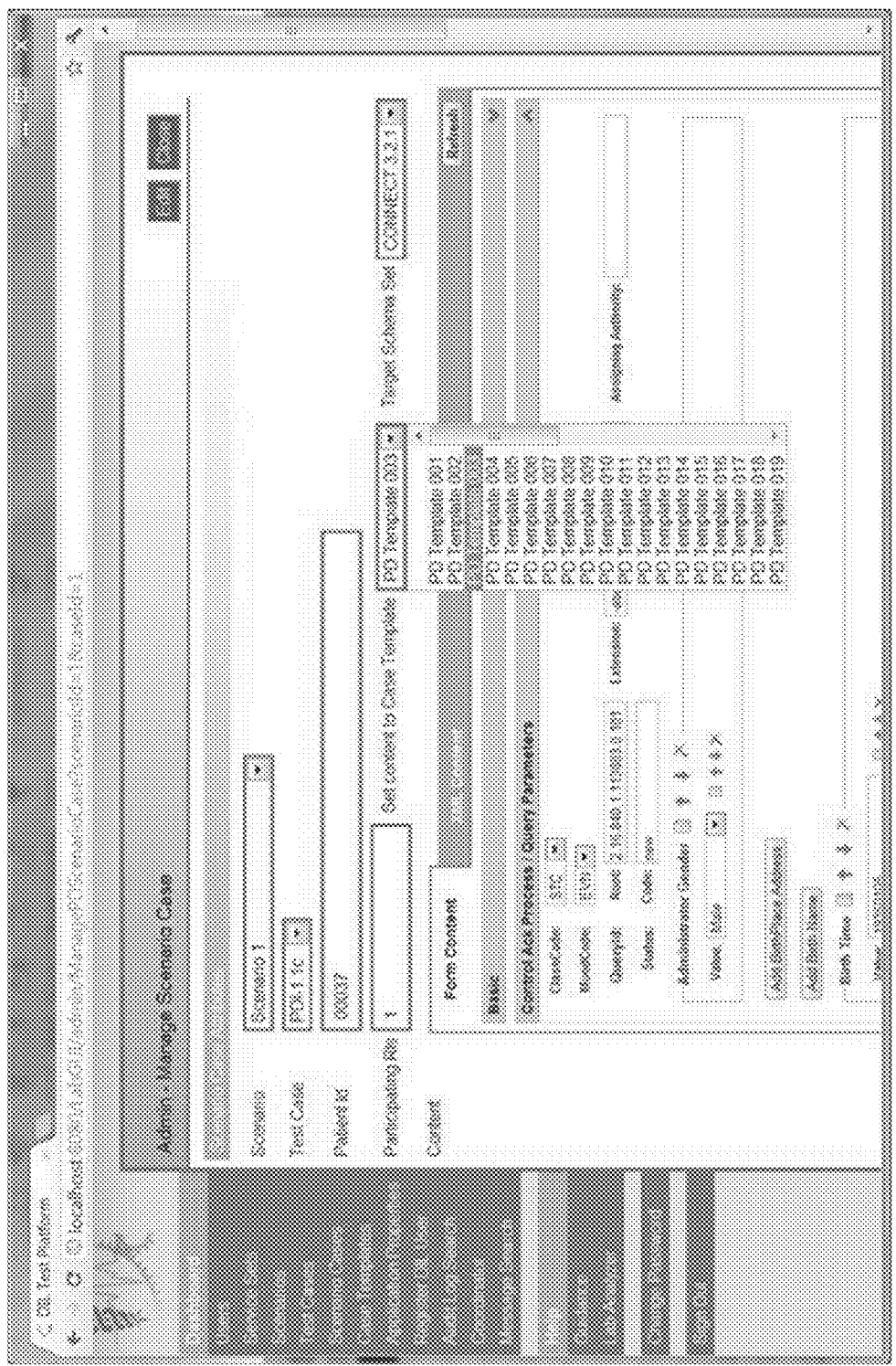

Scenario Case or Test Case definitions can be based on existing templates or can be defined ad-hoc. A User may set the content of a scenario case to an existing template (FIG. 42). XML validation against different schema sets and modification of a case definition via a Form are supported in Scenario Case definition screens, similar to the Case templates. Patient Discover, Query Document, and Retrieve Document are supported. Support for other message types may alternatively or additionally be provided.

Figure 43:
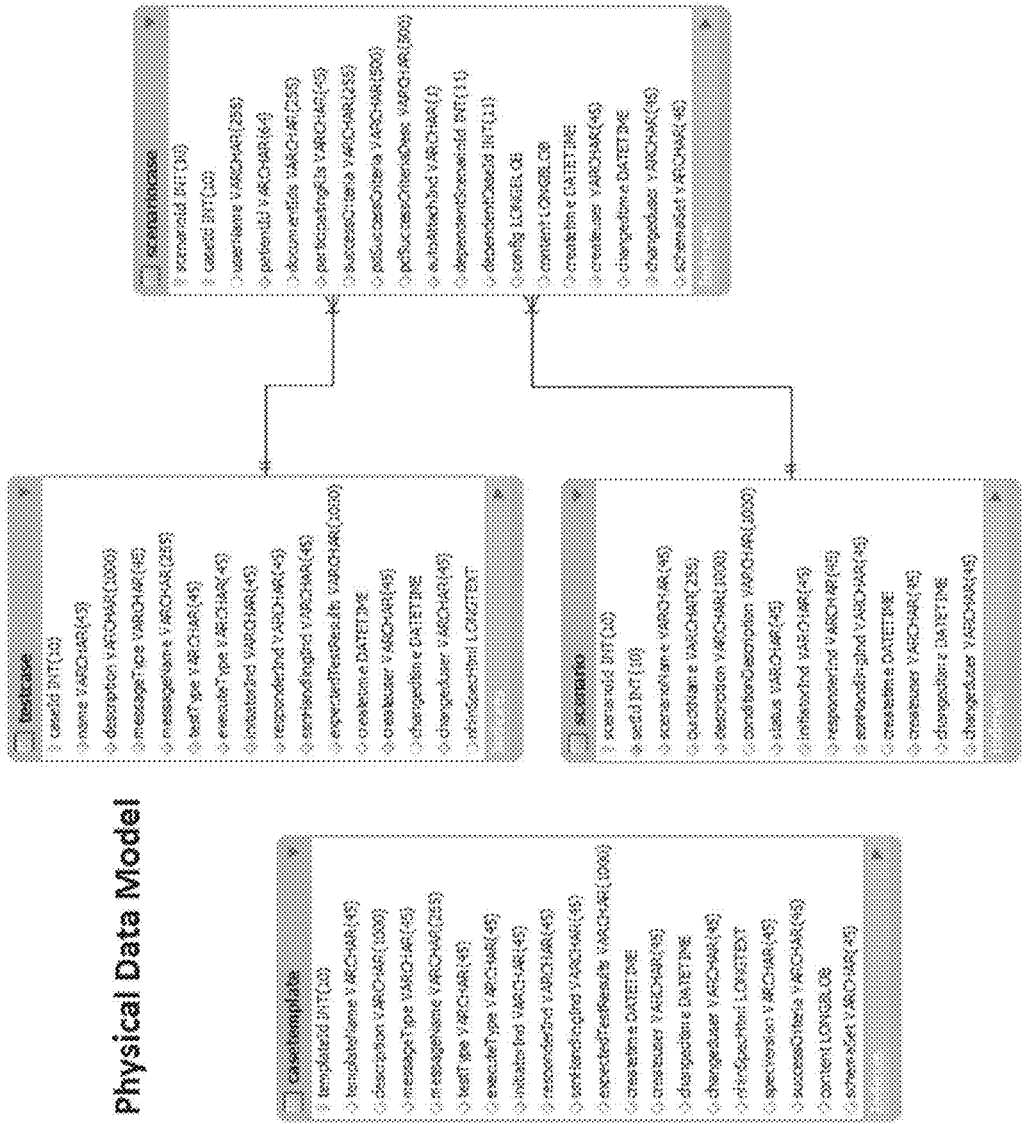
FIG. 43 illustrates a case template table according to embodiments of the present invention.

Case templates are stored in the case template table as raw XML (FIG. 43). The schema set that the content was validated against is stored as well. The Scenario Case definition preferably does not maintain any references to the template it was based on originally to avoid the user overriding the content dramatically and the Scenario Case content that is ultimately saved could be completely different from the template it started out with. The system uses Scenario Case definitions to communicate with Gateways, and not Case templates.

Figure 44:
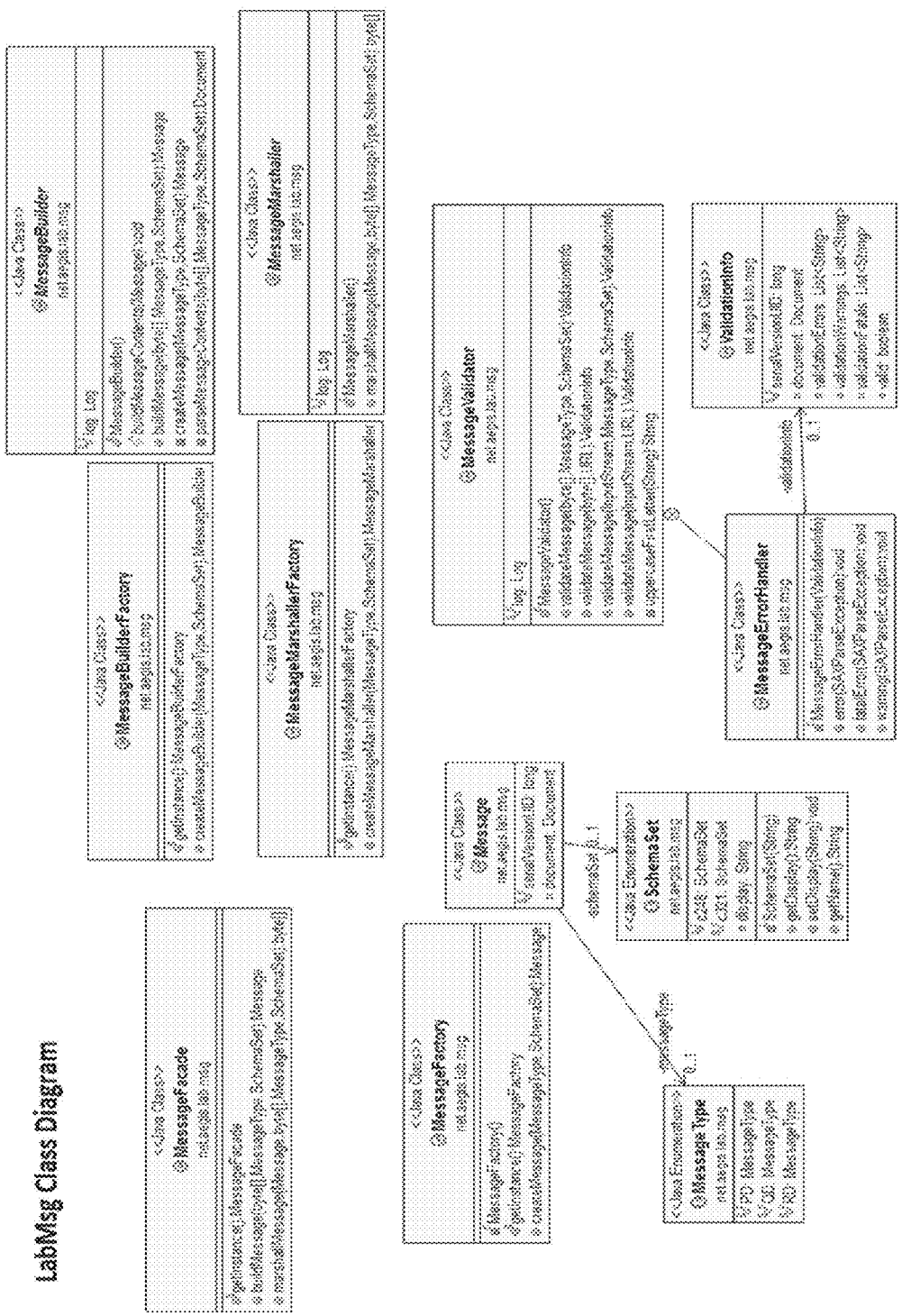
FIG. 44 illustrates a schematic diagram of top-level classes in the LabMsg module according to an embodiment of the present invention.
Figure 45A:
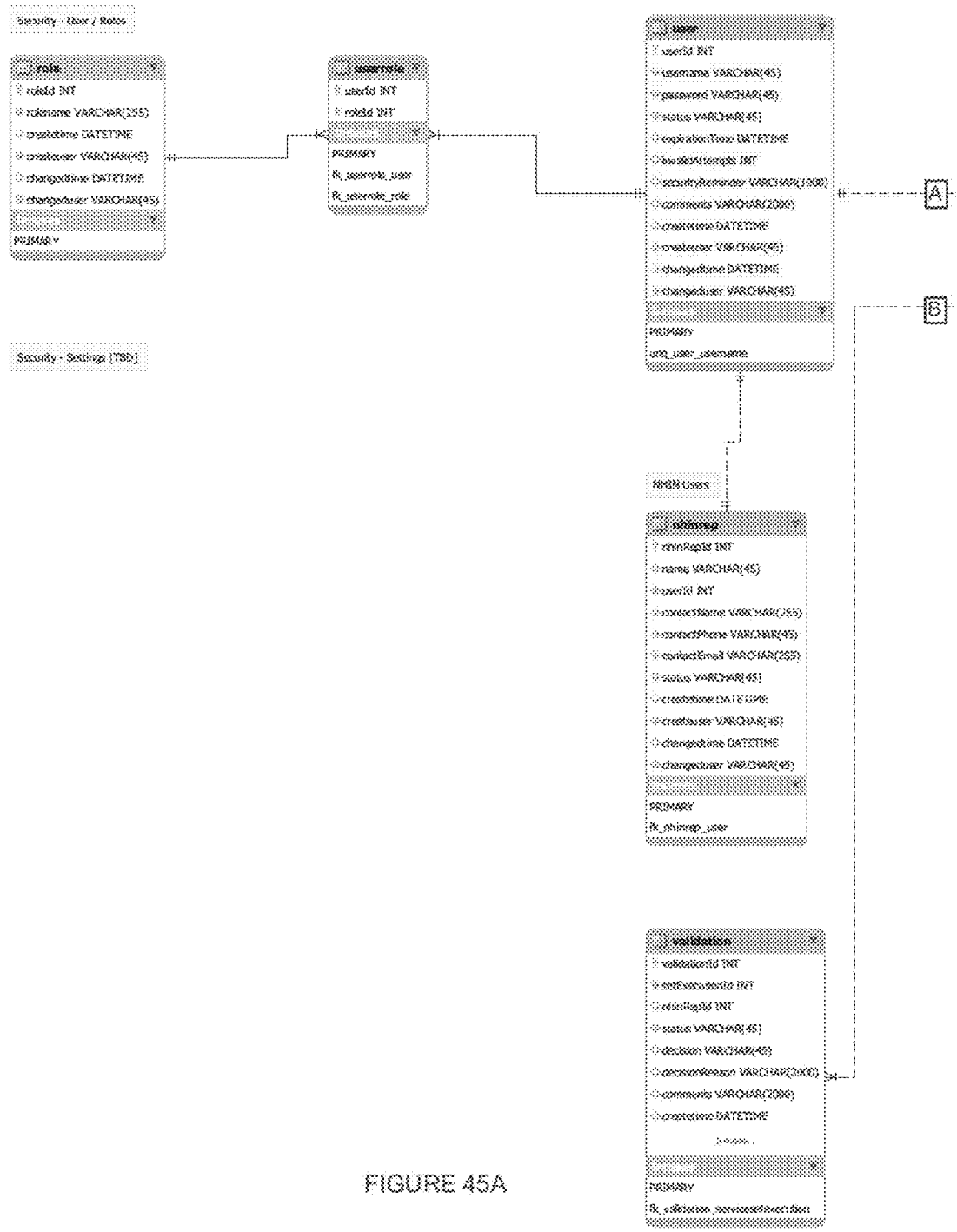
FIG. 45A-E illustrates a schematic diagram of a database model for the DIL according to an embodiment of the present invention, showing tables used in the backend MySQL for the DIL.
Figure 45B:
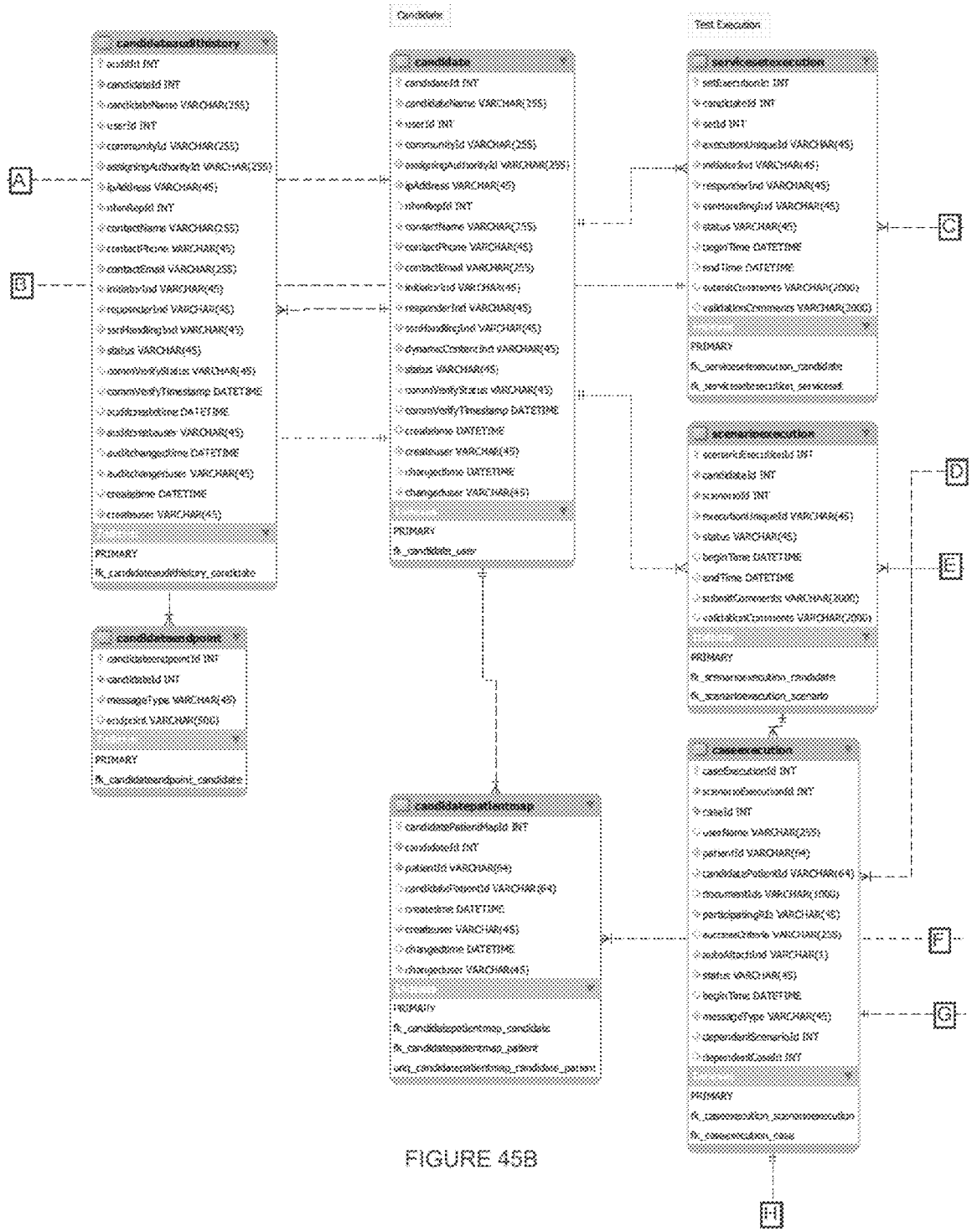
Figure 45C:
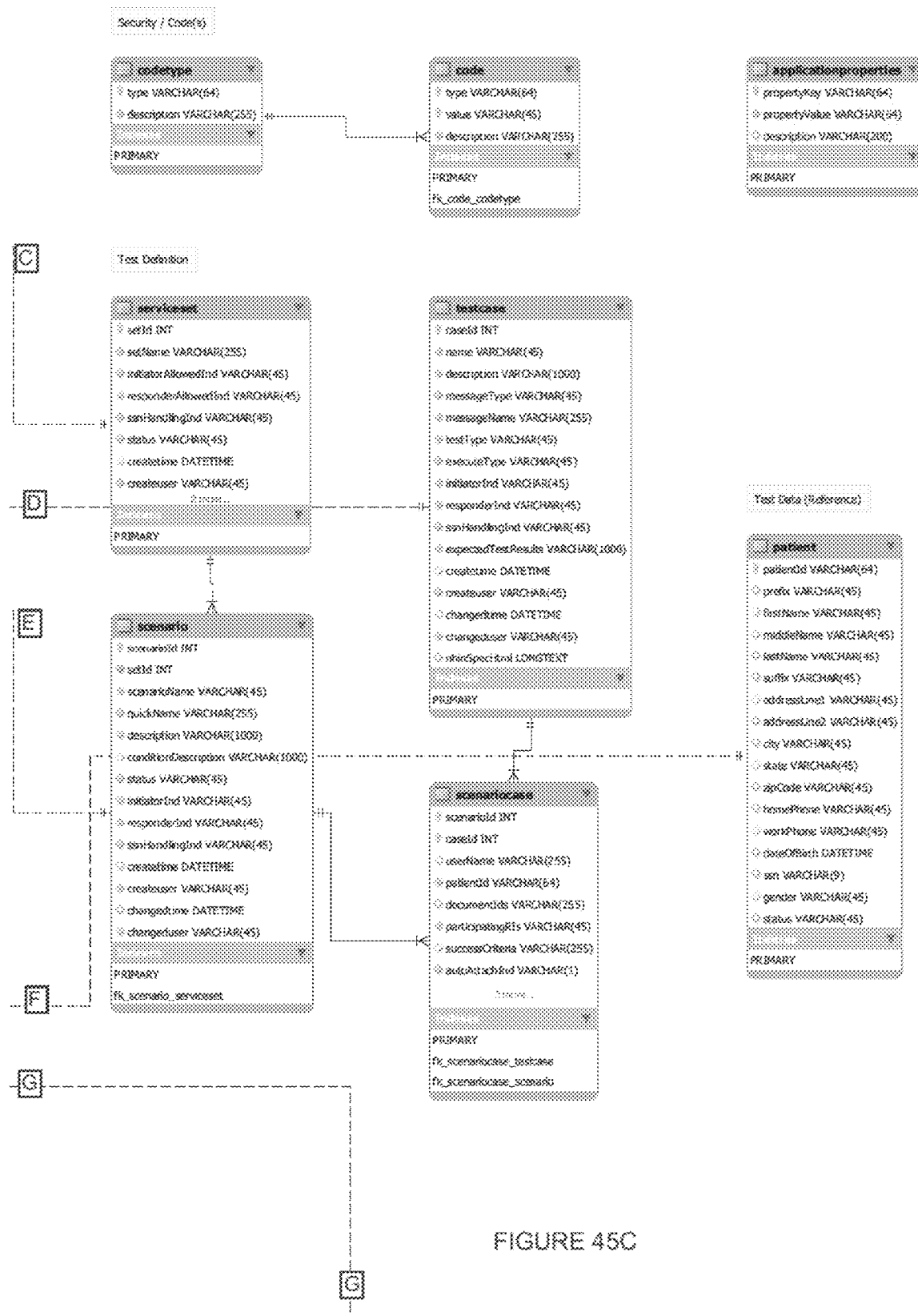
Figure 45D:
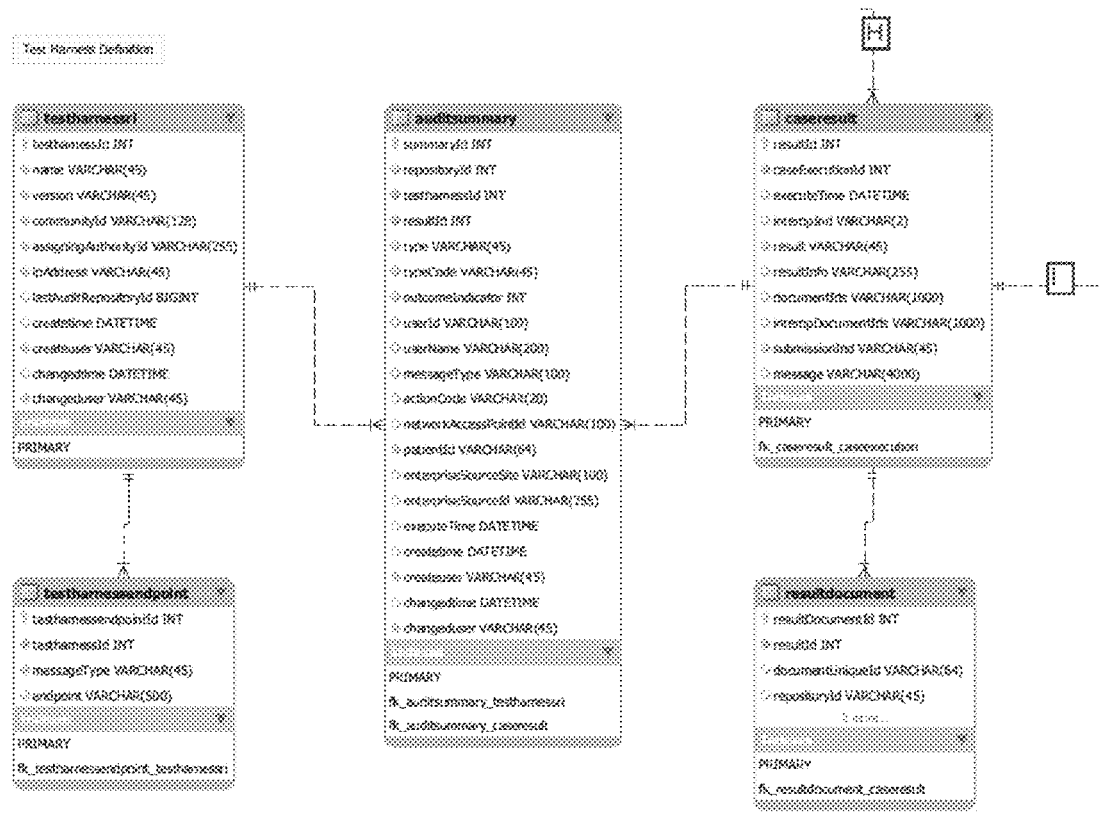
Figure 45E:
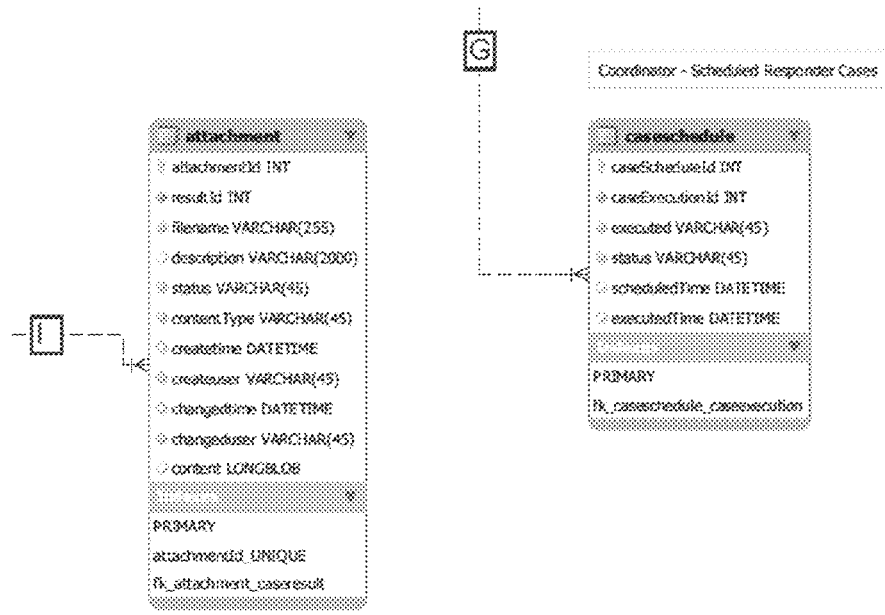

LabGUI utilizes the LabMsg module to perform the following functions: Validation of template and case definition XML content; Unmarshalling of XML content into Message to be used by user interface; and Marshalling of user modifications on the Form view to XML. The top-level classes in the LabMsg module are shown in FIG. 44.

The Dynamic Test Cases feature has been implemented in various modules. The technologies utilized in each of the modules is shown in Table V below. All technologies listed below are open-source.

TABLE V

| | |
|---|---|
| LabMsg | The module is implemented in Java.<br>Dom4j is used for XML parsing, validation, DOM manipulation, and marshalling.<br>Apache Commons is used for various utility functions.<br>JUnit is used for testing.<br>Log4j is used for logging. |
| LabGUI | The module is implemented in Java.<br>Struts2 is used as the MVC web-tier framework.<br>jQuery / JavaScript are used to implement some user actions on the browser.<br>Apache Commons is used for various utility functions.<br>Log4j is used for logging. |
| LabCore | The module is implemented in Java.<br>Hibernate is used to persist templates and scenario case definitions to the database.<br>Spring is used for dependency-injection and to manage transactions.<br>Apache Commons is used for various utility functions.<br>JUnit is used for testing.<br>Log4j is used for logging. |

EXAMPLE 5

High Level Architecture for Vendor Participate

Figure 46:
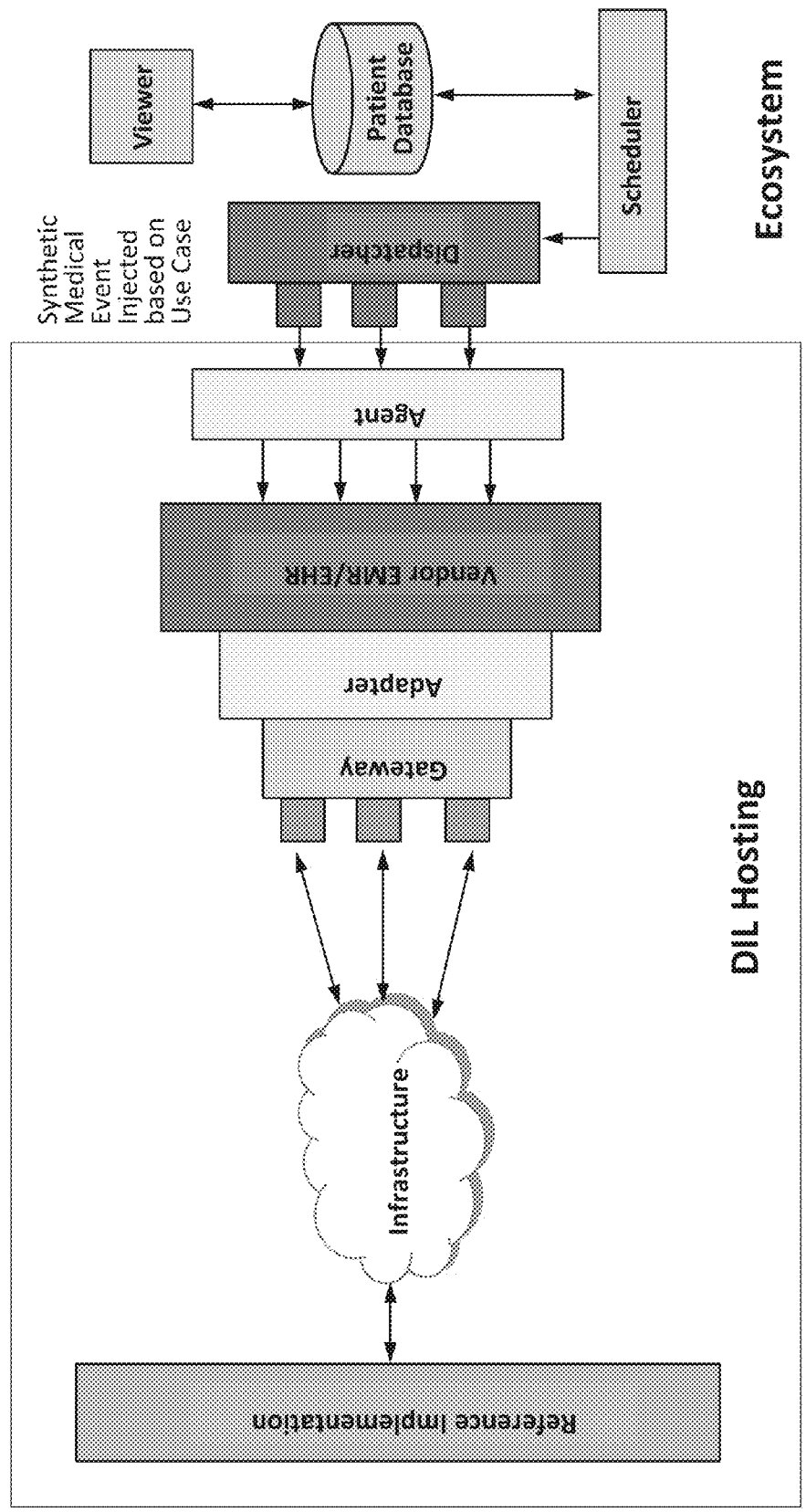
FIG. 46 illustrates a schematic diagram of architecture for vendor participation according to an embodiment of the present invention.

Referring to FIG. 46, a schematic diagram of high level architecture for a Vendor Ecosystem according to the present invention is illustrated. The Ecosystem contains multiple components running in the background along with a versatile user interface and Single Sign on (SSO) Portal implementation. A custom agent may be built out for each participant onboarded onto the system.

With continued reference to FIG. 46, the dispatcher maintains synthetic medical events. The dispatcher exists outside of the Ecosystem, and may inject a medical (or other) event into the agent which will be the framework between the dispatcher and interacting with the vendor electronic medical record or electronic health record (EMR/EHR). The agent distributes the message to the Vendor EMR/EHR and captures any messages as they go through the agent, as described above. The vendor EMR/EHR receives the medical event as it was received from the agent. The adapter sends messages in standardized format to the gateway, and the gateway sends out specific service/messages and receives messages coming in from other implementations. The synthetic patient database contains synthetic patient data and patient records. Information may be retrieved from the patient database when a use case is executed. The viewer EMR/EHR provides a method to define patient information and data, a window into the database. This allows Use Cases to be created by creating specific medical events which occurred with a specific patient, creating a longitudinal profile. The viewer also may provide an area for voluntary upload of personal health information (PHI) by an individual or entity. Work groups may enter information in regards to the Use Cases through this interface. The scheduler correlates the profiles created within the viewer and determines how frequently the synthesized medical events (SME) need to occur to achieve a longitudinal history meeting the Use Case requirements. The user interface or portal (not shown) acts as a method to view information on vendors participating in the system, as well as news, information, branding, advertisements, etc.

The ecosystem provides an environment for various EMR vendors to test and showcase their products to consumers. Moreover, the system allows vendors to discover bugs in their systems prior to selling their product as completely interoperable and able to meet stringent requirements. The ecosystem also provides a forum for consumers to view information as it is exchanged from one organization to another, and provides assurance the solution they are purchasing is interoperable. The ecosystem is in communication with and powered by the DIL, which may be utilized to onboard applicants as participants of an exchange (e.g., a health exchange). The Ecosystem thus provides an additional level of interaction by consumers, reporting metrics, portals, advertisements, and additional features. The ecosystem thus enables a shared learning culture among stakeholders sharing healthcare or other information, and strengthens patient-clinician outcome partnerships through better patient portals and increased availability of lay-oriented, user-friendly clinical and nonmedical health data.

The DIL Ecosystem monitors the secure exchange of health information among multiple vendors utilizing a synthetic patient population, medical events, and multiple visits to various vendors who may be hosting different systems within multiple types of health care providers All publications, patents and/or other references mentioned in this specification are herein incorporated by reference to the same extent as if each individual publication or patent application was specifically and individually indicated to be incorporated by reference in its entirety. It should be clear that the practical implications of interoperability are not confined to the healthcare field, notwithstanding that this field readily demonstrates the value of interoperability in reliable, secure exchange across the spectrum of information sharing. Thus, description of this technology is not intended to be interpreted as exclusive to the healthcare community. Rather, association to the healthcare field of details provided herein is primarily for illustrative value as an example of the invention's general applicability to the technology of information exchange. Thus, while the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. An automated test lab for bidirectional conformance and interoperability testing of an applicant system against a participating system in an information exchange network, the test lab configured to perform the steps of:

intercepting a message between an applicant system and a participating system by an independent test lab;

controlling the intercepted message via an enterprise service bus (ESB) of the test lab, the ESB comprising a processor;

initiating, through a user interface of a web application in communication with the ESB of the test lab, execution of a test scenario based on the intercepted message for determining via the processor whether the intercepted message complies with a set of standards, wherein:

i) the intercepted message is delivered by the test lab to the participating system if the intercepted message complies with the set of standards; or ii) an error message is generated and delivered by the test lab to the applicant system if the intercepted message does not comply with the set of standards; and validating and displaying via the web application results of the executed test scenario.

2. The automated test lab of claim 1, wherein the web application is further configured to create and manage a plurality of test scenarios through the user interface.

3. The automated test lab of claim 1, wherein the test lab comprises a database configured for storing one or more test scenarios, results of executed test scenarios, intercepted messages, configuration files, and audit information.

4. The automated test lab of claim 1, wherein the test scenario comprises one of an initiator scenario or a responder scenario, wherein the initiator scenario tests compliance with the set of standards for requesting or sending information by the applicant system to the participating system, and the responder scenario tests compliance with the set of standards for receiving requests or information from the participating system to the applicant system.

5. The automated test lab of claim 1, wherein the test lab is further configured to generate and send test data to the applicant system for determining compliance with the set of standards, and monitoring and validating responses to the test data by the applicant system.

6. The automated test lab of claim 1, wherein the information exchange network is a shared architecture of multiple systems configured to interconnect health information exchanges.

7. The automated test lab of claim 6, wherein the test lab is further configured to test items within a Direct Health Information Service Provider (HISP).

8. The automated test lab of claim 1, wherein the test lab comprises an integration platform that uses a service oriented architecture (SOA) design.

9. The automated test lab of claim 1, wherein multiple applicant systems are simultaneously tested against multiple participating systems.

10. The automated test lab of claim 1, wherein the test lab is further configured to test Direct Secure Multipurpose Internet Mail Extensions utilizing a Simple Mail Transfer Protocol (SMTP) server.

11. A method of testing conformance and interoperability of an applicant system against a participating system in an information exchange network, comprising the steps of:
generating a request message from an initiating applicant system for a specified receiving participating system; and
intercepting the request message from the initiating applicant system by an independent test lab prior to receipt of the message by the specified receiving participating system, wherein the test lab:
identifies the applicant system; and
determines whether the intercepted request message complies with a set of standards, wherein an error message is generated in response to a noncompliant intercepted message, and a validation message is generated in response to a compliant intercepted message.

12. The method of claim 11, wherein the test lab additionally:
generates a test scenario for determining compliance with the set of standards;
sends the test scenario to the applicant system; and
monitors and validates a response by the applicant system in response to the test scenario.

13. The method of claim 12, wherein the test lab is in communication with a user interface, and the generation of the test scenario is in response to a user request via the user interface.

14. The method of claim 12, wherein the test scenario comprises a request to the applicant system for information from the information exchange network.

15. The method of claim 11, wherein the information exchange network is a shared architecture of multiple systems configured to interconnect health information exchanges.

16. The method of claim 11, wherein the test lab comprises:
a bidirectional gateway with an adapter configured to intercept messages between the initiating applicant system and the receiving participating system, and deliver the intercepted messages to the initiating applicant system or the receiving participating system;
an enterprise service bus (ESB) in communication with the bidirectional gateway adapter and providing an integration platform configured to control the intercepted messages and execute test scenarios based on the intercepted messages for determining compliance with the set of standards; and
a web application in communication with the ESB and configured to initiate through a user interface execution of the test scenarios, and to validate results of the executed test scenarios.

17. The method of claim 16, wherein the integration platform uses a service oriented architecture (SOA) design.

18. The method of claim 11, comprising the further step of validating the intercepted message as either a compliant message or a noncompliant message, and sending a corresponding validation, error, or exception message to the applicant system.

19. The method of claim 11, wherein the information exchange network is a health information exchange utilized by multiple vendors, participants, or Health Information Organizations.

20. A method of testing conformance and interoperability of an applicant system against a participating system in an information exchange network, comprising the steps of:
intercepting a message between an applicant system and a participating system by an independent test lab;
controlling the intercepted message via an enterprise service bus (ESB) of the test lab;
initiating, through a user interface of a web application in communication with the ESB of the test lab, execution of a test scenario based on the intercepted message;
determining whether the intercepted message complies with a set of standards, wherein:
i) the intercepted message is delivered by the test lab to the participating system if the intercepted message complies with the set of standards; or
ii) an error message is generated and delivered by the test lab to the applicant system if the intercepted message does not comply with the set of standards; and
validating and displaying via the web application results of the executed test scenario.

21. The method of claim 20, comprising the further step of creating and managing via the user interface of the web application a plurality of test scenarios.

22. The method of claim 20, wherein the test scenario comprises one of an initiator scenario or a responder scenario, wherein the initiator scenario tests compliance with the set of standards for requesting or sending information by the applicant system to the participating system, and the responder scenario tests compliance with the set of standards for receiving requests or information from the participating system to the applicant system.

23. The method of claim 20, comprising the further steps of generating and sending test data to the applicant system for determining compliance with the set of standards, and monitoring and validating responses to the test data by the applicant system.

24. The method of claim 20, wherein the information exchange network is a shared architecture of multiple systems configured to interconnect health information exchanges.

25. The method of claim 20, comprising the further step of testing items within a Direct Health Information Service Provider (HISP).

26. The method of claim 20, wherein the test lab comprises an integration platform that uses a service oriented architecture (SOA) design.

27. The method of claim 20, comprising the step of simultaneously testing multiple applicant systems against multiple participating systems.

28. The method of claim 20, comprising the further step of testing Direct Secure Multipurpose Internet Mail Extensions utilizing a Simple Mail Transfer Protocol (SMTP) server.

* * * * *